(12) United States Patent
Chuang et al.

(10) Patent No.: US 9,708,310 B2
(45) Date of Patent: Jul. 18, 2017

(54) PHENANTHROINDOLIZIDINE AND PHENANTHROQUINOLIZIDINE ALKALOID HAVING A HYDROXYL GROUP ON THE PHENANTHRENE RING THEREOF, PREPARATION METHOD AND USE THEREOF

(71) Applicants: Ta-Hsien Chuang, Taichung (TW); Chien-Fu Li, Taichung (TW); Chia-Chen Tsai, Taichung (TW); Chi-Fen Chang, Taichung (TW); Chieh-Yu Peng, New Taipei (TW)

(72) Inventors: Ta-Hsien Chuang, Taichung (TW); Chien-Fu Li, Taichung (TW); Chia-Chen Tsai, Taichung (TW); Chi-Fen Chang, Taichung (TW); Chieh-Yu Peng, New Taipei (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 15/015,279

(22) Filed: Feb. 4, 2016

(65) Prior Publication Data
US 2017/0152257 A1  Jun. 1, 2017

(30) Foreign Application Priority Data

Dec. 1, 2015 (TW) ............................. 104140232 A

(51) Int. Cl.
*C07D 455/03* (2006.01)

(52) U.S. Cl.
CPC .................................. *C07D 455/03* (2013.01)

(58) Field of Classification Search
CPC ...................................................... C07D 455/03
USPC ...................................................... 546/42, 58
See application file for complete search history.

(56) References Cited

PUBLICATIONS

Chang et al., Organic Letters (2016), 18(4), 638-641.*

* cited by examiner

*Primary Examiner* — Niloofar Rahmani
(74) *Attorney, Agent, or Firm* — Bacon & Thomas, PLLC

(57) ABSTRACT

A phenanthroindolizidine and phenanthroquinolizidine alkaloid having a hydroxyl group on the phenanthrene ring thereof was synthesized, which exhibits potent activity as an anticancer agent against, such as breast cancer, lung cancer, and prostate cancer.

10 Claims, 1 Drawing Sheet

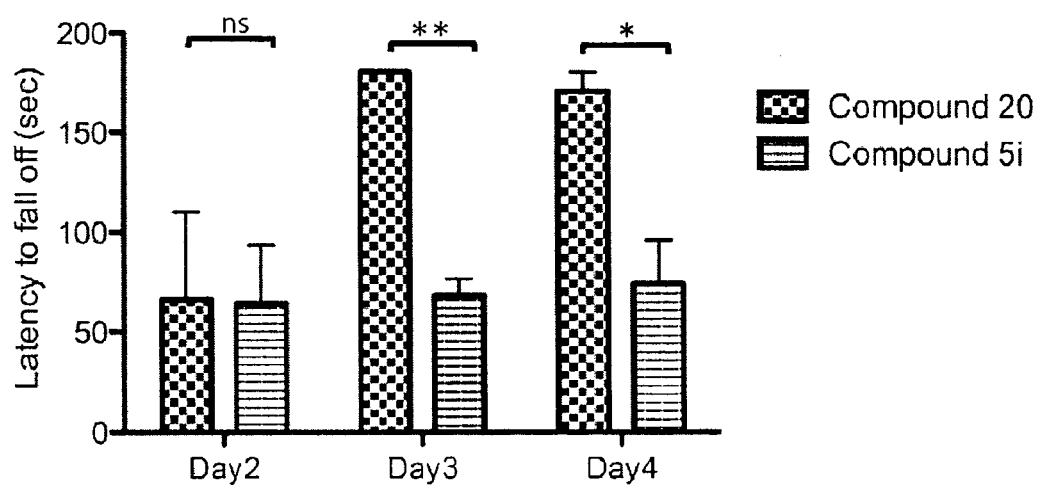

PHENANTHROINDOLIZIDINE AND PHENANTHROQUINOLIZIDINE ALKALOID HAVING A HYDROXYL GROUP ON THE PHENANTHRENE RING THEREOF, PREPARATION METHOD AND USE THEREOF

FIELD OF THE INVENTION

The present invention is related to phenanthroindolizidine and phenanthroquinolizidine alkaloid having a hydroxyl group on the phenanthrene ring thereof, preparation method thereof and use thereof as an anticancer agent.

BACKGROUND OF THE INVENTION

US2010/0216773 A1 discloses a method for preparing a phenanthroindolizidine and phenanthroquinolizidine alkaloid, and in Example 1 thereof a mixture of compounds of 13-16 are allegedly synthesized by partial hydrolysis of compound 28, where the structures of the compounds 13-16 and 28 are shown as follows:

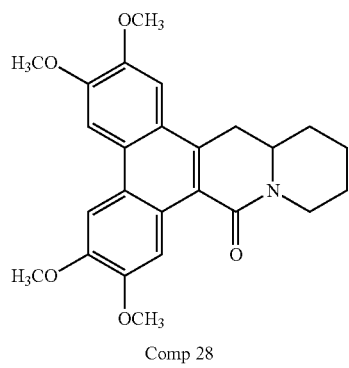

Comp 28

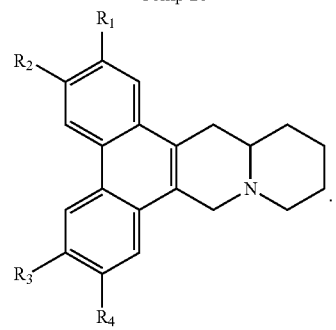

Comp 13: $R_1$ = OH, $R_2$, $R_3$, $R_4$, = $OCH_3$
Comp 14: $R_2$ = OH, $R_1$, $R_3$, $R_4$, = $OCH_3$
Comp 15: $R_3$ = OH, $R_1$, $R_2$, $R_4$, = $OCH_3$
Comp 16: $R_4$ = OH, $R_1$, $R_2$, $R_3$, = $OCH_3$ These four compounds 13-16 disclosed in US2010/0216773 A1 cannot be obtained by the treatment of compound 28 with sodium bis(2-methoxyethoxy)aluminium hydride, a reducing agent, according to our previous method. [T. H. Chuang, S. J. Lee, C. W. Yang, P. L Wu *Org. Biomol. Chem.* 2006, 4, 860-867.].

SUMMARY OF THE INVENTION

The present invention discloses a novel method for preparing a phenanthroindolizidine and phenanthroquinolizidine alkaloid, and in particular a method for preparing a phenanthroindolizidine and phenanthroquinolizidine alkaloid having a hydroxyl group on the phenanthrene ring thereof, which shows an improved solubility in an aqueous solvent system and potent cytotoxicity activity against breast cancer, lung cancer, and prostate cancer.

Preferred embodiments of the present invention include (but not limited to) the following items:

1. An improved method for preparing a phenanthroindolizidine and phenanthroquinolizidine alkaloid having a structure represented by the following formula (I):

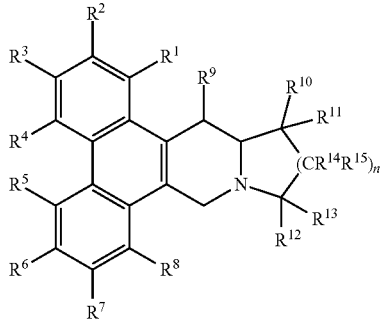

(I)

wherein n is 1, 2, or 3; each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$, independently, is H, halogen, alkyl, aryl, cyclyl, heteroaryl, heterocyclyl, OH, alkoxy, or amino;

wherein the improvement comprises the method comprising step (5): conducting a reductive decyanization reaction of an aminoacrylonitrile derivative having a structure represented by the following formula (III) to obtain a diphenyltetrahydropyridine derivative having a structure represented by the following formula (II):

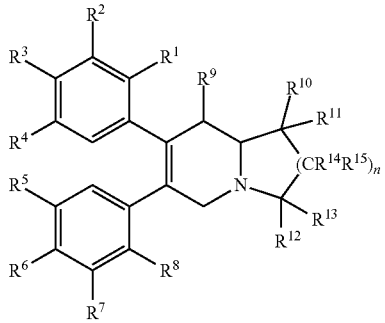

(II)

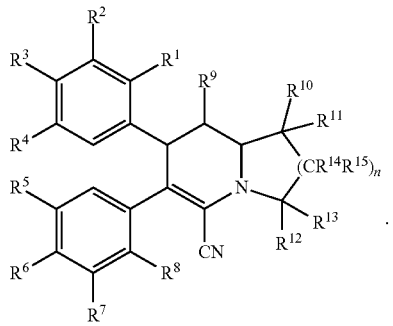

(III)

2. The method of Item 1 further comprising a step (6): conducting an aryl-aryl oxidative coupling reaction of the diphenyltetrahydropyridine derivative (II) to obtain the phenanthroindolizidine and phenanthroquinolizidine alkaloid (I).

3. The method of Item 1 further comprising a step (4): conducting an intramolecular aza-Diels-Alder reaction of an iminonitrile derivative having a structure represented by the following formula (IV) and to obtain the aminoacrylonitrile derivative (III):

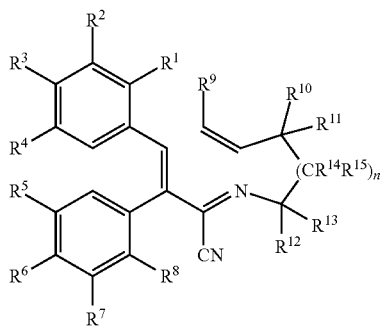

(IV)

wherein definitions of n, $R^1$, $R^2$, $R^3$, $R^4$, $R^5$, $R^6$, $R^7$, $R^1$, $R^9$, $R^{10}$, $R^{11}$, $R^2$, $R^{13}$, $R^{14}$, and $R^{15}$ are the same as in claim 1.

4. The method of Item 3 further comprising step (3): reacting a vinyl amine derivative having a structure represented by the following formula (V) with an (E)-2,3-diphenylacrylaldehyde derivative having a structure represented by the following formula (VI) to obtain the iminonitrile derivative (IV):

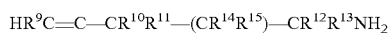

(V)

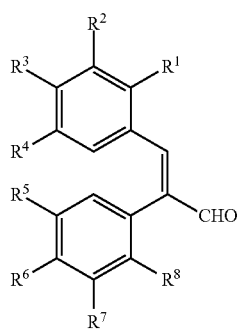

(VI)

wherein definitions of n, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are the same as in claim 1.

5. The method of Item 4 further comprising a step (2): conducting a diisobutylaluminum hydride reduction of a diphenylacrylonitrile derivative having a structure represented by the following formula (VII) to obtain the (E)-2,3-diphenylacrylaldehyde derivative (VI):

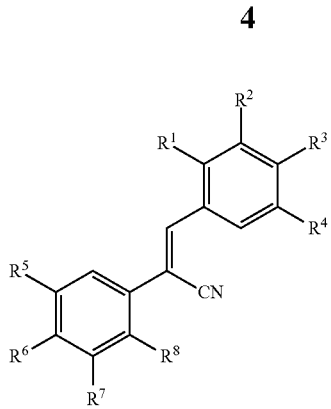

(VII)

wherein definitions of $R^1$, $R^2$, $R^3$, $R^4$, $R^5$, $R^6$, $R^7$, and $R^8$ are the same as in claim 1.

6. The method of Item 5 further comprising a step (1): conducting a Knoevenagel condensation of a benzaldehyde derivative having a structure represented by the following formula (VIII) and a phenylacetonitrile derivative having a structure represented by the following formula (IX) to obtain the diphenylacrylonitrile derivative h (VII):

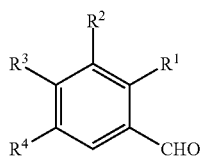

(VIII)

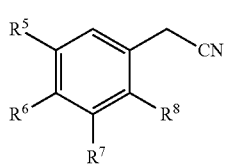

(IX)

wherein definitions of $R^1$, $R^2$, $R^3$, $R^4$, $R^5$, $R^6$, $R^7$, and $R^8$ are the same as in claim 1.

7. A phenanthroindolizidine and phenanthroquinolizidine alkaloid having a structure represented by the following formula (I),

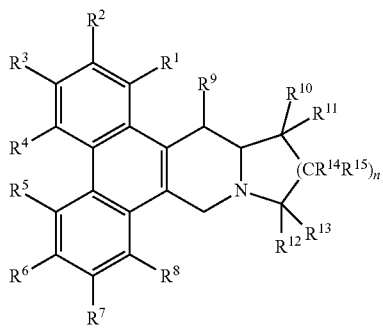

(I)

wherein n is 1, 2, or 3; each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$, independently, is H, halogen, alkyl, aryl, cyclyl, heteroaryl, heterocyclyl, OH, alkoxy, or amino; wherein at least one of $R^1$, $R^2$, $R^3$, $R^4$, $R^5$, $R^6$, $R^7$ and Re is OH; and wherein the alkaloid (I) exists without mixing with another phenanthroindolizidine and phenanthroquinolizidine alkaloid.

8. The phenanthroindolizidine and phenanthroquinolizidine alkaloid of Item 7, which is dissolved in water or an aqueous solution.

9. The method of Item 1, wherein n=2; $R^1$, $R^8$, $R^9$, $R^{10}$, $R^{11}$, $R^{12}$, $R^{13}$, $R^{14}$, and $R^{15}$ are H.

10. The method of Item 9, wherein each of $R^2$, $R^3$, $R^4$, $R^5$, $R^6$, and $R^7$, independently, is H, OH, or alkoxy.

11. The method of Item 10, wherein at least one of $R^2$, $R^3$, $R^4$, $R^5$, $R^6$, and $R^7$ is OH.

12. The method of Item 11, wherein $R^2$, $R^3$, and $R^6$ are methoxy; and $R^7$ is OH.

13. The phenanthroindolizidine and phenanthroquinolizidine alkaloid of Item 7, wherein n=2; $R^1$, $R^8$, $R^9$, $R^{10}$, $R^{11}$, $R^{12}$, $R^{13}$, $R^{14}$, and $R^5$ are H.

14. The phenanthroindolizidine and phenanthroquinolizidine alkaloid of Item 13, wherein each of $R^2$, $R^3$, $R^4$, $R^5$, $R^6$, and $R^7$, independently, is H, OH, or alkoxy.

15. The phenanthroindolizidine and phenanthroquinolizidine alkaloid of Item 14, wherein $R^2$, $R^3$, and $R^6$ are methoxy; and $R^7$ is OH.

16. A method for treating a cancer comprising administering to a subject in need thereof an effective amount of a phenanthroindolizidine and phenanthroquinolizidine alkaloid having a structure represented by the following formula (I):

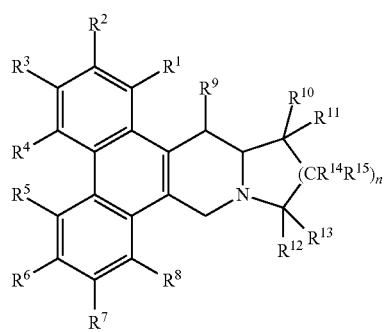

wherein n=2; $R^9$, $R^{10}$, $R^{11}$, $R^{12}$, $R^{13}$, $R^{14}$, and $R^{15}$ are H; $R^2$, $R^3$, and $R^6$ are alkoxy; $R^1$, $R^4$, $R^5$, $R^7$ and $R^8$, independently, are H, OH, or alkoxy; and at least one of $R^1$, $R^4$, $R^5$, $R^7$ and $R^8$ is OH; and wherein the cancer is selected from the group consisting of breast cancer, lung cancer, and prostate cancer.

17. The method of Item 16, wherein $R^2$, $R^3$, and $R^6$ are methoxy; $R^1$, $R^4$, $R^5$, and $R^8$, independently, are H or methoxy; and $R^7$ is OH.

18. The method of Item 17, wherein the alkaloid has a structure represented by the following formula:

BRIEF DESCRIPTION OF THE DRAWING

The FIGURE shows the results of neurotoxicity of compounds 20 and 5i synthesized in accordance with the method of the present invention, determined by a rotarod test for motor coordination.

DETAILED DESCRIPTION OF THE INVENTION

Tylophorine, a phenanthroindolizidine alkaloid, was first isolated from *Tylophora asthmatica* (Asclepiadaceae) in 1935 by Rathnagiriswaran and co-worker. (A. N. Rathnagiriswaran, K. Venkatachalam, *Indian J. Med. Res.* 1935, 22, 433-441) Phenanthroindolizidines and phenanthroquinolizidines exhibit several interesting biological activities such as anticancer, antiamoebic, antibacterial, and antifungal activities; eight comprehensive reviews have been published from 1978 to 2015. [a) T. R. Govindachari, N. Viswanathan, *Heterocycles* 1978, 11, 587-613; b) I. R. C. Bick, W. Sinchai, *Alkaloids* 1981, 19, 193-220; c) E. Gellert, *J. Nat. Prod.* 1982, 45, 50-73; d) Z. Li, Z. Jin, R. Huang, *Synthesis* 2001, 16, 2365-2378; e) C. G Zhang, X. D. Tan, *Sichuan Shifan Daxue Xuebao, Ziran Kexueban* 2005, 28, 366-370; f) S. R. Chemler, *Cur. Bioact. Compd.* 2009, 5, 2-19; g) A. C. B. Burtoloso, A. F. Bertonha, I. G. Rosset, *Curr. Top. Med. Chem.* 2014, 14, 191-199; h) de Fatima Pereira, M., C. Rochais, P. Dallemagne, *Anticancer Agents Med. Chem.* 2015, 15, 1080-1091.] Unfortunately, high doses of (R)-tylophorine (1) caused central nervous system (CNS) side effects in rats, and (R)-tylocrebrine (2) failed in the early clinical trial owing to CNS toxicity. [a) C. Gopalakrishnan, D. Shankaranarayan, L. Kameswaran, S. Natarajan, *Indian J. Med. Res.* 1979, 69, 513-520; b) M. Suffness, J. Douros, *Anticancer Agents Based on Natural Product Models*, Academic, New York, 1981, pp. 465-487] The CNS side effects (e.g., disorientation, ataxia, and decreased motor activity) of compounds 1 and 2 and their low water solubility urgently need to be addressed before attempting clinical trials again. A more polar analog, as proposed by Suffness mentioned above, will minimize or prevent the CNS side effects owing to decreased diffusion through the blood-brain barrier (BBB). Indeed, hydroxylated cryptopleurine 3 significantly reduced the BBB penetration as predicted by PreADMET; unfortunately, no further in vivo result was reported. [X. Yang, Q. Shi, C. Y. Lai, C. Y. Chen, E. Ohkoshi, S. C. Yang, et al., *J. Med. Chem.* 2012, 55, 6751-6761.]

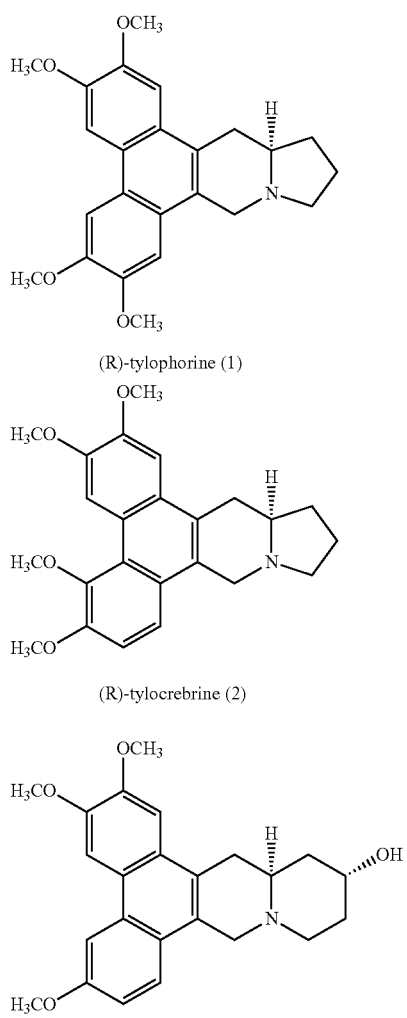

(R)-tylophorine (1)

(R)-tylocrebrine (2)

3

Although several previously reported routes were concise [a) T. R. Govindachari, N. Viswanathan, *Heterocycles* 1978, 11, 587-613; b) I. R. C. Bick, W. Sinchai, *Alkaloids* 1981, 19, 193-220; c) E. Gellert, *J. Nat. Prod.* 1982, 45, 50-73; d) Z. Li, Z. Jin, R. Huang, *Synthesis* 2001, 16, 2365-2378; e) C. G. Zhang, X. D. Tan, *Sichuan Shifan Daxue Xuebao, Ziran Kexueban* 2005, 28, 366-370; f) S. R. Chemler, *Cur. Bioact. Compd.* 2009, 5, 2-19; g) A. C. B. Burtoloso, A. F. Bertonha, I. G. Rosset, *Curr. Top. Med. Chem.* 2014, 14, 191-199; h) de Fatima Pereira, M., C. Rochais, P. Dallemagne, *Anticancer Agents Med. Chem.* 2015, 15, 1080-1091.], the syntheses of phenanthroindolizidines and phenanthroquinolizidines focused only on specific positions (C-2, C-3, C-6, and C-7) of the phenanthrene ring owing to the limitations of the synthetic methods. In the present invention, we envision that a pentacyclic alkaloid with a hydroxyl group on the phenanthrene ring would improve water solubility and polarity. Thus, we disclose a novel method for synthesizing phenanthroindolizidine and phenanthroquinolizidine alkaloids with three to five methoxyl groups on C-1 to C-8 positions of the phenanthrene ring, and a potent anticancer analog by converting the methoxy group into a hydroxyl group was discovered in the present invention.

Herein, we disclose a concise strategy to construct pyrrolizidine and indolizidine systems by a cyano-group-promoted IADA (Intramolecular aza-Diels-Alder) reaction followed by reductive decyanization (Scheme 1). A series of phenanthroindolizidines 4 and phenanthroquinolizidines 5 were synthesized from decyanization products 10 and 11 via aryl-aryl oxidative coupling reactions. This tandem reaction sequence provides a new synthetic approach to this type of pentacyclic alkaloids.

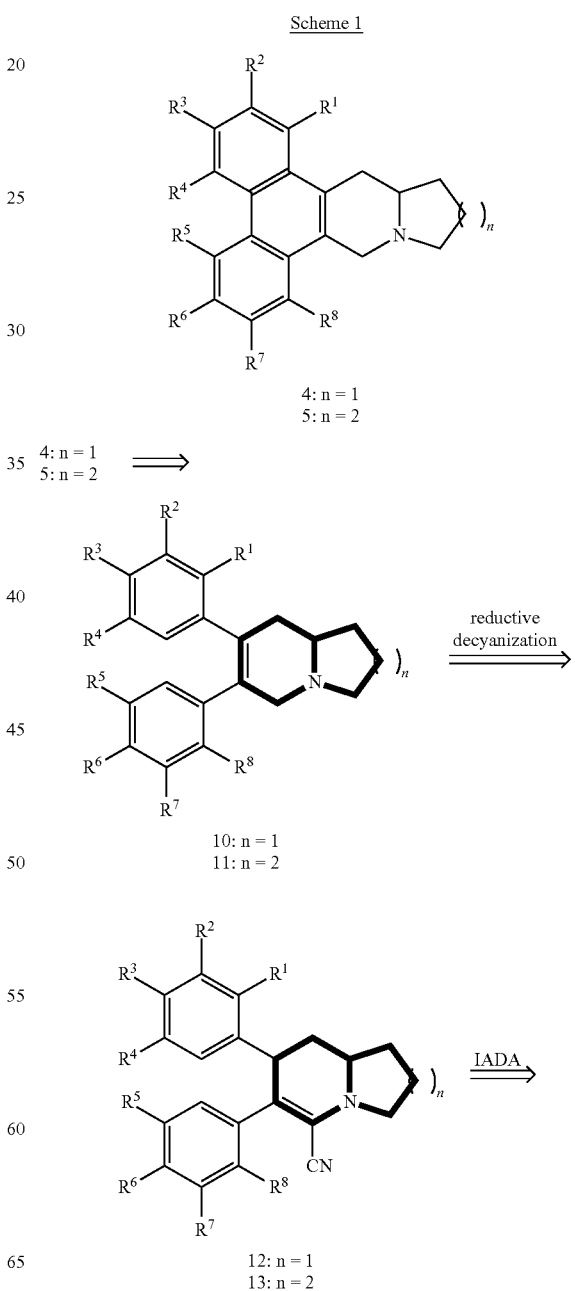

Scheme 1

-continued

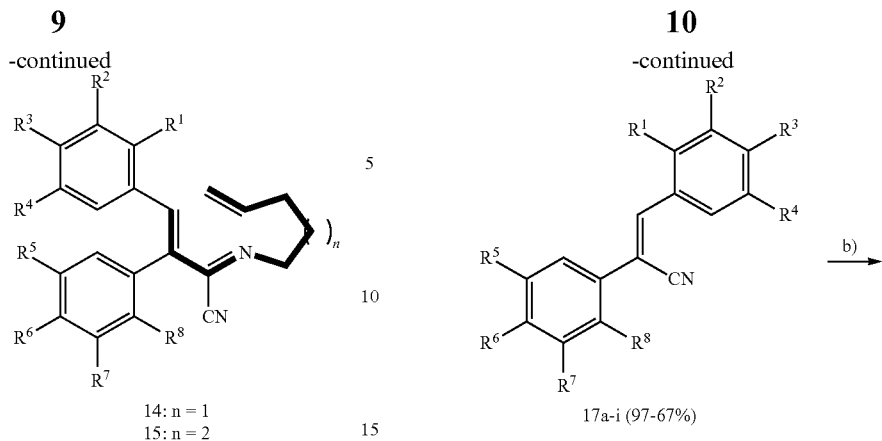

14: n = 1
15: n = 2

17a-i (97-67%)

Scheme 2 shows the synthesis of IADA precursors 14a-i and 15a-i. First, the (E)-2,3-diphenylacrylaldehydes 16a-i were synthesized by the Knoevenagel condensation of benzaldehydes 18v-z with phenylacetonitriles 19v-z, followed by DIBAL-H reduction (T. H. Chuang, W. Y. Chang, C. F. Li, Y. C. Wen, C. C. Tsai, J. Org. Chem. 2011, 76, 9678-9686). Next, a-iminonitrile 14l was synthesized in a low yield, probably because of poor solubility, by the one-pot reaction of acrylaldehyde 16l, pent-4-enylamine, trimethylsilyl cyanide (TMSCN), 2-iodoxybenzoic acid (IBX), and tetrabutylammonium bromide (TBAB) in CH$_3$CN following the method of Zhu et al. (P. Fontaine, A. Chiaroni, G Masson, J. Zhu, Org. Lett. 2008, 10, 1509-1512) Nevertheless, a two-step method was developed to synthesize 2-(alkenylimino)-3,4-diphenyl-(3E)-butenenitriles 14a-i and 15a-i in good yields via Schiff base formation (Scheme 2).

16a-i (91-60%)

Scheme 2

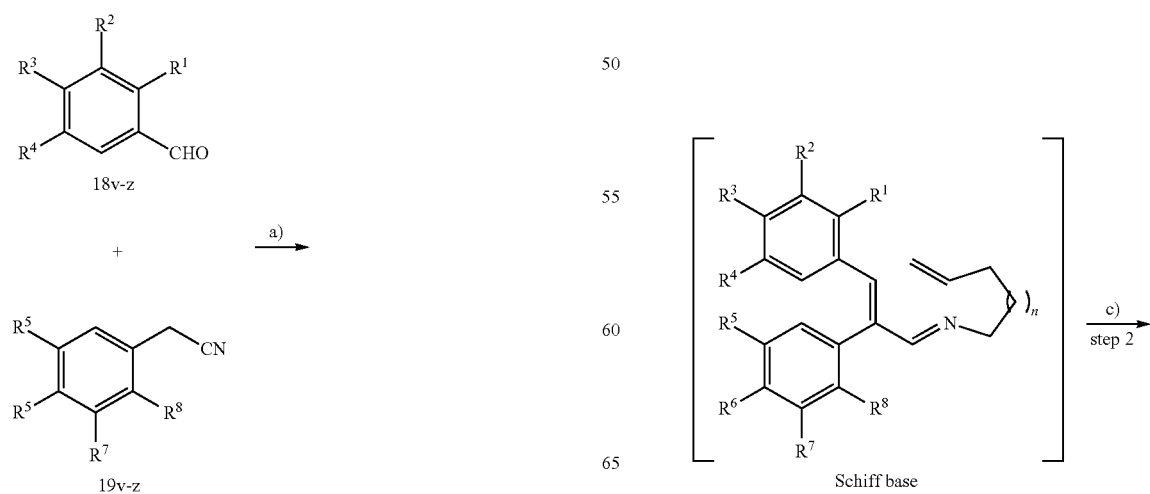

18v-z

+

19v-z

Schiff base

-continued

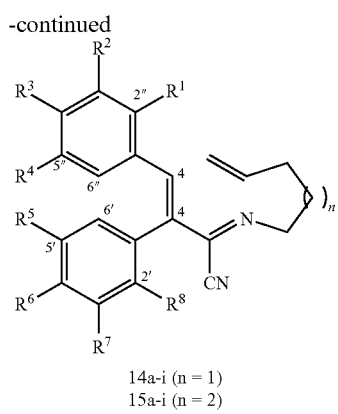

14a-i (n = 1)
15a-i (n = 2)

14a (80%): 15a (81%) $R^1 = R^2 = R^3 = R^6 = R^7 = OCH_3$; others = H
14b (78%): 15b (83%) $R^3 = R^6 = R^7 = OCH_3$; others = H
14c (81%): 15c (83%) $R^2 = R^6 = R^7 = OCH_3$; others = H
14d (80%): 15d (80%) $R^2 = R^3 = R^4 = R^6 = R^7 = OCH_3$; others = H
14e (86%): 15e (82%) $R^2 = R^3 = R^5 = R^6 = R^7 = OCH_3$; others = H
14f (89%): 15f (88%) $R^2 = R^3 = R^7 = OCH_3$; others = H
14g (76%): 15g (83%) $R^2 = R^3 = R^6 = OCH_3$; others = H
14h (78%): 15h (75%) $R^2 = R^3 = R^6 = R^7 = R^8 = OCH_3$; others = H
14i (86%): 15i (85%) $R^2 = R^3 = R^6 = R^7 = OCH_3$; others = H Next, 3,4-bis(3,4-dimethoxyphenyl)-2-(4-pentenylimino)-(3E)-butenenitrile 14l was selected as the initial model to investigate the feasibility of the IADA reaction. Conventional heating was selected over microwave heating, because the cycloaddition reaction of compound 14l did not reach completion under the microwave conditions. A 0.05 M solution of compound 14l in toluene in a sealed tube was heated at 165° C. under the maximum power 250 W for 3 h using a focused microwave reactor. A solution of compound 14l in toluene was refluxed for 72 h, affording cycloadduct 12l in 58% yield. A similar result was obtained by heating the mixture in a sealed tube at 130° C. for 48 h. To our delight, the cycloaddition of compound 14l could be carried out in a sealed tube by heating at 160° C. for overnight, affording trans-12i (64% yield) and cis-12i (7% yield). All the IADA reactions of 2-(alkenylimino)-3,4-diphenyl-(3E)-butenenitriles 14a-i and 15a-i were conducted under the above optimum conditions, and the yields are shown in Table 1. The IADA reactions of compounds 14b-i with a three-atom spacer afforded cycloadducts 12b-i in trans/cis ratios of ca. 10:1 as determined from their crude $^1$H NMR spectra. Interestingly, when IADA precursors 15a-i with a four-atom spacer were used, stereospecific cycloadducts trans-13a-i were obtained in high yields. Thus, the efficiency of the IADA reactions and the trans/cis diastereomeric ratios of the IADA cycloadducts are affected by the spacer length. The IADA reactions of 15a-i proceeded exclusively through a more stable exo transition state, affording the thermodynamically less stable trans-13a-i as the main products.

TABLE 1

Yields of IADA cycloadducts 12 and trans-13

| Entry | 14 | 15 | Substituent[a] | Yield [%] 12[b] | Yield [%] 13[c] |
|---|---|---|---|---|---|
| 1 | 14a | 15a | $R^1 = R^2 = R^3 = R^6 = R^7 = OCH_3$ | 60 (12a) | 84 (13a) |
| 2 | 14b | 15b | $R^3 = R^6 = R^7 = OCH_3$ | 73 (12b) | 90 (13b) |
| 3 | 14c | 15c | $R^2 = R^6 = R^7 = OCH_3$ | 78 (12c) | 91 (13c) |
| 4 | 14d | 15d | $R^2 = R^3 = R^4 = R^6 = R^7 = OCH_3$ | 67 (12d) | 90 (13d) |
| 5 | 14e | 15e | $R^2 = R^3 = R^5 = R^6 = R^7 = OCH_3$ | 62 (12e) | 86 (13e) |
| 6 | 14f | 15f | $R^2 = R^3 = R^7 = OCH_3$ | 70 (12f) | 90 (13f) |
| 7 | 14g | 15g | $R^2 = R^3 = R^6 = OCH_3$ | 70 (12g) | 92 (13g) |
| 8 | 14h | 15h | $R^2 = R^3 = R^6 = R^7 = R^8 = OCH_3$ | 78 (12h) | 93 (13h) |
| 9 | 14i | 15i | $R^1 = R^3 = R^6 = R^7 = OCH_3$ | 71 (12i) | 92 (13i) |
| 9 | 14i | 15i | $R^2 = R^3 = R^6 = R^7 = OCH_3$ | 71 (12i) | 92 (13i) |

[a]The substituents not mentioned are hydrogens.

[b]The IADA reactions of compounds 14b-i with a three-atom spacer afforded cycloadducts 12b-i in trans/cis ratios of ca. 10:1. Trans/cis diastereomeric mixtures 12 were used in the next step.

[c]Diastereomers trans-13a-i were obtained predominantly.

With a series of 6,7-diphenylindolizine-5-carbonitriles (12a-i) and trans-2,3-diphenylquinolizine-4-carbonitriles (trans-13a-i) in hand, an efficient method was developed for the removal of the cyano group from α-aminoacrylonitriles: A mixture of cycloadducts 12a-i (and trans-13a-i) and 10 equiv NaBH$_4$ in 2-propanol in a sealed tube was heated at 100° C. for 24 h. The decyanization products, 6,7-diphenylindolizines 10a- and 7,8-diphenylquinolizines 11a-i, were obtained in almost quantitative yields (Table 2).

TABLE 2

Reductive decyanization of α-aminoacrylonitriles 12 and trans-13.

| Entry | 12 | 13 | Substituent[a] | Yield [%] 10 | Yield [%] 11 |
|---|---|---|---|---|---|
| 1[c] | 12a | 13a | $R^1 = R^2 = R^3 = R^6 = R^7 = OCH_3$ | 92 (10a) | 95 (11a) |
| 2[b] | 12b | 13b | $R^3 = R^6 = R^7 = OCH_3$ | 100 (10b) | 100 (11b) |
| 3[b] | 12c | 13c | $R^2 = R^6 = R^7 = OCH_3$ | 100 (10c) | 100 (11c) |
| 4[b] | 12d | 13d | $R^2 = R^3 = R^4 = R^6 = R^7 = OCH_3$ | 96 (10d) | 98 (11d) |
| 5[b] | 12e | 13e | $R^2 = R^3 = R^5 = R^6 = R^7 = OCH_3$ | 100 (10e) | 100 (11e) |
| 6[b] | 12f | 13f | $R^2 = R^3 = R^7 = OCH_3$ | 100 (10f) | 100 (11f) |
| 7[b] | 12g | 13g | $R^2 = R^3 = R^6 = OCH_3$ | 100 (10g) | 100 (11g) |
| 8[c] | 12h | 13h | $R^2 = R^3 = R^6 = R^7 = R^8 = OCH_3$ | 94 (10h) | 97 (11h) |
| 9[b] | 12i | 13i | $R^1 = R^3 = R^6 = R^7 = OCH_3$ | 100 (10i) | 100 (11i) |

[a]The substituents not mentioned are hydrogens.
[b]Reactions were carried out at 100° C. and
[c]120° C.

Finally, an efficient oxidizing agent, vanadium oxytrifluoride (VOF$_3$), was chosen to examine the oxidative aryl-aryl coupling of 6,7-diphenylindolizines 10a-i and 7,8-diphenylquinolizines 11a-i Phenanthroindolizidines 4b, 4c, 4f, 4g, and 4I as well as phenanthroquinolizidines 5b, 5c, 5f, 5g, and 5i with three or four methoxyl groups could be smoothly synthesized under Park's conditions (method A, entries 2, 3, 6, 7, and 9 in Table 3). [X. Xu, Y. Liu, C. M. Park, Angew. Chem. Int. Ed. 2012, 51, 9372-9376.] However, an attempt to prepare phenanthroquinolizidine 5a with five methoxyl groups under the same conditions resulted in extensive oxidative decomposition. To our delight, phenanthroindolizidines 4a, 4d, 4e, and 4h as well as phenanthroquinolizidines 5a, 5d, 5e, and 5h with five methoxyl groups could be obtained in good to moderate yields (entries 1, 4, 5, and 8 in Table 3) with complete regiospecificity under mild conditions (method B: 2 equiv VOF$_3$, −20° C.). The total synthesis of phenanthroindolizidines 4a-i and phe-nanthroquinolizidines 5a-i from benzaldehydes with phenylacetonitriles was achieved in six steps in 8.8-42.1% and 19.3-63.5% overall yields, respectively. To the best of our knowledge, this is a novel and concise strategy to construct these types of pentacyclic skeletons.

TABLE 3

Aryl-aryl coupling of cis-stilbenes 10 and 11.

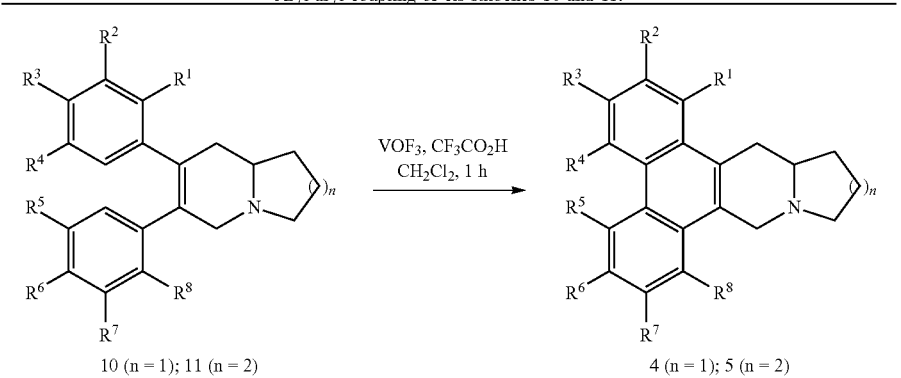

10 (n = 1); 11 (n = 2) → 4 (n = 1); 5 (n = 2)

| Entry | 10 | 11 | Substituent[a] | Yield [%] 4 | Yield [%] 5 |
|---|---|---|---|---|---|
| 1[b] | 10a | 11a | $R^1 = R^2 = R^3 = R^6 = R^7 = OCH_3$ | 70 (4a) | 77 (5a) |
| 2[a] | 10b | 11b | $R^3 = R^6 = R^7 = OCH_3$ | 82 (4b) | 88 (5b) |
| 3[b] | 10c | 11c | $R^2 = R^6 = R^7 = OCH_3$ | 86 (4c) | 84 (5c) |
| 4[b] | 10d | 11d | $R^2 = R^3 = R^4 = R^6 = R^7 = OCH_3$ | 89 (4d) | 90 (5d) |
| 5[b] | 10e | 11e | $R^2 = R^3 = R^5 = R^6 = R^7 = OCH_3$ | 85 (4e) | 88 (5e) |
| 6[a] | 10f | 11f | $R^2 = R^3 = R^7 = OCH_3$ | 85 (4f) | 86 (5f) |
| 7[a] | 10g | 11g | $R^2 = R^3 = R^6 = OCH_3$ | 86 (4g) | 88 (5g) |
| 8[b] | 10h | 11h | $R^2 = R^3 = R^6 = R^7 = R^8 = OCH_3$ | 54 (4h) | 71 (5h) |
| 9[a] | 10i | 11i | $R^1 = R^3 = R^6 = R^7 = OCH_3$ | 85 (4i) | 92 (5i) |

[a]Method A: a 0.04 M solution of 10 or 11 (0.2 mmol) in anhydrous $CH_2Cl_2$ (5 mL) was added to $VOF_3$ (1.0 mmol) at 0° C. and the mixture was stirred for 15 min. TFA (2.8 mmol) was added and the mixture was stirred at 0° C. for 1 h.
[b]Method B: a 0.04 M solution of 10 or 11 (0.2 mmol) in anhydrous $CH_2Cl_2$ (5 mL) was added to $VOF_3$ (0.4 mmol) at −20° C. and the mixture was stirred for 15 min. TFA (2.8 mmol) was added and the mixture was stirred at −20° C. for 1 h.
[c]The substituents not mentioned are hydrogens.

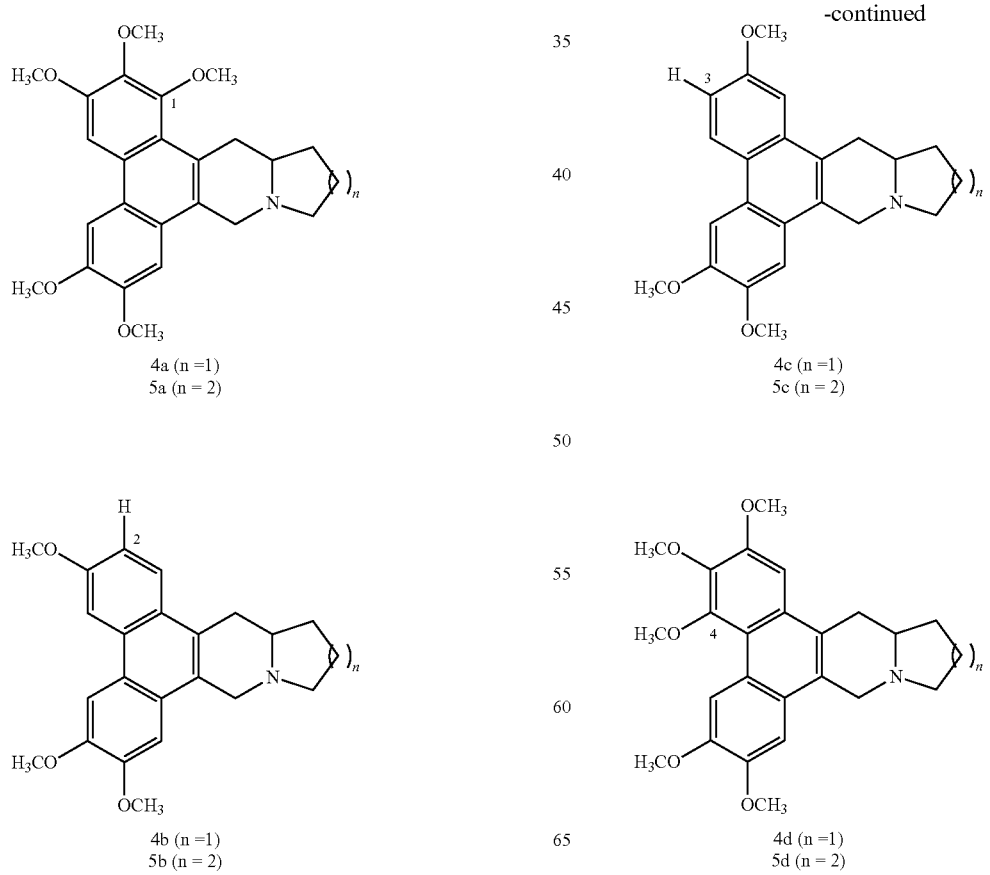

4a (n = 1); 5a (n = 2)

4c (n = 1); 5c (n = 2)

4b (n = 1); 5b (n = 2)

4d (n = 1); 5d (n = 2)

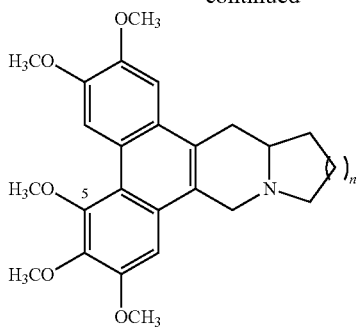

4e (n = 1)
5e (n = 2)

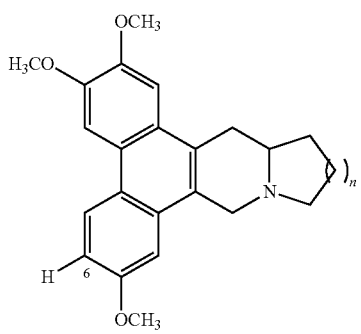

4f (n = 1)
5f (n = 2)

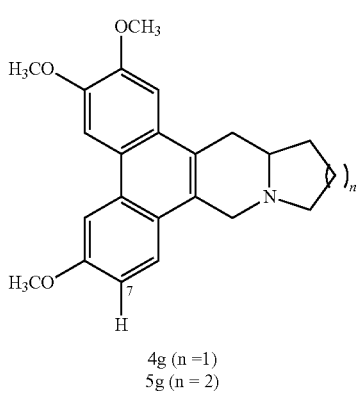

4g (n = 1)
5g (n = 2)

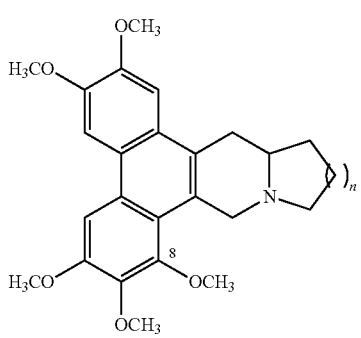

4h (n = 1)
5h (n = 2)

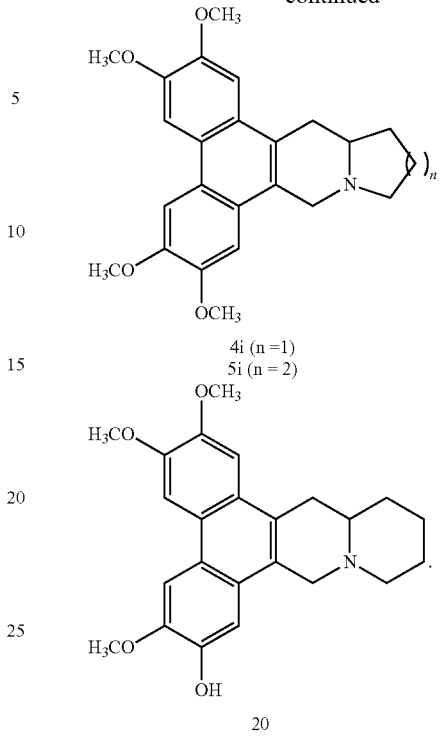

4i (n = 1)
5i (n = 2)

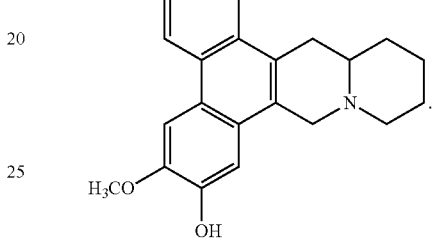

20

Based on the SAR results, a more polar phenanthroquinolizidine, 7-hydroxycryptopleurine (20), was designed and synthesized to decrease the CNS toxicity and increase the water solubility. 7-Hydroxycryptopleurine (20) was obtained from 3-benzyloxy-4-methoxybenzaldehyde in 40.7% overall yield by the above newly developed method.

EXAMPLES

1. Synthesis of (Z)-2,3-diphenylacrylonitriles 17a-i

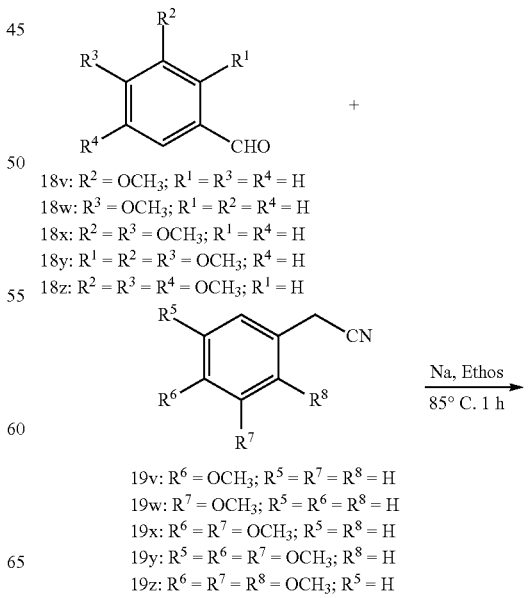

18v: $R^2 = OCH_3$; $R^1 = R^3 = R^4 = H$
18w: $R^3 = OCH_3$; $R^1 = R^2 = R^4 = H$
18x: $R^2 = R^3 = OCH_3$; $R^1 = R^4 = H$
18y: $R^1 = R^2 = R^3 = OCH_3$; $R^4 = H$
18z: $R^2 = R^3 = R^4 = OCH_3$; $R^1 = H$

19v: $R^6 = OCH_3$; $R^5 = R^7 = R^8 = H$
19w: $R^7 = OCH_3$; $R^5 = R^6 = R^8 = H$
19x: $R^6 = R^7 = OCH_3$; $R^5 = R^8 = H$
19y: $R^5 = R^6 = R^7 = OCH_3$; $R^8 = H$
19z: $R^6 = R^7 = R^8 = OCH_3$; $R^5 = H$

Na, Ethos
85° C. 1 h

-continued

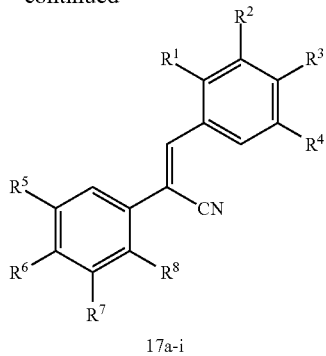

17a-i

17a: $R^1 = R^2 = R^3 = R^6 = R^7 = OCH_3$; others = H
17b: $R^3 = R^6 = R^7 = OCH_3$; others = H
17c: $R^2 = R^6 = R^7 = OCH_3$; others = H
17d: $R^2 = R^3 = R^4 = R^6 = R^7 = OCH_3$; others = H
17e: $R^2 = R^3 = R^5 = R^6 = R^7 = OCH_3$; others = H
17f: $R^2 = R^3 = R^7 = OCH_3$; others = H
17g: $R^2 = R^3 = R^6 = OCH_3$; others = H
17h: $R^2 = R^3 = R^6 = R^7 = R^8 = OCH_3$; others = H
17i: $R^2 = R^3 = R^6 = R^7 = OCH_3$; others = H Typical procedure for the synthesis of (Z)-2,3-diphenylacrylonitrile 17 according to the literature. [T. H. Chuang, W. Y. Chang, C. F. Li, Y. C. Wen, C. C. Tsai, J. Org. Chem. 2011, 76, 9678-9686] A fresh 1 M NaOEt solution (prepared from Na (5.06 g, 22 mmol) in absolute EtOH (22 mL)) was added in one portion to a stirred solution of benzaldehydes 18v-z (20 mmol) and phenylacetonitriles 19v-z (20 mmol) in absolute EtOH (100 mL) at RT. The mixture was heated at 85° C. under $N_2$ for 1 h. If no precipitate was formed at RT, the mixture was cooled to −20° C. The resulting precipitate was filtered and washed with small amounts of cold EtOH, affording (Z)-2,3-diphenylacrylonitrile 17a-i. The complete spectral data of these compounds are given below.

(Z)-3-(2,3,4-Trimethoxyphenyl)-2-(3,4-dimethoxyphenyl)acrylonitrile (17a)

Yield 94%; pale yellow needle, mp 107-108° C. (hexane-EtOAc).
$^1$H NMR (500 MHz, CDCl$_3$): δ 3.89 (3H, s), 3.93 (9H, s), 3.96 (3H, s), 6.79 (1H, d, J=8.8 Hz), 6.92 (1H, d, J=8.4 Hz), 7.16 (1H, s), 7.26 (1H, d, J=8.4 Hz), 7.72 (1H, s), 7.97 (1H, d, J=8.8 Hz); $^{13}$C NMR (125 MHz, CDCl3): δ 56.0 (3×C), 60.9, 61.7, 107.4, 108.9, 109.8, 111.3, 118.6, 118.8, 121.0, 123.2, 127.8, 135.0, 141.9, 149.2, 149.7, 152.9, 155.6. IR (KBr) 3005, 2940, 2214, 1599, 1520 cm$^{-1}$. EIMS m/z (rel int) 355 (100, M$^+$). Anal. Calcd for C$_{20}$H$_{21}$NO$_5$: C, 67.59; H, 5.96; N, 3.94. Found: C, 67.43; H, 5.80; N, 4.00.

(Z)-2-(3,4-Dimethoxyphenyl)-3-(4-methoxyphenyl)acrylonitrile (17b)

Yield 90%; pale yellow granule, mp 129-130° C. (hexane-CHCl$_3$) (S. Yamashita, N. Kurono, H. Senboku, M. Tokuda, K. Orito, Eur. J. Org. Chem. 2009, 8, 1173-1180; mp 128-130° C.).
$^1$H NMR (500 MHz, CDCl$_3$): δ 3.87 (3H, s), 3.92 (3H, s), 3.96 (3H, s), 6.91 (1H, d, J=8.5 Hz), 6.97 (2H, d, J=8.6 Hz), 7.13 (1H, s), 7.23 (1H, s), 7.36 (1H, s), 7.86 (2H, d, J=8.6 Hz); $^{13}$C NMR (125 MHz, CDCl$_3$): δ 55.4, 56.0 (2×C), 108.4, 108.7, 111.3, 114.3 (2×C), 118.7, 126.6, 127.7, 130.9 (2×C), 140.1, 149.2, 149.7, 161.1. IR (KBr) 3004, 2968, 2210, 1603, 1514 cm$^{-1}$. EIMS m/z (rel int) 295 (100, M$^+$). Anal. Calcd for C$_{18}$H$_{17}$NO$_3$: C, 73.20; H, 5.80; N, 4.74. Found: C, 73.40; H, 6.08; N, 4.36.

(Z)-2-(3,4-Dimethoxyphenyl)-3-(3-methoxyphenyl)acrylonitrile (17c)

Yield 92%; pale yellow plate, mp 113-114° C. (hexane-EtOAc).
$^1$H NMR (500 MHz, CDCl$_3$): δ 3.87 (3H, s), 3.92 (3H, s), 3.96 (3H, s), 6.91 (1H, d, J=8.3 Hz), 6.97 (1H, d, J=7.7 Hz), 7.14 (1H, s), 7.26 (1H, d, J=8.3 Hz), 7.35 (1H, d, J=7.7 Hz), 7.40 (2H, br s), 7.47 (1H, s); $^{13}$C NMR (125 MHz, CDCl$_3$): δ 55.3, 56.0 (2×C), 108.8, 111.3, 111.5, 113.4, 116.5, 118.1, 119.1, 121.9, 127.2, 129.8, 135.1, 140.3, 149.3, 150.1, 159.8. IR (KBr) 3005, 2940, 2835, 2218, 1597, 1516 cm$^{-1}$. EIMS m/z (rel int) 295 (100, M$^+$). HREIMS m/z calcd for C$_{18}$H$_{17}$NO$_3$: 295.1208; found: 295.1203 [M]$^+$. Anal. Calcd for C$_{18}$H$_{17}$NO$_3$: C, 73.20; H, 5.80; N, 4.74. Found: C, 73.08; H, 5.46; N, 4.65.

(Z)-3-(3,4,5-Trimethoxyphenyl)-2-(3,4-dimethoxyphenyl)acrylonitrile (17d). Yield 95%; yellow needle, mp 159-160° C. (hexane-EtOAc) (J. W. Clark-Lewis, J. Chem. Soc. 1960, 2433-2436; mp 169-170° C.).
$^1$H NMR (500 MHz, CDCl$_3$): δ 3.93 (12H, s), 3.97 (3H, s), 6.92 (1H, d, J=8.3 Hz), 7.14 (1H, s), 7.17 (2H, s), 7.25 (1H, d, J=8.3 Hz), 7.34 (1H, s); $^{13}$C NMR (125 MHz, CDCl$_3$): δ 56.0, 56.1, 56.2 (2×C), 61.0, 106.5 (2×C), 108.7, 110.3, 111.3, 118.4, 119.0, 127.3, 129.2, 139.9, 140.3, 149.3, 150.0, 153.2 (2×C). IR (KBr) 3084, 2949, 2220, 1582, 1517 cm$^{-1}$. EIMS m/z (rel int) 355 (100, M$^+$). Anal. Calcd for C$_{20}$H$_{21}$NO$_5$: C, 67.59; H, 5.96; N, 3.94. Found: C, 67.30; H, 6.11; N, 3.79.

(Z)-2-(3,4,5-Trimethoxyphenyl)-3-(3,4-dimethoxyphenyl)acrylonitrile (17e). Yield 90%; pale yellow needle, mp 137-138° C. (hexane-EtOAc).
$^1$H NMR (500 MHz, CDCl$_3$): δ 3.89 (3H, s), 3.94 (6H, s), 3.95 (3H, s), 3.97 (3H, s), 6.85 (2H, s), 6.93 (1H, d, J=8.5 Hz), 7.37 (1H, dd, J=8.5, 1.8 Hz), 7.38 (1H, s), 7.67 (1H, d, J=1.8 Hz); $^{13}$C NMR (125 MHz, CDCl3): δ 55.9, 56.0, 56.3 (2×C), 60.9, 103.2 (2×C), 108.6, 110.8, 110.9, 118.6, 124.1, 126.6, 130.4, 138.8, 141.6, 149.0, 151.1, 153.5 (2×C). IR (KBr) 3007, 2943, 2212, 1585, 1518 cm$^{-1}$. EIMS m/z (rel int) 355 (100, M$^+$). Anal. Calcd for C$_{20}$H$_{21}$NO$_5$: C, 67.59; H, 5.96; N, 3.94. Found: C, 67.57; H, 5.96; N, 3.90.

(Z)-3-(3,4-Dimethoxyphenyl)-2-(3-methoxyphenyl)acrylonitrile (17f)

Yield 94%; yellow plate, mp 107-108° C. (hexane-EtOAc).
$^1$H NMR (500 MHz, CDCl$_3$): δ 3.87 (3H, s), 3.95 (3H, s), 3.97 (3H, s), 6.92 (1H, d, J=8.5 Hz), 6.93 (1H, d, J=8.5 Hz), 7.17 (1H, s), 7.25 (1H, d, J=8.5 Hz), 7.32-7.38 (2H, m), 7.45 (1H, s), 7.71 (11H, s); $^{13}$C NMR (125 MHz, CDCl$_3$): δ 55.3, 55.9 (2×C), 108.5, 110.8, 110.9, 111.4, 114.2, 118.2, 118.6, 124.4, 126.6, 130.0, 136.2, 142.3, 149.0, 151.1, 160.0. IR (KBr) 3017, 2951, 2832, 2207, 1593, 1512 cm$^{-1}$. EIMS m/z (rel int) 295 (100, M$^+$). HREIMS m/z calcd for C$_{18}$H$_{17}$NO$_3$: 295.1208; found: 295.1207 [M]$^+$. Anal. Calcd for C$_{18}$H$_{17}$NO$_3$: C, 73.20; H, 5.80; N, 4.74. Found: C, 73.04; H, 5.46; N, 4.66.

(Z)-3-(3,4-Dimethoxyphenyl)-2-(4-methoxyphenyl)acrylonitrile (17g)

Yield 88%; pale yellow granule, mp 109-110° C. (hexane-EtOAc) (T. H. Chuang, W. Y. Chang, C. F. Li, Y. C. Wen, C.

C. Tsai, J. Org. Chem. 2011, 76, 9678-9686; mp 109-110° C.). 1H NMR (500 MHz, CDCl3): δ 3.84 (3H, s), 3.93 (3H, s), 3.96 (3H, s), 6.91 (1H, d, J=8.4 Hz), 6.95 (2H, d, J=8.8 Hz), 7.31-7.34 (2H, m), 7.58 (2H, d, J=8.7 Hz), 7.67 (1H, s); 13C NMR (125 MHz, CDCl3): δ 55.4, 55.9, 56.0, 108.3, 110.6, 110.9, 114.4 (2×C), 118.7, 123.9, 126.9, 127.0 (2×C), 127.3, 140.1, 149.0, 150.8, 160.1. IR (KBr) 3046, 2998, 2210, 1604, 1515 cm$^{-1}$. EIMS m/z (rel int) 295 (100, M$^+$). Anal. Calcd for $C_{18}H_{17}NO_3$: C, 73.20; H, 5.80; N, 4.74. Found: C, 73.40; H, 5.70; N, 4.50.

(Z)-2-(2,3,4-Trimethoxyphenyl)-3-(3,4-dimethoxyphenyl)acrylonitrile (17h). Yield 67%; pale yellow needle, mp 134-135° C.

$^1$H NMR (500 MHz, CDCl$_3$): δ 3.89 (3H, s), 3.90 (3H, s), 3.94 (3H, s), 3.97 (3H, s), 3.99 (3H, s), 6.70 (1H, d, J=8.7 Hz), 6.91 (1H, d, J=8.5 Hz), 7.11 (1H, d, J=8.7 Hz), 7.29 (1H, s), 7.31 (1H, dd, J=8.5, 1.8 Hz), 7.72 (1H, d, J=1.8 Hz); $^{13}$C NMR (125 MHz, CDCl3): δ 55.9, 56.0 (2×C), 60.8, 60.9, 105.4, 107.4, 110.7, 110.9, 119.0, 123.0, 123.8, 124.1, 127.1, 142.4, 144.8, 149.0, 150.8, 151.6, 154.5. IR (KBr) 3140, 2938, 2214, 1596, 1520 cm$^{-1}$. EIMS m/z (rel int) 355 (100, M$^+$). Anal. Calcd for $C_{20}H_{21}NO_5$: C, 67.59; H, 5.96; N, 3.94. Found: C, 67.28; H, 6.01; N, 3.76.

(Z)-2,3-Bis(3,4-dimethoxyphenyl)acrylonitrile (17i)

Yield 97%; bright yellow granule, mp 155-156° C. (hexane-EtOAc) (T. H. Chuang, W. Y. Chang, C. F. Li, Y. C. Wen, C. C. Tsai, J. Org. Chem. 2011, 76, 9678-9686; mp 155-156° C.). $^1$H NMR (500 MHz, CDCl$_3$): δ 3.93 (3H, s), 3.94 (3H, s), 3.96 (3H, s), 3.97 (3H, s), 6.91 (1H, d, J=8.4 Hz), 6.92 (1H, d, J=8.4 Hz), 7.13 (1H, s), 7.23 (1H, d, J=8.4 Hz), 7.34-7.35 (2H, m), 7.67 (1H, s); $^{13}$C NMR (125 MHz, CDCl$_3$): δ 55.93, 55.95, 55.98, 56.0, 108.5, 108.6, 110.7, 110.9, 111.3, 118.7 (2×C), 123.9, 126.8, 127.6, 140.4, 149.0, 149.2, 149.7, 150.8. IR (KBr) 3000, 2940, 2837, 2209, 1591, 1522 cm$^{-1}$. EIMS m/z (rel int) 325 (100, M$^+$). Anal. Calcd for $C_{19}H_{19}NO_4$: C, 70.14; H, 5.85; N, 4.31. Found: C, 70.24; H, 5.76; N, 4.55.

2. Synthesis of (E)-2,3-diphenylacrylaldehydes 16a-i

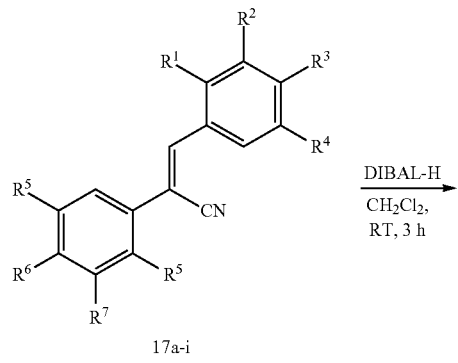

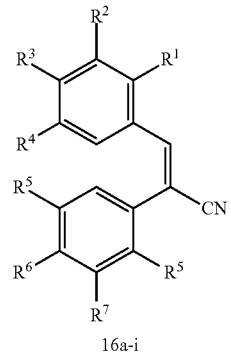

16a: R$^1$ = R$^2$ = R$^3$ = R$^6$ = R$^7$ = OCH$_3$; others = H
16b: R$^3$ = R$^6$ = R$^7$ = OCH$_3$; others = H
16c: R$^2$ = R$^6$ = R$^7$ = OCH$_3$; others = H
16d: R$^2$ = R$^3$ = R$^4$ = R$^6$ = R$^7$ = OCH$_3$; others = H
16e: R$^2$ = R$^3$ = R$^5$ = R$^6$ = R$^7$ = OCH$_3$; others = H
16f: R$^2$ = R$^3$ = R$^7$ = OCH$_3$; others = H
16g: R$^2$ = R$^3$ = R$^6$ = OCH$_3$; others = H
16h: R$^2$ = R$^3$ = R$^6$ = R$^7$ = R$^5$ = OCH$_3$; others = H
16i: R$^2$ = R$^3$ = R$^6$ = R$^7$ = OCH$_3$; others = H Typical procedure for the synthesis of (E)-2,3-diphenylacrylaldehydes 16 according to the literature. [T. H. Chuang, W. Y. Chang, C. F. Li, Y. C. Wen, C. C. Tsai, J. Org. Chem. 2011, 76, 9678-9686] A solution of DIBAL-H (1.1 M in cyclohexane, 6.4 mL, 7 mmol) was added to a solution of (Z)-2,3-diphenylacrylonitriles 17a-i (5 mmol) in CH$_2$Cl$_2$ (50 ml), and the mixture was stirred at −78° C. for 30 min. The mixture was warmed to RT and stirred for 3 h. The resulting solution was quenched with 10% HCl solution (30 mL), and the mixture was stirred for 30 min. The H$_2$O layer was extracted with CH$_2$Cl$_2$ (3×50 mL) and the combined extract was washed with H$_2$O (3×30 mL), dried over anhydrous MgSO$_4$, and filtered. The filtrate was concentrated and the residue was purified by column chromatography over silica gel by eluting with a mixture of hexane/EtOAc (3:1 v/v), affording pure E-(2,3)-diphenylacrylaldehyde (E)-16a-j as the major product. The complete spectral data of these compounds are given below.

(E)-3-(2,3,4-Trimethoxyphenyl)-2-(3,4-dimethoxyphenyl)acrylaldehyde (16a)

Yield 69%; white needle, mp 89-90° C. (hexane-EtOAc).
$^1$H NMR (500 MHz, CDCl$_3$): δ 3.80 (3H, s), 3.82 (3H, s), 3.88 (3H, s), 3.91 (3H, s), 4.01 (3H, s), 6.40 (1H, d, J=9.0 Hz), 6.70 (1H, d, J=1.8 Hz), 6.72 (1H, d, J=9.0 Hz), 6.77 (1H, dd, J=8.2, 1.8 Hz), 6.92 (1H, d, J=8.2 Hz), 7.67 (1H, s), 9.75 (1H, s); $^{13}$C NMR (125 MHz, CDCl3): δ 55.8 (3×C), 60.8, 61.7, 106.9, 111.5, 112.4, 120.8, 121.8, 125.6, 126.1, 140.0, 141.8, 144.2, 148.7, 149.1, 153.5, 155.2, 194.2. IR (KBr) 3005, 2944, 2839, 2730, 1687, 1578, 1515 cm$^{-1}$. EIMS m/z (rel int) 358 (75, M$^+$), 327 (100). Anal. Calcd for $C_{20}H_{22}O_6$: C, 67.03; H, 6.19. Found: C, 67.31; H, 6.55.

(E)-2-(3,4-Dimethoxyphenyl)-3-(4-methoxyphenyl)acrylaldehyde (16b)

Yield 75%; yellow needle, mp 114-115° C. (hexane-EtOAc) (P. A. Grieco, D. T. Parker, J. Org. Chem. 1988, 53, 3325-3330; mp 110-112° C.).
$^1$H NMR (500 MHz, CDCl$_3$): δ 3.80 (3H, s), 3.81 (3H, s), 3.93 (3H, s), 6.70 (1H, d, J=1.0 Hz), 6.76-6.79 (3H, m), 6.94 (1H, d, J=8.2 Hz), 7.21 (2H, d, J=8.8 Hz), 7.30 (1H, s), 9.71

(1H, s); ¹³C NMR (125 MHz, CDCl₃): δ 55.3, 55.8, 55.9, 111.7, 112.3, 114.0 (2×C), 121.8, 126.1, 126.8, 132.7 (2×C), 139.5, 148.9, 149.3, 150.0, 161.2, 194.1. IR (KBr) 3094, 2944, 2827, 2705, 1669, 1585, 1506 cm⁻¹. EIMS m/z (rel int) 298 (100, M⁺). Anal. Calcd for $C_{18}H_{18}O_4$: C, 72.47; H, 6.08. Found: C, 72.45; H, 6.25.

(E)-2-(3,4-Dimethoxyphenyl)-3-(3-methoxyphenyl) acrylaldehyde (16c)

Yield 64%; white needle, mp 94-95° C. (hexane-EtOAc).
¹H NMR (500 MHz, CDCl₃): δ 3.59 (3H, s), 3.79 (3H, s), 3.90 (3H, s), 6.71 (1H, s), 6.78 (1H, s), 6.79 (1H, d, J=8.0 Hz), 6.85 (1H, d, J=8.0 Hz), 6.87 (1H, d, J=8.0 Hz), 6.93 (1H, d, J=8.0 Hz), 7.17 (1H, t, J=8.0 Hz), 7.33 (1H, s), 9.75 (1H, s); ¹³C NMR (125 MHz, CDCl₃): δ 54.9, 55.8 (2×C), 111.5, 112.4, 114.9, 116.6, 121.9, 123.6, 125.6, 129.4, 135.3, 141.6, 149.0, 149.2, 149.8, 159.3, 194.1. IR (KBr) 3036, 2962, 2835, 2712, 1674, 1628, 1597, 1516 cm⁻¹. EMS m/z (rel int) 298 (100, M⁺). HREIMS m/z calcd for $C_{18}H_{18}O_4$: 298.1205; found: 298.1201. Anal. Calcd for $C_{18}H_{18}O_4$: C, 72.47; H, 6.08. Found: C, 72.41; H, 6.07.

(E)-3-(3,4,5-Trimethoxyphenyl)-2-(3,4-dimethoxyphenyl)acrylaldehyde (16d)

Yield 75%; yellow syrup.
¹H NMR (500 MHz, CDCl₃): δ 3.62 (6H, s), 3.82 (3H, s), 3.85 (3H, s), 3.90 (3H, s), 6.54 (2H, s), 6.74 (1H, s), 6.81 (1H, d, J=8.1 Hz), 6.96 (1H, d, J=8.1 Hz), 7.28 (1H, s), 9.74 (1H, s); ¹³C NMR (125 MHz, CDCl₃): δ 55.8 (2×C), 55.9, 56.0, 60.9, 108.3 (2×C), 111.7, 112.5, 122.0, 126.0, 129.2, 140.0, 140.8, 149.1, 149.5, 149.9, 152.8 (2×C), 193.9. IR (KB) 3009, 2938, 2833, 2712, 1678, 1576, 1514 cm⁻¹. EIMS m/z (rel int) 358 (100, M⁺). Anal. Calcd for $C_{20}H_{22}O_6$: C, 67.03; H, 6.19. Found: C, 66.79; H, 5.90.

(E)-2-(3,4,5-Trimethoxyphenyl)-3-(3,4-dimethoxyphenyl)acrylaldehyde (16e)

Yield 70%; white needle, mp 133-134° C. (hexane-EtOAc).
¹H NMR (500 MHz, CDCl₃): δ 3.52 (3H, s), 3.81 (6H, s), 3.87 (3H, s), 3.89 (3H, s), 6.44 (2H, s), 6.69 (1H, s), 6.81 (1H, d, J=8.2 Hz), 6.99 (1H, d, J=8.2 Hz), 7.31 (1H, s), 9.71 (1H, s); ¹³C NMR (125 MHz, CDCl₃): δ 55.2, 55.8, 56.1 (2×C), 60.7, 106.3 (2×C), 110.7, 112.3, 126.2, 126.7, 129.5, 137.8, 139.8, 148.5, 150.3, 151.2, 153.9 (2×C), 193.6. IR (KBr) 3001, 2940, 2833, 2733, 1672, 1582, 1512 cm⁻¹. EIMS m/z (rel int) 358 (100, M⁺). Anal. Calcd for $C_{20}H_{22}O_6$: C, 67.03; H, 6.19. Found: C, 66.90; H, 6.49.

(E)-3-(3,4-Dimethoxyphenyl)-2-(3-methoxyphenyl) acrylaldehyde (16f)

Yield 84%; pale yellow needle, mp 90-92° C. (hexane-EtOAc).
¹H NMR (500 MHz, CDCl₃): δ 3.45 (3H, s), 3.77 (3H, s), 3.86 (3H, s), 6.66 (1H, s), 6.76 (1H, s), 6.78 (1H, d, J=8.0 Hz), 6.81 (1H, d, J=8.0 Hz), 6.91 (1H, d, J=8.0 Hz), 6.97 (1H, d, J=8.0 Hz), 7.30 (1H, s), 7.35 (1H, t, J=8.0 Hz), 9.71 (1H, s); ¹³C NMR (125 MHz, CDCl₃): δ 55.1, 55.2, 55.8, 110.6, 111.7, 112.4, 113.9, 114.7, 121.7, 126.0, 126.8, 130.0, 135.4, 139.7, 148.4, 149.9, 151.0, 160.1, 193.4. IR (KBr) 3082, 2959, 2835, 2723, 1677, 1620, 1582, 1516 cm⁻¹. EIMS m/z (rel int) 298 (45, M⁺), 137 (100). HREIMS m/z calcd for $C_{18}H_{18}O_4$: 298.12058; found: 295.1210 [M]⁺. Anal. Calcd for $C_{18}H_{18}O_4$: C, 72.47; H, 6.08. Found: C, 72.19; H, 6.25.

(E)-3-(3,4-Dimethoxyphenyl)-2-(4-methoxyphenyl) acrylaldehyde (16g)

Yield 70%; pale yellow granule, mp 101-102° C. (hexane-EtOAc) (T. H. Chuang, W. Y. Chang, C. F. Li, Y. C. Wen, C. C. Tsai, J. Org. Chem. 2011, 76, 9678-9686; mp 101-102° C.).
¹H NMR (500 MHz, CDCl₃): δ 3.50 (3H, s), 3.83 (3H, s), 3.88 (3H, s), 6.70 (1H, s), 6.79 (1H, d, J=8.4 Hz), 6.97-6.99 (3H, m), 7.16 (2H, d, J=8.4 Hz), 7.29 (1H, s), 9.72 (1H, s); ¹³C NMR (125 MHz, CDCl₃): δ 55.2, 55.3, 55.8, 110.6, 112.4, 114.4 (2×C), 125.7, 125.8, 127.1, 130.8 (2×C), 139.5, 148.3, 150.1, 150.9, 159.5, 194.0. IR (KBr) 3056, 2997, 2840, 1666, 1600, 1515 cm⁻¹. EIMS m/z (rel int) 298 (100, M⁺). Anal. Calcd for $C_{18}H_{18}O_4$: C, 72.47; H, 6.08. Found: C, 72.14; H, 6.10.

(E)-2-(2,3,4-Trimethoxyphenyl)-3-(3,4-dimethoxyphenyl)acrylaldehyde (16h). Yield 60%; yellow syrup.

¹H NMR (500 MHz, CDCl₃): δ 3.52 (3H, s), 3.73 (3H, s), 3.86 (3H, s), 3.89 (6H, s), 6.69 (1H, s), 6.73-6.82 (3H, m), 6.97 (1H, d, J=7.6 Hz), 7.39 (1H, s), 9.72 (1H, s); ¹³C NMR (125 MHz, CDCl₃): δ 55.2, 55.9, 56.1, 60.9, 61.0, 108.1, 110.7, 112.1, 121.0, 124.9, 125.7, 127.3, 136.9, 142.8, 148.5, 150.4, 151.0, 151.7, 154.1, 193.9. IR (KBr) 3005, 2938, 2837, 2710, 1678, 1595, 1514 cm⁻¹. EIMS m/z (rel int) 358 (100, M⁺). Anal. Calcd for $C_{20}H_{22}O_6$: C, 67.03; H, 6.19. Found: C, 66.73; H, 5.95.

(E)-2,3-Bis(3,4-dimethoxyphenyl)acrylaldehyde (16I)

Yield 91%; yellow syrup.
¹H NMR (500 MHz, CDCl₃): δ 3.52 (3H, s), 3.82 (3H, s), 3.88 (3H, s), 3.91 (3H, s), 6.73-6.82 (4H, m), 6.95-6.98 (2H, m), 7.30 (1H, s), 9.72 (1H, s); ¹³C NMR (125 MHz, CDCl₃): δ 55.3, 55.8, 55.9, 56.0, 110.6, 111.7, 112.5 (2×C), 121.9, 125.7, 126.2, 126.9, 139.6, 148.4, 148.9, 149.4, 150.1, 151.0, 193.9. IR (KBr) 3005, 2938, 2837, 2710, 1678, 1595, 1514 cm⁻¹. EIMS m/z (rel int) 358 (100, M⁺). Anal. Calcd for $C_{20}H_{22}O_6$: C, 67.03; H, 6.19. Found: C, 66.73; H, 5.95.

3. Synthesis of α-iminonitriles 14a-i and 15a-i

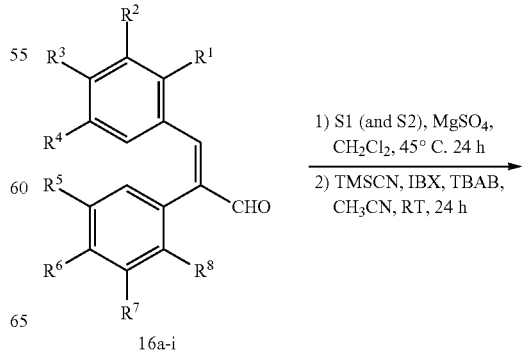

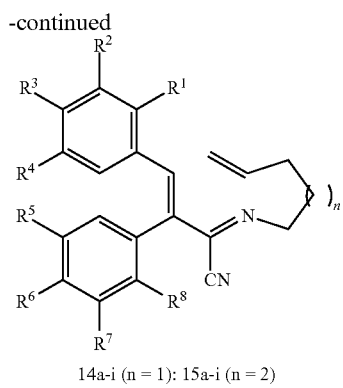

14a-i (n = 1): 15a-i (n = 2)

a: $R^1 = R^2 = R^3 = R^6 = R^7 = OCH_3$
b: $R^3 = R^6 = R^7 = OCH_3$
c: $R^2 = R^6 = R^7 = OCH_3$
d: $R^2 = R^3 = R^4 = R^6 = R^7 = OCH_3$
e: $R^2 = R^3 = R^5 = R^6 = R^7 = OCH_3$
f: $R^2 = R^3 = R^7 = OCH_3$
g: $R^2 = R^3 = R^6 = OCH_3$
h: $R^2 = R^3 = R^6 = R^7 = R^8 = OCH_3$
i: $R^2 = R^3 = R^6 = R^7 = OCH_3$

Typical procedure for the synthesis of α-iminonitriles 14a-i and 15a-i. A suspension of (E)-2,3-diphenylacrylaldehydes (E)-16a-i (2 mmol), pent-4-enylamine (S1) (4 mmol) (J. Y. Kim, T. Livinghouse, Org. Lett. 2005, 7, 1737-1739) (or hex-5-enylamine (S2) (Z. K. M. A. E. Samii, M. I. A. Ashmawy, J. M. Mellor, J. Chem. Soc., Perkin Trans. 1 1988, 2517-2522), and MgSO$_4$ (3 mmol) in anhydrous CH$_2$Cl$_2$ (8 mL) in a sealed tube was heated at 45° C. for 24 h. After cooling, the reaction mixture was filtered and concentrated under reduced pressure, affording the Schiff base intermediate quantitatively. Then, TMSCN (2.2 mmol) was added to a solution of the Schiff base in anhydrous CH$_3$CN (8 mL) at RT, and the mixture was stirred for 1 h. IBX [M. Frigerio, M. Santagostino, S. Sputore, J. Org. Chem. 1999, 64, 4537-4538] (2.2 mmol) and TBAB (2.2 mmol) were added and stirred for 30 min. The solvent was evaporated in vacuo and the residue was purified by short column chromatography over silica gel by eluting with a mixture of hexane/EtOAc (4:1 v/v), affording pure (3E)-2-(4-pentenylimino)-3,4-diphenyl-3-butenenitrile 14a-i (or (3E)-2-(5-hexenylimino)-3,4-diphenyl-3-butenenitrile 15a-i). The complete spectral data of these compounds are given below.

(3E)-4-(2,3,4-Trimethoxyphenyl)-3-(3,4-dimethoxyphenyl)-2-(4-pentenylimino)-3-butenenitrile (14a)

Yield 80%; yellow syrup.
$^1$H NMR (500 MHz, CDCl$_3$): δ 1.79 (2H, quintet, J=7.2 Hz), 2.13 (2H, q, J=7.2 Hz), 3.77 (3H, s), 3.79 (3H, s), 3.87 (3H, s), 3.89 (2H, t, J=7.2 Hz), 3.91 (3H, s), 3.99 (3H, s), 4.99 (1H, dd, J=10.2, 1.8 Hz), 5.03 (1H, dd, J=17.1, 1.8 Hz), 5.81 (1H, ddt, J=17.1, 10.2, 7.2 Hz), 6.34 (1H, d, J=8.9 Hz), 6.41 (1H, d, J=8.9 Hz), 6.66 (1H, d, J=1.9 Hz), 6.71 (1H, dd, J=8.2, 1.9 Hz), 6.88 (1H, d, J=8.2 Hz), 7.79 (1H, s); $^{13}$C NMR (125 MHz, CDCl$_3$): δ 29.6, 31.5, 55.8, 55.9, 56.0, 58.2, 60.9, 61.6, 107.0, 109.7, 111.3, 113.2, 115.2, 121.8, 122.5, 125.2, 127.8, 134.2, 136.6, 137.8, 141.9, 145.4, 148.8, 149.0, 153.4, 154.5. IR (KBr) 3021, 2940, 2216, 1576, 1516 cm$^{-1}$. EIMS m/z (rel int) 450 (60, M$^+$), 417 (100); HREIMS m/z calcd for C$_{26}$H$_{30}$N$_2$O$_5$: 450.2155; found: 450.2158 [M]$^+$.

(3E)-3-(3,4-Dimethoxyphenyl)-4-(4-methoxyphenyl)-2-(4-pentenylimino)-3-butenenitrile (14b)

Yield 78%; yellow syrup.
$^1$H NMR (500 MHz, CDCl$_3$): δ 1.78 (2H, quintet, J=7.0 Hz), 2.12 (2H, q, J=7.0 Hz), 3.77 (3H, s), 3.78 (3H, s), 3.89 (2H, t, J=7.0 Hz), 3.92 (3H, s), 4.98 (1H, d, J=10.2 Hz), 5.02 (1H, d, J=17.0 Hz), 5.81 (1H, ddt, J=17.0, 10.2, 7.0 Hz), 6.66 (1H, d, J=1.4 Hz), 6.71 (2H, d, J=8.7 Hz), 6.72 (1H, dd, J=8.2, 1.4 Hz), 6.90 (1H, d, J=8.2 Hz), 7.00 (2H, d, J=8.7 Hz), 7.46 (1H, s); $^{13}$C NMR (125 MHz, CDCl$_3$): δ 29.6, 31.4, 55.2, 55.7, 55.8, 58.2, 109.7, 111.5, 113.0 (2×C), 113.8, 115.2, 122.4, 127.4, 127.6, 132.2 (2×C), 135.9, 137.8, 139.6, 145.1, 148.8, 149.2, 160.2. IR (KBr) 3075, 2936, 2214, 1605, 1574, 1512 cm$^{-1}$. EIMS m/z (rel int) 390 (100, M$^+$); HREIMS m/z calcd for C$_{24}$H$_{26}$N$_2$O$_3$: 390.1943; found: 390.1941 [M]$^+$.

(3E)-3-(3,4-Dimethoxyphenyl)-4-(3-methoxyphenyl)-2-(4-pentenylimino)-3-butenenitrile (14c)

Yield 81%; yellow syrup.
$^1$H NMR (500 MHz, CDCl$_3$): δ 1.80 (2H, quintet, J=7.0 Hz), 2.12 (2H, q, J=7.0 Hz), 3.57 (3H, s), 3.76 (3H, s), 3.90 (3H, s), 3.91 (2H, t, J=7.0 Hz), 4.99 (1H, dd, J=10.2, 1.7 Hz), 5.03 (1H, dd, J=17.0, 1.7 Hz), 5.81 (1H, ddt, J=17.0, 10.2, 7.0 Hz), 6.58 (1H, t, J=1.9 Hz), 6.67 (1H, d, J=1.9 Hz), 6.71 (1H, dd, J=8.0, 1.9 Hz), 6.73 (1H, dd, J=8.0, 1.9 Hz), 6.77 (1H, dd, J=8.0, 1.9 Hz), 6.89 (1H, d, J=8.0 Hz), 7.11 (1H, t, J=8.0 Hz), 7.49 (1H, s); $^{13}$C NMR (125 MHz, CDCl$_3$): δ 29.5, 31.4, 54.9, 55.8, 55.9, 58.4, 109.6, 111.4, 113.2, 114.7, 115.3, 115.6, 122.5, 123.3, 127.3, 129.2, 136.0, 137.7, 138.1, 139.7, 145.0, 149.0, 149.2, 159.2. IR (KBr) 3075, 2924, 2214, 1578, 1516 cm$^{-1}$. EIMS m/z (rel int) 390 (95, M$^+$), 165 (100); HREIMS m/z calcd for C$_{24}$H$_{26}$N$_2$O$_3$: 390.1943; found: 390.1948 [M]$^+$.

(3E)-4-(3,4,5-Trimethoxyphenyl)-3-(3,4-dimethoxyphenyl)-2-(4-pentenylimino)-3-butenenitrile (14d)

Yield 80%; yellow syrup.
$^1$H NMR (500 MHz, CDCl$_3$): δ 1.79 (2H, quintet, J=7.02 Hz), 2.12 (2H, q, J=7.0 Hz), 3.59 (6H, s), 3.80 (3H, s), 3.82 (3H, s), 3.89 (3H, s), 3.91 (2H, t, J=7.0 Hz), 4.99 (1H, dd, J=10.2, 1.2 Hz), 5.03 (1H, dd, J=17.1, 1.2 Hz), 5.81 (1H, ddt, J=17.1, 10.2, 7.0 Hz), 6.34 (2H, s), 6.70 (1H, d, J=1.9 Hz), 6.76 (1H, dd, J=8.2, 1.9 Hz), 6.93 (1H, d, J=8.2 Hz), 7.43 (1H, s); $^{13}$C NMR (125 MHz, CDCl$_3$): δ 29.5, 31.4, 55.8 (2×C), 55.9, 56.0, 58.4, 60.9, 108.0 (2×C), 109.6, 111.6, 113.2, 115.3, 122.5, 127.6, 129.9, 137.3, 137.7, 138.9, 139.8, 145.0, 149.0, 149.4, 152.7 (2×C). IR (KBr) 3022, 2938, 2216, 1578, 1518, 1504 cm$^{-1}$. EIMS m/z (rel int) 450 (53, M$^+$), 419 (100); HREIMS m/z calcd for C$_{26}$H$_{30}$N$_2$O$_5$: 450.2155; found: 450.2157 [M]$^+$.

(3E)-3-(3,4,5-Trimethoxyphenyl)-4-(3,4-dimethoxyphenyl)-2-(4-pentenylimino)-3-butenenitrile (14e)

Yield 86%; yellow syrup.
$^1$H NMR (500 MHz, CDCl$_3$): δ 1.80 (2H, quintet, J=7.2 Hz), 2.13 (2H, q, J=7.2 Hz), 3.51 (3H, s), 3.77 (6H, s), 3.86 (3H, s), 3.87 (3H, s), 3.91 (2H, t, J=7.2 Hz), 4.99 (1H, dd, J=10.2, 1.4 Hz), 5.02 (1H, dd, J=17.1, 1.4 Hz), 5.81 (1H, ddt, J=17.1, 10.2, 7.2 Hz), 6.41 (2H, s), 6.48 (1H, d, J=1.9 Hz), 6.76 (1H, d, J=8.4 Hz), 6.85 (1H, dd, J=8.4, 1.9 Hz), 7.45 (1H, s); $^{13}$C NMR (125 MHz, CDCl$_3$): δ 29.6, 31.5, 55.3, 55.8, 56.2 (2×C), 58.3, 60.8, 107.0 (2×C), 109.6, 110.6, 112.2, 115.2, 125.5, 127.4, 130.9, 136.1, 137.7, 137.8, 139.9, 144.8, 148.3, 150.1, 153.8 (2×C). IR (KBr) 3021, 2938, 2216, 1582, 1514 cm$^{-1}$. EIMS m/z (rel int) 450 (83, M$^+$), 435 (100); HREIMS m/z calcd for C$_{26}$H$_{30}$N$_2$O$_5$: 450.2155; found: 450.2164 [M]$^+$.

(3E)-4-(3,4-Dimethoxyphenyl)-3-(3-methoxyphenyl)-2-(4-pentenylimino)-3-butenenitrile (14o)

Yield 89%; yellow syrup.
$^1$H NMR (500 MHz, CDCl$_3$): δ 1.76 (2H, quintet, J=7.0 Hz), 2.09 (2H, q, J=7.0 Hz), 3.44 (3H, s), 3.76 (3H, s), 3.85 (3H, s), 3.88 (2H, t, J=7.0 Hz), 4.97 (1H, d, J=10.2 Hz), 5.02 (1H, d, J=17.0 Hz), 5.80 (1H, ddt, J=17.0, 10.2, 7.0 Hz), 6.44 (1H, d, J=1.9 Hz), 6.72 (1H, s), 6.74 (1H, d, J=8.6 Hz), 6.78 (1H, d, J=7.9 Hz), 6.84 (1H, dd, J=8.6, 1.9 Hz), 6.91 (1H, d, J=7.9 Hz), 7.34 (1H, t, J=7.9 Hz), 7.46 (1H, s); $^{13}$C NMR (125 MHz, CDCl$_3$): δ 29.5, 31.4, 55.1, 55.2, 55.8, 58.2, 109.6, 110.5, 112.2, 113.8, 115.1, 115.3, 122.3, 125.3, 127.4, 130.0, 136.1, 137.0, 137.8, 139.7, 144.7, 148.2, 150.0, 160.1. IR (KBr) 3075, 2935, 2218, 1597, 1585, 1512 cm$^{-1}$. EIMS m/z (rel int) 390 (100, M$^+$); HREIMS m/z calcd for C$_{24}$H$_{26}$N$_2$O$_3$: 390.1943; found: 390.1940 [M]$^+$.

(3E)-4-(3,4-Dimethoxyphenyl)-3-(4-methoxyphenyl)-2-(4-pentenylimino)-3-butenenitrile (14g)

Yield 76%; yellow syrup.
$^1$H NMR (500 MHz, CDCl$_3$): δ 1.77 (2H, quintet, J=7.2 Hz), 2.10 (2H, q, J=7.2 Hz), 3.48 (3H, s), 3.82 (3H, s), 3.85 (3H, s), 3.88 (2H, t, J=7.2 Hz), 4.98 (1H, d, J=10.2 Hz), 5.02 (1H, d, J=17.2 Hz), 5.81 (1H, ddt, J=17.2, 10.2, 7.2 Hz), 6.45 (1H, d, J=1.8 Hz), 6.74 (1H, d, J=8.4 Hz), 6.81 (1H, dd, J=8.4, 1.8 Hz), 6.95 (2H, d, J=8.7 Hz), 7.10 (2H, d, J=8.7 Hz), 7.45 (1H, s); $^{13}$C NMR (125 MHz, CDCl$_3$): δ 29.6, 31.4, 55.2, 55.3, 55.8, 58.3, 109.8, 110.6, 112.4, 114.4 (2×C), 115.2, 125.1, 127.6, 127.7, 131.4 (2×C), 136.1, 137.8, 139.8, 145.1, 148.3, 149.9, 159.4. IR (KBr) 3009, 2955, 2218, 1639, 1612, 1570, 1508 cm$^{-1}$. EIMS m/z (rel int) 390 (21, M$^+$), 265 (100); HREIMS m/z calcd for C$_{24}$H$_{26}$N$_2$O$_3$: 390.1943; found: 390.1951 [M]+.

(3E)-3-(2,3,4-Trimethoxyphenyl)-4-(3,4-dimethoxyphenyl)-2-(4-pentenylimino)-3-butenenitrile (14h)

Yield 78%; yellow syrup.
$^1$H NMR (500 MHz, CDCl$_3$): δ 1.75 (2H, quintet, J=7.0 Hz), 2.10 (2H, q, J=7.0 Hz), 3.52 (3H, s), 3.72 (3H, s), 3.85 (3H, s), 3.86 (3H, s), 3.87 (3H, s), 3.88 (2H, t, J=7.0 Hz), 4.97 (1H, dd, J=10.2, 1.8 Hz), 5.01 (1H, dd, J=17.1, 1.8 Hz), 5.79 (1H, ddt, J=17.1, 10.2, 7.0 Hz), 6.52 (1H, d, J=1.9 Hz), 6.70-6.76 (3H, m), 6.84 (1H, dd, J=8.4, 1.9 Hz), 7.50 (1H, s); $^{13}$C NMR (125 MHz, CDCl$_3$): δ 29.6, 31.3, 55.2, 55.8, 56.0, 58.1, 60.7, 60.8, 107.8, 109.9, 110.7, 112.0, 115.1, 122.5, 125.0, 125.2, 127.8, 133.3, 137.9, 139.7, 142.7, 144.8, 148.3, 149.9, 151.8, 154.1. IR (KBr) 3030, 2947, 2216, 1533 cm$^{-1}$. EIMS m/z (rel int) 450 (37, M$^+$), 419 (100); HREIMS m/z calcd for C$_{26}$H$_{30}$N$_2$O$_5$: 450.2155; found: 450.2144 [M]$^+$.

(3E)-3,4-Bis(3,4-dimethoxyphenyl)-2-(4-pentenylimino)-3-butenenitrile (14i)

Yield 86%; yellow syrup.
$^1$H NMR (500 MHz, CDCl$_3$): δ 1.78 (2H, quintet, J=7.0 Hz), 2.12 (2H, q, J=7.0 Hz), 3.51 (3H, s), 3.79 (3H, s), 3.86 (3H, s), 3.88 (2H, t, J=7.0 Hz), 3.89 (3H, s), 4.99 (1H, dd, J=10.2, 2.0 Hz), 5.02 (1H, dd, J=17.1, 2.0 Hz), 5.81 (1H, ddt, J=17.1, 10.2, 7.0 Hz), 6.50 (1H, d, J=2.0 Hz), 6.70 (1H, d, J=1.8 Hz), 6.73 (1H, d, J=8.5 Hz), 6.75 (1H, dd, J=8.3, 1.8 Hz), 6.80 (1H, dd, J=8.5, 2.0 Hz), 6.92 (1H, d, J=8.3 Hz), 7.45 (1H, s); $^{13}$C NMR (125 MHz, CDCl$_3$): δ 29.5, 31.4, 55.3, 55.8, 55.9 (2×C), 58.2, 109.7, 110.6, 111.6, 112.5, 113.1, 115.2, 122.5, 125.0, 127.6, 127.8, 136.0, 137.7, 139.8, 145.0, 148.2, 148.8, 149.4, 149.9. IR (KBr) 3001, 2932, 2214, 1574, 1516 cm$^{-1}$. EIMS m/z (rel int) 420 (77, M$^+$), 419 (100); HREIMS m/z calcd for C$_{25}$H$_{28}$N$_2$O$_4$: 420.2049; found: 420.2047 [M]$^+$.

(3E)-2-(5-Hexenylimino)-4-(2,3,4-trimethoxyphenyl)-3-(3,4-dimethoxyphenyl)-3-butenenitrile (15a)

Yield 81%; yellow syrup.
$^1$H NMR (500 MHz, CDCl$_3$): δ 1.46 (2H, quintet, J=7.1 Hz), 1.71 (2H, quintet, J=7.1 Hz), 2.09 (2H, q, J=7.1 Hz), 3.77 (3H, s), 3.79 (3H, s), 3.87 (3H, s), 3.89 (2H, t, J=7.1 Hz), 3.91 (3H, s), 3.99 (3H, s), 4.95 (1H, dd, J=10.1, 1.2 Hz), 5.01 (1H, dd, J=17.1, 1.2 Hz), 5.79 (1H, ddt, J=17.1, 10.1, 7.1 Hz), 6.34 (1H, d, J=8.9 Hz), 6.40 (1H, d, J=8.9 Hz), 6.66 (1H, d, J=1.6 Hz), 6.71 (1H, dd, J=8.2, 1.6 Hz), 6.87 (1H, d, J=8.2 Hz), 7.79 (1H, s); $^{13}$C NMR (125 MHz, CDCl$_3$): δ 26.5, 29.8, 33.3, 55.6, 55.7, 55.8, 58.6, 60.8, 61.5, 106.9, 109.6, 111.3, 113.2, 114.6, 121.7, 122.4, 125.1, 127.7, 134.0, 136.5, 138.3, 141.8, 145.2, 148.7, 149.0, 153.3, 154.4. IR (KBr) 3005, 2938, 2218, 1580, 1516 cm$^{-1}$. EIMS m/z (rel int) 464 (91, M$^+$), 433 (100); HREIMS m/z calcd for C$_{27}$H$_{32}$N$_2$O$_5$: 464.2311; found: 464.2306 [M]$^+$.

(3E)-2-(5-Hexenylimino)-3-(3,4-dimethoxyphenyl)-4-(4-methoxyphenyl)-3-butenenitrile (15b)

Yield 83%; yellow syrup.
$^1$H NMR (500 MHz, CDCl$_3$): δ 1.45 (2H, quintet, J=7.0 Hz), 1.69 (2H, quintet, J=7.0 Hz), 2.08 (2H, q, J=7.0 Hz), 3.76 (3H, s), 3.77 (3H, s), 3.89 (2H, t, J=7.0 Hz), 3.91 (3H, s), 4.95 (1H, d, J=10.2 Hz), 5.00 (1H, d, J=17.0 Hz), 5.79 (1H, ddt, J=17.0, 10.2, 7.0 Hz), 6.66 (1H, d, J=1.5 Hz), 6.70 (2H, d, J=8.8 Hz), 6.71 (1H, dd, J=8.5, 1.5 Hz), 6.89 (1H, d, J=8.5 Hz), 7.00 (2H, d, J=8.8 Hz), 7.46 (1H, s); $^{13}$C NMR (125 MHz, CDCl$_3$): δ 26.5, 29.8, 33.3, 55.2, 55.7, 55.8, 58.7, 109.7, 111.4, 113.0, 113.7 (2×C), 114.6, 122.3, 127.4, 127.6, 132.1 (2×C), 135.9, 138.4, 139.4, 144.9, 148.8, 149.2, 160.1. IR (KBr) 3075, 2936, 2218, 1639, 1605, 1581, 1512 cm$^{-1}$. EIMS m/z (rel int) 404 (100, M$^+$); HREIMS m/z calcd for C$_{25}$H$_{28}$N$_2$O$_3$: 404.2100; found: 404.2107 [M]$^+$.

(3E)-2-(5-Hexenylimino)-3-(3,4-dimethoxyphenyl)-4-(3-methoxyphenyl)-3-butenenitrile (15c)

Yield 83%; yellow syrup.
$^1$H NMR (500 MHz, CDCl$_3$): δ 1.47 (2H, quintet, J=7.2 Hz), 1.71 (2H, quintet, J=7.2 Hz), 2.09 (2H, q, J=7.2 Hz), 3.57 (3H, s), 3.76 (3H, s), 3.90 (3H, s), 3.91 (2H, t, J=7.2 Hz), 4.96 (1H, d, J=10.2 Hz), 5.01 (1H, d, J=17.2 Hz), 5.77 (1H, ddt, J=17.2, 10.2, 7.2 Hz), 6.58 (1H, s), 6.66 (1H, s), 6.70 (1H, d, J=8.0 Hz), 6.72 (1H, d, J=8.0 Hz), 6.77 (1H, d, J=8.0 Hz), 6.89 (1H, d, J=8.0 Hz), 7.11 (1H, t, J=8.0 Hz), 7.48 (1H, s); $^{13}$C NMR (125 MHz, CDCl$_3$): δ 26.6, 29.8, 33.4, 54.9, 55.8, 55.9, 58.9, 109.6, 111.4, 113.2, 114.7, 114.8, 115.6, 122.5, 123.3, 127.3, 129.2, 136.1, 138.1, 138.4, 139.6, 144.8, 149.0, 149.2, 159.2. IR (KBr) 3075, 2932, 2218, 1578, 1516 cm$^{-1}$. EIMS m/z (rel int) 404 (59, M+), 165 (100); HREIMS m/z calcd for C$_{25}$H$_{28}$N$_2$O$_3$: 404.2100; found: 404.2101 [M]+.

(3E)-2-(5-Hexenylimino)-4-(3,4,5-trimethoxyphenyl)-3-(3,4-dimethoxyphenyl)-3-butenenitrile (15d)

Yield 80%; yellow syrup.
$^1$H NMR (500 MHz, CDCl$_3$): δ 1.45 (2H, quintet, J=7.2 Hz), 1.71 (2H, quintet, J=7.2 Hz), 2.09 (2H, q, J=7.2 Hz), 3.59 (6H, s), 3.79 (3H, s), 3.82 (3H, s), 3.89 (3H, s), 3.91 (2H, t, J=7.2 Hz), 4.95 (1H, dd, J=10.2, 1.9 Hz), 5.01 (1H, dd, J=17.1, 1.9 Hz), 5.79 (1H, ddt, J=17.1, 10.2, 7.2 Hz), 6.34 (2H, s), 6.69 (1H, d, J=1.9 Hz), 6.75 (1H, dd, J=8.2, 1.9 Hz), 6.93 (1H, d, J=8.2 Hz), 7.42 (1H, s); $^{13}$C NMR (125 MHz, CDCl$_3$): δ 26.6, 29.8, 33.4, 55.8 (2×C), 55.9, 56.0, 58.9, 60.9, 107.9 (2×C), 109.7, 111.6, 113.2, 114.8, 122.5, 127.6, 130.0, 137.3, 138.4, 138.9, 139.7, 144.8, 149.0, 149.4, 152.7 (2×C). IR (KBr) 3021, 2936, 2218, 1576, 1506 cm$^{-1}$. EIMS m/z (rel int) 464 (100, M+); HREIMS m/z calcd for C$_{27}$H$_{32}$N$_2$O$_5$: 464.2311; found: 464.2307 [M]+.

(3E)-2-(5-Hexenylimino)-3-(3,4,5-trimethoxyphenyl)-4-(3,4-dimethoxyphenyl)-3-butenenitrile (15e)

Yield 82%; yellow syrup.
$^1$H NMR (500 MHz, CDCl$_3$): δ 1.46 (2H, quintet, J=7.0 Hz), 1.71 (2H, quintet, J=7.0 Hz), 2.09 (2H, q, J=7.0 Hz), 3.51 (3H, s), 3.77 (6H, s), 3.87 (6H, s), 3.91 (2H, t, J=7.0 Hz), 4.95 (1H, d, J=10.2 Hz), 5.00 (1H, d, J=17.3 Hz), 5.79 (1H, ddt, J=17.3, 10.2, 7.0 Hz), 6.41 (2H, s), 6.48 (1H, s), 6.76 (1H, d, J=8.4 Hz), 6.84 (1H, d, J=8.4 Hz), 7.45 (1H, s); $^{13}$C NMR (125 MHz, CDCl$_3$): δ 26.6, 29.9, 33.4, 55.3, 55.8, 56.2 (2×C), 58.8, 60.8, 107.0 (2×C), 109.6, 110.6, 112.2, 114.7, 125.2, 127.4, 130.9, 136.1, 137.8, 138.4, 139.8, 144.7, 148.3, 150.1, 153.8 (2×C). IR (KBr) 3005, 2938, 2218, 1570, 1512 cm$^{-1}$. EIMS m/z (rel int) 464 (100, M+); HREIMS m/z calcd for C$_{27}$H$_{32}$N$_2$O$_5$: 464.2311; found: 464.2318 [M]+.

(3E)-2-(5-Hexenylimino)-4-(3,4-dimethoxyphenyl)-3-(3-methoxyphenyl)-3-butenenitrile (15f)

Yield 86%; yellow syrup.
$^1$H NMR (500 MHz, CDCl$_3$): δ 1.43 (2H, quintet, J=7.0 Hz), 1.67 (2H, quintet, J=7.0 Hz), 2.07 (2H, q, J=7.0 Hz), 3.44 (3H, s), 3.76 (3H, s), 3.85 (3H, s), 3.88 (2H, t, J=7.0 Hz), 4.94 (1H, d, J=10.2 Hz), 5.00 (1H, d, J=17.2 Hz), 5.78 (1H, ddt, J=17.2, 10.2, 7.0 Hz), 6.43 (1H, d, J=1.7 Hz), 6.72 (1H, s), 6.74 (1H, d, J=8.4 Hz), 6.78 (1H, d, J=7.9 Hz), 6.84 (1H, dd, J=8.4, 1.7 Hz), 6.91 (1H, d, J=7.9 Hz), 7.35 (1H, t, J=7.9 Hz), 7.46 (1H, s); $^{13}$C NMR (125 MHz, CDCl$_3$): δ 26.5, 29.8, 33.3, 55.2, 55.3, 55.8, 58.8, 109.6, 110.6, 112.4, 113.9, 114.6, 115.4, 122.3, 125.3, 127.5, 130.0, 136.2, 137.1, 138.5, 139.6, 144.6, 148.3, 150.0, 160.1. IR (KBr) 3075, 2936, 2218, 1574, 1512 cm$^{-1}$. EIMS m/z (rel int) 404 (100, M+); HREIMS m/z calcd for C$_{25}$H$_{28}$N$_2$O$_3$: 404.2100; found: 404.2095 [M]+.

(3E)-2-(5-Hexenylimino)-4-(3,4-dimethoxyphenyl)-3-(4-methoxyphenyl)-3-butenenitrile (15g)

Yield 83%; yellow syrup.
$^1$H NMR (500 MHz, CDCl$_3$): δ 1.44 (2H, quintet, J=7.0 Hz), 1.68 (2H, quintet, J=7.0 Hz), 2.08 (2H, q, J=7.0 Hz), 3.47 (3H, s), 3.82 (3H, s), 3.85 (3H, s), 3.88 (2H, t, J=7.0 Hz), 4.95 (1H, d, J=10.1 Hz), 5.00 (1H, d, J=17.3 Hz), 5.79 (1H, ddt, J=17.3, 10.1, 7.0 Hz), 6.45 (1H, s), 6.73 (1H, d, J=8.4 Hz), 6.81 (1H, d, J=8.4 Hz), 6.95 (2H, d, J=7.5 Hz), 7.10 (2H, t, J=7.5 Hz), 7.45 (1H, s); $^{13}$C NMR (125 MHz, CDCl$_3$): δ 26.5, 29.7, 33.3, 55.1, 55.2, 55.7, 58.7, 109.7, 110.5, 112.3, 114.3 (2×C), 1114.76, 125.0, 127.5, 127.7, 131.3 (2×C), 136.0, 138.4, 139.6, 149.9, 148.1, 149.7, 159.3. IR (KBr) 3075, 2932, 2214, 1639, 1609, 1574, 1512 cm$^{-1}$. EIMS m/z (rel int) 404 (100, M+); HREIMS m/z calcd for C$_{25}$H$_{28}$N$_2$O$_3$: 404.2100; found: 404.2103 [M]+.

(3E)-2-(5-Hexenylimino)-3-(2,3,4-trimethoxyphenyl)-4-(3,4-dimethoxyphenyl)-3-butenenitrile (15h)

Yield 75%; yellow syrup.
$^1$H NMR (500 MHz, CDCl$_3$): δ 1.44 (2H, quintet, J=7.3 Hz), 1.67 (2H, quintet, J=7.3 Hz), 2.06 (2H, q, J=7.3 Hz), 3.52 (3H, s), 3.72 (3H, s), 3.84 (3H, s), 3.86 (3H, s), 3.88 (3H, s), 3.89 (2H, t, J=7.3 Hz), 4.94 (1H, dd, J=10.2, 1.3 Hz), 4.99 (1H, dd, J=17.1, 1.3 Hz), 5.78 (1H, ddt, J=17.1, 10.2, 7.3 Hz), 6.52 (1H, d, J=1.9 Hz), 6.69-6.77 (3H, m), 6.84 (1H, dd, J=8.4, 1.9 Hz), 7.50 (1H, s); $^{13}$C NMR (125 MHz, CDCl$_3$): δ 26.5, 29.9, 33.4, 55.2, 55.8, 56.0, 58.7, 60.7, 60.8, 107.8, 109.9, 110.7, 112.0, 114.6, 122.5, 125.0, 125.2, 127.9, 133.2, 138.5, 139.7, 142.7, 144.7, 148.3, 149.9, 151.8, 154.1. IR (KBr) 3019, 2936, 2218, 1578, 1516 cm$^{-1}$. EIMS m/z (rel int) 464 (41, M+), 433 (100); HREIMS m/z calcd for C$_{27}$H$_{32}$N$_2$O$_5$: 464.2311; found: 464.2303 [M]+.

(3E)-2-(5-Hexenylimino)-3,4-bis(3,4-dimethoxyphenyl)-3-butenenitrile (15I)

Yield 85%; yellow syrup.
$^1$H NMR (500 MHz, CDCl$_3$): δ 1.45 (2H, quintet, J=7.2 Hz), 1.70 (2H, quintet, J=7.2 Hz), 2.08 (2H, q, J=7.2 Hz), 3.51 (3H, s), 3.79 (3H, s), 3.85 (3H, s), 3.89 (2H, t, J=7.2 Hz), 3.90 (3H, s), 4.95 (1H, d, J=10.1 Hz), 5.00 (1H, d, J=17.1 Hz), 5.79 (1H, ddt, J=17.1, 10.1, 7.2 Hz), 6.50 (1H, d, J=1.9 Hz), 6.69 (1H, d, J=1.9 Hz), 6.73 (1H, d, J=8.4 Hz), 6.75 (1H, dd, J=8.2, 1.9 Hz), 6.79 (1H, dd, J=8.4, 1.9 Hz), 6.92 (1H, d, J=8.2 Hz), 7.45 (1H, s); $^{13}$C NMR (125 MHz, CDCl$_3$): δ 26.6, 29.8, 33.4, 55.3, 55.8, 55.9 (2×C), 58.8, 109.7, 110.6, 111.6, 112.5, 113.2, 114.7, 122.5, 125.0, 127.6, 127.8, 136.0, 138.4, 139.7, 144.9, 148.3, 148.9, 149.4, 149.9. IR (KBr) 3001, 2936, 2214, 1574, 1516 cm$^{-1}$. EIMS m/z (rel int) 434 (100, M+); HREIMS m/z calcd for C$_{26}$H$_{30}$N$_2$O$_4$: 434.2206; found: 434.2209 [M]+.

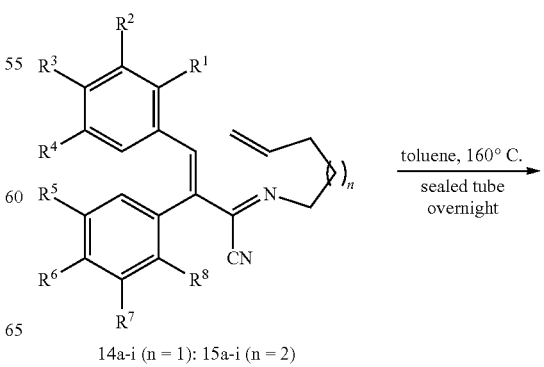

4. Synthesis of cycloadducts 12a-i and trans-13a-i by IADA 14a-i (n = 1); 15a-i (n = 2)

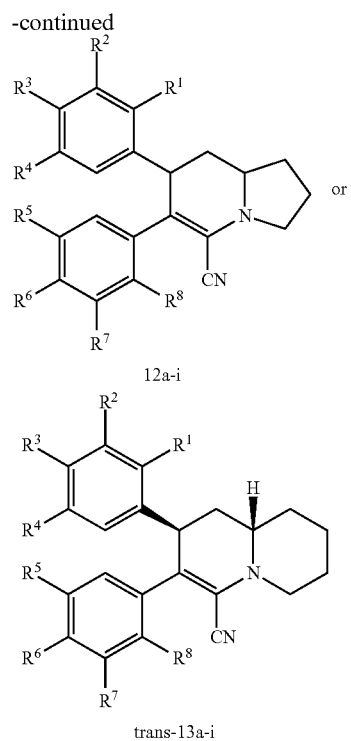

a: $R^1 = R^2 = R^3 = R^6 = R^7 = OCH_3$
b: $R^3 = R^6 = R^7 = OCH_3$
c: $R^2 = R^6 = R^7 = OCH_3$
d: $R^2 = R^3 = R^4 = R^6 = R^7 = OCH_3$
e: $R^2 = R^3 = R^5 = R^6 = R^7 = OCH_3$
f: $R^2 = R^3 = R^7 = OCH_3$
g: $R^2 = R^3 = R^6 = OCH_3$
h: $R^2 = R^3 = R^6 = R^7 = R^8 = OCH_3$
i: $R^2 = R^3 = R^6 = R^7 = OCH_3$

Typical procedure for the synthesis of cycloadducts 12a-i and trans-13a-i by IADA. A 0.05 M solution of α-iminonitriles 14a-i (and 15a-i, 5 mmol) in anhydrous toluene (10 mL) in a sealed tube was heated at 160° C. for overnight. After cooling, the solvent was evaporated in vacuo and the residue was purified by column chromatography over silica gel by eluting with a mixture of hexane/EtOAc (3:1 v/v), affording cycloadducts 12a-i (and trans 13a-i). The complete spectral data of cis-121, trans-12a-i, and trans-13a-i are given below.

trans-7-(2,3,4-Trimethoxyphenyl)-6-(3,4-dimethoxyphenyl)-1,2,3,7,8,8a-hexahydroindolizine-5-carbonitrile (12a)

Yield 60%; yellow syrup.
$^1$H NMR (500 MHz, CDCl$_3$): δ 1.50-1.56 (1H, m), 1.60 (1H, td, J=12.2, 4.2 Hz), 1.83-1.91 (1H, m), 1.91-1.95 (1H, m), 1.96 (1H, d, J=12.2 Hz), 2.10-2.17 (1H, m), 3.23-3.31 (2H, m), 3.68-3.74 (1H, m), 3.79 (3H, s), 3.82 (3H, s), 3.83 (3H, s), 3.84 (3H, s), 3.89 (3H, s), 4.39 (1H, d, J=4.2 Hz), 6.53 (1H, d, J=8.6 Hz), 6.69 (1H, d, J=8.6 Hz), 6.75 (1H, d, J=8.3 Hz), 6.90 (1H, d, J=2.0 Hz), 6.94 (1H, dd, J=8.3, 2.0 Hz); $^{13}$C NMR (125 MHz, CDCl$_3$): δ 24.3, 32.5, 34.5, 37.6, 50.6, 51.9, 55.8, 55.9 (2×C), 60.7, 61.0, 106.5, 110.9, 111.5, 116.6, 117.8, 120.8, 124.0, 125.5, 129.8, 131.4, 142.1, 148.3, 148.4, 151.0, 152.4. IR (KBr) 3015, 2940, 2218, 1597, 1518 cm$^{-1}$. EIMS m/z (rel int) 450 (100, M$^+$); HREIMS m/z calcd for C$_{26}$H$_{30}$N$_2$O$_5$: 450.2155; found: 450.2148 [M]$^+$.

trans-6-(3,4-Dimethoxyphenyl)-7-(4-methoxyphenyl)-1,2,3,7,8,8a-hexahydroindolizine-5-carbonitrile (12b)

Yield 73%; yellow syrup.
$^1$H NMR (500 MHz, CDCl$_3$): δ 1.50-1.56 (1H, m), 1.62 (1H, td, J=12.5, 4.0 Hz), 1.81-1.97 (2H, m), 1.99 (1H, d, J=12.5 Hz), 2.08-2.15 (1H, m), 3.21-3.32 (2H, m), 3.69-3.74 (1H, m), 3.74 (3H, s), 3.81 (3H, s), 3.82 (3H, s), 4.01 (1H, d, J=4.0 Hz), 6.74 (1H, d, J=8.2 Hz), 6.79 (2H, d, J=8.6 Hz), 6.90 (1H, d, J=2.1 Hz), 6.92 (1H, dd, J=8.2, 2.1 Hz), 7.06 (2H, d, J=8.6 Hz); $^{13}$C NMR (125 MHz, CDCl$_3$): δ 24.3, 32.5, 35.6, 43.4, 50.6, 51.6, 55.2, 55.7, 55.9, 110.9, 111.6, 113.8 (2×C), 116.5, 117.4, 120.8, 125.0, 129.2 (2×C), 131.3, 136.5, 148.2, 148.4, 158.1. IR (KBr) 3001, 2932, 2214, 1601, 1512 cm$^{-1}$. EIMS m/z (rel int) 390 (26, M$^+$), 295 (100); HREIMS m/z calcd for C$_{24}$H$_{26}$N$_2$O$_3$: 390.1943; found: 390.1940 [M]$^+$.

trans-6-(3,4-Dimethoxyphenyl)-7-(3-methoxyphenyl)-1,2,3,7,8,8a-hexahydroindolizine-5-carbonitrile (12c)

Yield 78%; yellow syrup.
$^1$H NMR (500 MHz, CDCl$_3$): δ 1.49-1.56 (1H, m), 1.64 (1H, td, J=12.4, 4.0 Hz), 1.81-1.98 (2H, m), 2.04 (1H, d, J=12.4 Hz), 2.08-2.16 (1H, m), 3.23-3.32 (2H, m), 3.68-3.74 (1H, m), 3.76 (3H, s), 3.81 (3H, s), 3.82 (3H, s), 4.03 (1H, d, J=4.0 Hz), 6.68-6.71 (2H, m), 6.73-6.77 (2H, m), 6.89-6.94 (2H, m), 7.17 (1H, t, J=8.0 Hz); $^{13}$C NMR (125 MHz, CDCl$_3$): δ 24.3, 32.6, 35.3, 44.2, 50.6, 51.8, 55.2, 55.8, 55.9, 111.0, 111.3, 111.8, 114.6, 116.5, 117.7, 120.7, 120.8, 124.4, 129.3, 131.4, 146.2, 148.3, 148.5, 159.6. IR (KBr) 3001, 2924, 2218, 1593, 1516 cm$^{-1}$. EIMS m/z (rel int) 390 (100, M$^+$); HREIMS m/z calcd for C$_{24}$H$_{26}$N$_2$O$_3$: 390.1943; found: 390.1937 [M]$^+$.

trans-7-(3,4,5-Trimethoxyphenyl)-6-(3,4-dimethoxyphenyl)-1,2,3,7,8,8a-hexahydroindolizine-5-carbonitrile (12d)

Yield 67%; yellow syrup.
$^1$H NMR (500 MHz, CDCl$_3$): δ 1.50-1.60 (1H, m), 1.63 (1H, td, J=12.0, 5.2 Hz), 1.84-1.99 (2H, m), 2.06 (1H, d, J=12.0 Hz), 2.13-2.20 (1H, m), 3.24-3.31 (2H, m), 3.69-3.75 (1H, m), 3.78 (3H, s), 3.81 (6H, s), 3.83 (6H, s), 4.00 (1H, d, J=5.2 Hz), 6.35 (2H, s), 6.78 (1H, d, J=8.3 Hz), 6.91 (1H, d, J=2.1 Hz), 6.93 (1H, dd, J=8.3, 2.1 Hz); $^{13}$C NMR (125 MHz, CDCl$_3$): δ 24.3, 32.6, 35.6, 44.3, 50.6, 52.0, 55.8, 55.9, 56.2 (2×C), 60.8, 105.5 (2×C), 111.0, 111.7, 116.5, 117.9, 120.9, 124.7, 131.4, 136.5, 140.1, 148.4, 148.5, 153.0 (2×C). IR (KBr) 3019, 2938, 2220, 1591, 1514 cm$^{-1}$. EIMS m/z (rel int) 450 (100, M$^+$); HREIMS m/z calcd for C$_{26}$H$_{20}$N$_2$O$_5$: 450.2155; found: 450.2149 [M]$^+$.

trans-6-(3,4,5-Trimethoxyphenyl)-7-(3,4-dimethoxyphenyl)-1,2,3,7,8,8a-hexahydroindolizine-5-carbonitrile (12e)

Yield 62%; yellow syrup.
$^1$H NMR (500 MHz, CDCl$_3$): δ 1.50-1.58 (1H, m), 1.61 (1H, td, J=12.5, 4.0 Hz), 1.83-1.93 (1H, m), 1.93-2.00 (1H, m), 2.04 (11H, d, J=12.5 Hz), 2.10-2.18 (1H, m), 3.23-3.35 (2H, m), 3.70-3.76 (1H, m), 3.78 (6H, s), 3.80 (3H, s), 3.83 (3H, s), 3.85 (3H, s), 3.99 (1H, d, J=4.0 Hz), 6.59 (2H, s), 6.68-6.72 (2H, m), 6.77 (1H, d, J=7.9 Hz); $^{13}$C NMR (125 MHz, CDCl$_3$): δ 24.3, 32.6, 35.4, 43.7, 50.6, 52.0, 55.9, 56.0, 56.1 (2×C), 60.8, 105.7 (2×C), 111.1, 111.6, 116.4, 117.8, 120.5, 124.5, 134.2, 137.0, 137.4, 147.7, 148.9, 152.8 (2×C). IR (KBr) 3005, 2940, 2220, 1587, 1506 cm$^{-1}$. EIMS m/z (rel int) 450 (100, M$^+$); HREIMS m/z calcd for $C_{26}H_{30}N_2O_5$: 450.2155; found: 450.2156 [M]$^+$.

trans-7-(3,4-Dimethoxyphenyl)-6-(3-methoxyphenyl)-1,2,3,7,8,8a-hexahydroindolizine-5-carbonitrile (12f)

Yield 70%; yellow syrup.

$^1$H NMR (500 MHz, CDCl$_3$): δ 1.51-1.58 (1H, m), 1.61 (1H, td, J=12.3, 4.0 Hz), 1.82-1.99 (2H, m), 2.03 (1H, d, J=12.3 Hz), 2.10-2.17 (1H, m), 3.21-3.28 (1H, m), 3.30 (1H, td, J=10.0, 6.3 Hz), 3.70-3.75 (1H, m), 3.75 (3H, s), 3.80 (3H, s), 3.83 (3H, s), 4.04 (1H, d, J=4.0 Hz), 6.66 (1H, s), 6.67 (1H, d, J=8.1 Hz), 6.72 (1H, d, J=8.1 Hz), 6.74 (1H, d, J=8.1 Hz), 6.91 (1H, s), 6.97 (1H, d, J=8.1 Hz), 7.16 (1H, t, J=8.1 Hz); $^{13}$C NMR (125 MHz, CDCl$_3$): δ 24.2, 32.5, 35.5, 43.6, 50.5, 51.9, 55.1, 55.8, 55.9, 111.0, 111.6, 112.5, 114.1, 116.1, 118.1, 120.4, 120.8, 124.5, 129.1, 136.8, 140.1, 147.6, 148.8, 159.3. IR (KBr) 3066, 2935, 2218, 1612, 1566, 1513 cm$^{-1}$. EIMS m/z (rel int) 390 (100, M$^+$); HREIMS m/z calcd for $C_{24}H_{26}N_2O_3$: 390.1943; found: 390.1941 [M]$^+$.

trans-7-(3,4-Dimethoxyphenyl)-6-(4-methoxyphenyl)-1,2,3,7,8,8a-hexahydroindolizine-5-carbonitrile (12g)

Yield 64%; yellow syrup.

$^1$H NMR (500 MHz, CDCl$_3$): δ 1.50-1.56 (1H, m), 1.62 (1H, td, J=12.4, 4.0 Hz), 1.82-1.98 (2H, m), 2.02 (1H, d, J=12.4 Hz), 2.10-2.17 (1H, m), 3.21-3.30 (2H, m), 3.70 (1H, td, J=9.3, 2.0 Hz), 3.75 (3H, s), 3.80 (3H, s), 3.83 (3H, s), 4.00 (1H, d, J=4.0 Hz), 6.64 (1H, d, J=1.9 Hz), 6.66 (1H, dd, J=8.1, 1.9 Hz), 6.74 (1H, d, J=8.1 Hz), 6.79 (2H, d, J=8.8 Hz), 7.29 (2H, d, J=8.8 Hz); $^{13}$C NMR (125 MHz, CDCl3): δ 24.3, 32.5, 35.7, 43.8, 50.5, 51.7, 55.1, 55.8, 55.9, 111.0, 111.7, 113.7 (2×C), 116.5, 117.6, 120.4, 125.2, 129.4 (2×C), 131.1, 136.9, 147.5, 148.8, 158.8. IR (KBr) 3005, 2943, 2218, 1601, 1570, 1512 cm$^{-1}$. EIMS m/z (rel int) 390 (100, M$^4$); HREIMS m/z calcd for $C_{24}H_{26}N_2O_3$: 390.1943; found: 390.1947 [M]$^+$.

trans-6-(2,3,4-Trimethoxyphenyl)-7-(3,4-dimethoxyphenyl)-1,2,3,7,8,8a-hexahydroindolizine-5-carbonitrile (12h)

Yield 78%; yellow syrup.

$^1$H NMR (500 MHz, CDCl$_3$): δ 1.52-1.57 (1H, m), 1.63 (1H, td, J=12.7, 4.5 Hz), 1.82-1.96 (2H, m), 1.98 (1H, d, J=12.7 Hz), 2.10-2.18 (1H, m), 3.23-3.33 (2H, m), 3.69 (1H, td, J=9.0, 1.9 Hz), 3.79 (3H, s), 3.81 (3H, s), 3.83 (3H, s), 3.84 (3H, s), 3.89 (3H, s), 4.11 (1H, d, J=4.5 Hz), 6.55 (1H, d, J=8.6 Hz), 6.66-6.70 (2H, m), 6.75 (1H, d, J=8.0 Hz), 6.88 (1H, d, J=8.6 Hz); $^{13}$C NMR (125 MHz, CDCl$_3$): δ 24.3, 32.6, 35.5, 43.3, 50.7, 51.7, 55.7, 55.8, 55.9, 60.8, 61.2, 106.9, 110.9, 111.9, 115.9, 119.3, 120.4, 123.2, 125.4, 126.3, 137.0, 142.1, 147.5, 148.7, 151.8, 153.4. IR (KBr) 3021, 2941, 2222, 1595, 1514 cm$^{1'}$. EIMS (rel int) 450 (88, M$^+$), 419 (100); HREIMS m/z calcd for $C_{26}H_{30}N_2O_5$: 450.2155; found: 450.2157 [M]$^+$.

trans-6,7-Bis(3,4-dimethoxyphenyl)-1,2,3,7,8,8a-hexahydroindolizine-5-carbonitrile (trans-121)

Yield 64%; yellow syrup.

$^1$H NMR (500 MHz, CDCl$_3$): δ 1.50-1.57 (1H, m), 1.63 (1H, td, J=12.0, 4.0 Hz), 1.82-1.99 (2H, m), 2.03 (1H, d, J=12.0 Hz), 2.10-2.17 (1H, m), 3.22-3.32 (2H, m), 3.68-3.75 (1H, m), 3.81 (3H, s), 3.82 (3H, s), 3.83 (3H, s), 3.84 (3H, s), 4.01 (1H, d, J=4.0 Hz), 6.65-6.70 (2H, m), 6.73-6.78 (2H, m), 6.89-6.96 (2H, m); $^{13}$C NMR (125 MHz, CDCl$_3$): δ 24.2, 32.5, 35.5, 43.7, 50.5, 51.8, 55.8 (4×C), 110.9, 111.0, 111.6 (2×C), 116.5, 117.5, 120.4, 120.8, 124.9, 131.3, 136.9, 147.5, 148.2, 148.4, 148.8. IR (KBr) 3075, 2909, 2218, 1597, 1512 cm$^{-1}$. EIMS m/z (rel int) 420 (100, M$^+$); HREIMS m/z calcd for $C_{25}H_{28}N_2O_4$: 420.2049; found: 420.2054 [M]$^+$.

trans-2-(2,3,4-Trimethoxyphenyl)-3-(3,4-dimethoxyphenyl)-2,6,7,8,9,9a-hexahydro-1H-quinolizine-4-carbonitrile (13a)

Yield 84%; yellow syrup.

$^1$H NMR (500 MHz, CDCl$_3$): δ 1.27-1.36 (2H, m), 1.50-1.66 (2H, m), 1.71-1.82 (3H, m), 2.02 (1H, td, J=12.2, 5.0 Hz), 2.61 (1H, t, J=12.2 Hz), 2.70 (1H, td, J=12.0, 2.3 Hz), 3.77 (3H, s), 3.81 (3H, s), 3.83 (3H, s), 3.84 (3H, s), 3.85 (3H, s), 3.98 (1H, d, J=12.0 Hz), 4.17 (1H, d, J=5.0 Hz), 6.62 (1H, d, J=8.8 Hz), 6.73 (1H, d, J=8.3 Hz), 6.80 (1H, d, J=1.9 Hz), 6.81 (1H, d, J=8.8 Hz), 6.86 (1H, dd, J=8.3, 1.9 Hz); $^{13}$C NMR (125 MHz, CDCl$_3$): δ 24.1, 25.9, 31.9, 36.2, 37.0, 50.9, 51.6, 55.7, 55.8, 55.9, 60.6, 60.9, 106.4, 110.7, 111.7, 116.1, 121.0, 121.3, 123.9, 127.9, 130.3, 131.9, 142.1, 148.3, 148.4, 151.0, 152.5. IR (KBr) 3057, 2943, 2218, 1600, 1516 cm$^{-1}$. EIMS m/z (rel int) 464 (100, M$^+$); HREIMS m/z calcd for $C_{27}H_{32}N_2O_5$: 464.2311; found: 464.2308 [M]$^+$.

trans-3-(3,4-Dimethoxyphenyl)-2-(4-methoxyphenyl)-2,6,7,8,9,9a-hexahydro-1H-quinolizine-4-carbonitrile (13b)

Yield 90%; yellow syrup.

$^1$H NMR (500 MHz, CDCl$_3$): δ 1.26-1.35 (2H, m), 1.49-1.64 (2H, m), 1.71-1.82 (3H, m), 2.07 (1H, td, J=12.5, 5.4 Hz), 2.63 (1H, t, J=12.5 Hz), 2.71 (1H, t, J=11.5 Hz), 3.75 (3H, s), 3.78 (3H, s), 3.80 (1H, d, J=5.4 Hz), 3.81 (3H, s), 3.98 (1H, d, J=11.5 Hz), 6.72 (1H, d, J=8.3 Hz), 6.78 (1H, s), 6.83 (1H, d, J=8.3 Hz), 6.85 (2H, d, J=8.1 Hz), 7.12 (2H, d, J=8.1 Hz); $^{13}$C NMR (125 MHz, CDCl$_3$): δ 24.1, 26.0, 32.0, 37.6, 43.0, 50.9, 51.3, 55.2, 55.7, 55.8, 110.8, 111.9, 113.8 (2×C), 116.0, 120.9, 121.0, 127.6, 129.3 (2×C), 131.9, 137.0, 148.3, 148.5, 158.3. IR (KBr) 3001, 2936, 2218, 1601, 1582, 1512 cm$^{-1}$. EIMS m/z (rel int) 404 (100, M$^+$); HREIMS m/z calcd for $C_{25}H_{28}N_2O_3$: 404.2100; found: 404.2102 [M]$^+$.

trans-3-(3,4-Dimethoxyphenyl)-2-(3-methoxyphenyl)-2,6,7,8,9,9a-hexahydro-1H-quinolizine-4-carbonitrile (13c)

Yield 91%; yellow syrup.

$^1$H NMR (500 MHz, CDCl$_3$): δ 1.26-1.35 (2H, m), 1.51-1.65 (2H, m), 1.71-1.81 (2H, m), 1.83 (1H, d, J=13.2 Hz), 2.09 (1H, td, J=12.2, 5.7 Hz), 2.66 (1H, t, J=12.2 Hz), 2.72 (1H, td, J=12.2, 2.3 Hz), 3.76 (3H, s), 3.79 (1H, br s), 3.81 (3H, s), 3.82 (1H, d, J=5.7 Hz), 3.99 (1H, d, J=12.2 Hz), 6.73 (1H, d, J=8.4 Hz), 6.74-6.77 (2H, m), 6.79 (1H, d, J=2.0

Hz), 6.81 (1H, d, J=8.4 Hz), 6.84 (1H, dd, J=8.4, 2.0 Hz), 7.23 (1H, t, J=8.4 Hz); $^{13}$C NMR (125 MHz, CDCl$_3$): δ 24.0, 25.9, 32.0, 37.3, 43.8, 50.9, 51.5, 55.2, 55.7, 55.8, 110.8, 111.5, 111.9, 114.7, 116.0, 120.8, 121.1, 121.2, 127.0, 129.4, 131.8, 146.6, 148.3, 148.5, 159.6. IR (KBr) 3055, 2920, 2214, 1643, 1570, 1504 cm$^{-1}$. EIMS m/z (rel int) 404 (100, M$^+$); HREIMS m/z calcd for C$_{25}$H$_{28}$N$_2$O$_3$: 404.2100; found: 404.2107 [M]$^+$.

trans-2-(3,4,5-Trimethoxyphenyl)-3-(3,4-dimethoxyphenyl)-2,6,7,8,9,9a-hexahydro-1H-quinolizine-4-carbonitrile (13d)

Yield 90%; yellow syrup.
$^1$H NMR (500 MHz, CDCl$_3$): δ 1.26-1.39 (2H, m), 1.57-1.67 (2H, m), 1.72-1.87 (3H, m), 2.08 (1H, td, J=12.5, 5.6 Hz), 2.62-2.71 (2H, m), 3.78 (3H, s), 3.79 (1H, d, J=5.6 Hz), 3.82 (6H, s), 3.83 (6H, s), 4.01 (1H, d, J=11.4 Hz), 6.42 (2H, s), 6.75 (1H, d, J=8.2 Hz), 6.82 (1H, d, J=1.4 Hz), 6.85 (1H, dd, J=8.2, 1.4 Hz); $^{13}$C NMR (125 MHz, CDCl$_3$): δ 24.0, 25.9, 31.8, 37.3, 43.9, 51.0, 51.7, 55.7, 55.8, 56.1 (2×C), 60.8, 105.5 (2×C), 110.8, 111.8, 115.9, 121.1 (2×C), 127.1, 131.8, 136.6, 140.4, 148.3, 148.5, 153.1 (2×C). IR (KBr) 3005, 2938, 2220, 1589, 1516, 1504 cm$^{-1}$. EIMS m/z (rel int) 464 (77, M$^+$), 269 (100); HREIMS m/z calcd for C$_{27}$H$_{32}$N$_2$O$_5$: 464.2311; found: 464.2306 [M]$^+$.

trans-3-(3,4,5-Trimethoxyphenyl)-2-(3,4-dimethoxyphenyl)-2,6,7,8,9,9a-hexahydro-1H-quinolizine-4-carbonitrile (13e)

Yield 86%; yellow syrup.
$^1$H NMR (500 MHz, CDCl$_3$): δ 1.27-1.38 (2H, m), 1.57-1.65 (2H, m), 1.74-1.85 (3H, m), 2.06 (1H, td, J=12.9, 5.3 Hz), 2.67 (1H, td, J=12.9, 2.0 Hz), 2.70 (1H, td, J=12.2, 2.4 Hz), 3.72 (6H, s), 3.77 (1H, d, J=5.3 Hz), 3.80 (3H, s), 3.86 (3H, s), 3.87 (3H, s), 4.02 (1H, d, J=12.2 Hz), 6.49 (2H, s), 6.73 (1H, d, J=1.8 Hz), 6.77 (1H, dd, J=8.2, 1.8 Hz), 6.84 (1H, d, J=8.2 Hz); $^{13}$C NMR (125 MHz, CDCl$_3$): δ 24.1, 26.0, 32.0, 37.4, 43.4, 50.8, 51.6, 55.9 (2×C), 56.0 (2×C), 60.8, 105.9 (2×C), 111.1, 111.7, 115.8, 120.5, 121.0, 127.1, 134.7, 137.5, 137.6, 147.8, 148.9, 152.7 (2×C). IR (KBr) 3005, 2938, 2218, 1576, 1510 cm$^{-1}$. EIMS m/z (rel int) 464 (100, M$^+$); HREIMS m/z calcd for C$_{27}$H$_{32}$N$_2$O$_5$: 464.2311; found: 464.2306 [M]$^+$.

trans-2-(3,4-Dimethoxyphenyl)-3-(3-methoxyphenyl)-2,6,7,8,9,9a-hexahydro-1H-quinolizine-4-carbonitrile (13f)

Yield 90%; yellow syrup.
$^1$H NMR (500 MHz, CDCl$_3$): δ 1.27-1.37 (2H, m), 1.53-1.65 (2H, m), 1.71-1.85 (3H, m), 2.06 (1H, td, J=12.0, 4.5 Hz), 2.65 (1H, t, J=12.0 Hz), 2.70 (1H, td, J=12.0, 2.2 Hz), 3.72 (3H, s), 3.81 (1H, d, J=4.5 Hz), 3.84 (3H, s), 3.85 (3H, s), 4.00 (1H, d, J=12.0 Hz), 6.70 (1H, s), 6.72-6.76 (2H, m), 6.81 (1H, d, J=8.0 Hz), 6.82 (1H, s), 6.87 (1H, d, J=7.7 Hz), 7.15 (1H, t, J=8.0 Hz); $^{13}$C NMR (125 MHz, CDCl$_3$): δ 24.1, 25.9, 31.9, 37.6, 43.2, 50.9, 51.6, 55.1, 55.9 (2×C), 111.1, 111.8, 113.0, 114.3, 115.7, 120.5, 121.0, 121.4, 127.2, 129.1, 137.3, 140.7, 147.8, 148.9, 159.2. IR (KBr) 3017, 2935, 2218, 1612, 1516 cm$^{-1}$. EIMS m/z (rel int) 404 (100, M$^+$); HREIMS m/z calcd for C$_{25}$H$_{28}$N$_2$O$_3$: 404.2100; found: 404.2102 [M]$^+$.

trans-2-(3,4-Dimethoxyphenyl)-3-(4-methoxyphenyl)-2,6,7,8,9,9a-hexahydro-1H-quinolizine-4-carbonitrile (13g)

Yield 92%; yellow syrup.
$^1$H NMR (500 MHz, CDCl$_3$): δ 1.26-1.35 (2H, m), 1.50-1.64 (2H, m), 1.70-1.84 (3H, m), 2.07 (1H, t, J=11.0 Hz), 2.62 (1H, t, J=11.0 Hz), 2.68 (1H, t, J=12.2 Hz), 3.74 (3H, s), 3.80 (1H, br s), 3.85 (6H, s), 3.98 (1H, d, J=12.2 Hz), 6.69 (1H, s), 6.73 (1H, d, J=8.2 Hz), 6.77 (2H, d, J=8.2 Hz), 6.81 (d, J=8.2 Hz), 7.21 (2H, d, J=8.2 Hz); $^{13}$C NMR (125 MHz, CDCl$_3$): δ 24.1, 25.9, 31.9, 37.6, 43.3, 51.0, 51.5, 55.1, 55.8 (2×C), 111.0, 111.7, 113.6 (2×C), 116.0, 120.5, 121.0, 127.6, 129.6 (2×C), 131.6, 137.3, 147.7, 148.8, 159.0. IR (KBr) 3005, 2940, 2218, 1605, 1512 cm$^{-1}$. EIMS m/z (rel int) 404 (100, M$^+$); HREIMS m/z calcd for C$_{25}$H$_{28}$N$_2$O$_3$: 404.2100; found: 404.2097[M]$^+$.

trans-3-(2,3,4-Trimethoxyphenyl)-2-(3,4-dimethoxyphenyl)-2,6,7,8,9,9a-hexahydro-1H-quinolizine-4-carbonitrile (13h)

Yield 93%; yellow syrup.
$^1$H NMR (500 MHz, CDCl$_3$): δ 1.28-1.39 (2H, m), 1.50-1.63 (2H, m), 1.69-1.76 (1H, m), 1.76-1.85 (2H, m), 2.10 (1H, td, J=12.0, 5.6 Hz), 2.62-2.75 (2H, m), 3.78 (3H, s), 3.83 (6H, s), 3.84 (3H, s), 3.90 (3H, s), 3.90-3.95 (2H, m), 6.51 (1H, d, J=8.6 Hz), 6.69 (1H, s), 6.72 (1H, d, J=8.2 Hz), 6.77 (1H, d, J=8.6 Hz), 6.78 (1H, d, J=8.2 Hz); $^{13}$C NMR (125 MHz, CDCl$_3$): δ 24.2, 25.8, 31.8, 37.6, 42.7, 51.2, 51.7, 55.8 (3×C), 60.9, 61.4, 106.9, 110.8, 112.0, 115.5, 120.5 (2×C), 122.8, 125.8, 126.1, 137.2, 142.2, 147.6, 148.7, 152.0, 153.6. IR (KBr) 3019, 2938, 2224, 1595, 1518 cm$^{-1}$. EIMS m/z (rel int) 464 (96, M$^+$), 433 (100); HREIMS m/z calcd for C$_{27}$H$_{32}$N$_2$O$_5$: 464.2311; found: 464.2321 [M]$^+$.

trans-2,3-Bis(3,4-dimethoxyphenyl)-2,6,7,8,9,9a-hexahydro-1H-quinolizine-4-carbonitrile (13i)

Yield 92%; yellow syrup.
$^1$H NMR (500 MHz, CDCl$_3$): δ 1.27-1.37 (2H, m), 1.51-1.64 (2H, m), 1.72-1.86 (3H, m), 2.07 (1H, td, J=13.0, 5.3 Hz), 2.62-2.73 (2H, m), 3.76 (3H, s), 3.80 (1H, d, J=5.3 Hz), 3.81 (3H, s), 3.85 (6H, s), 4.00 (1H, d, J=11.9 Hz), 6.71-6.77 (3H, m), 6.80-6.86 (3H, m); $^{13}$C NMR (125 MHz, CDCl$_3$): δ 24.1, 26.0, 31.9, 37.5, 43.4, 50.9, 51.6, 55.8 (4×C), 110.8, 111.0, 111.7, 111.9, 116.0, 120.5, 120.9, 121.0, 127.4, 131.9, 137.4, 147.7, 148.3, 148.5, 148.9. IR (KBr) 3009, 2932, 2218, 1601, 1512 cm$^{-1}$. EIMS m/z (rel int) 434 (100, M$^+$); HREIMS m/z calcd for C$_{26}$H$_{30}$N$_2$O$_4$: 434.2206; found: 434.2204 [M]$^+$.

<u>5. Synthesis of compounds 10a-i and 11a-i by reductive decyanization</u>

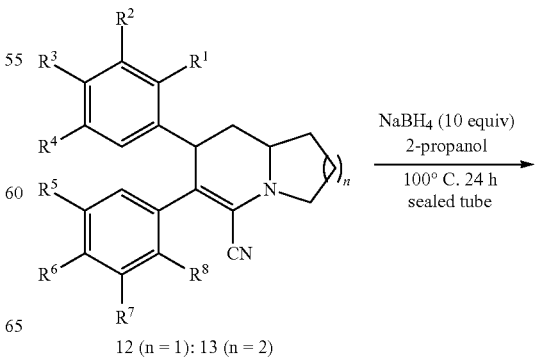

12 (n = 1): 13 (n = 2)

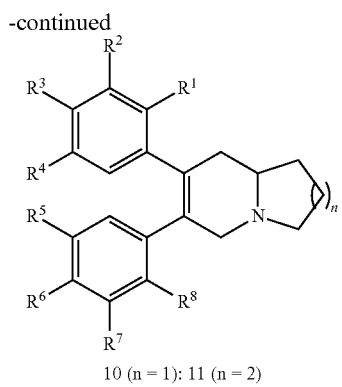

10 (n = 1); 11 (n = 2)

a: $R^1 = R^2 = R^3 = R^6 = R^7 = OCH_3$
b: $R^3 = R^6 = R^7 = OCH_3$
c: $R^2 = R^6 = R^7 = OCH_3$
d: $R^2 = R^3 = R^4 = R^6 = R^7 = OCH_3$
e: $R^2 = R^3 = R^5 = R^6 = R^7 = OCH_3$
f: $R^2 = R^3 = R^7 = OCH_3$
g: $R^2 = R^3 = R^6 = OCH_3$
h: $R^2 = R^3 = R^6 = R^7 = R^8 = OCH_3$
i: $R^2 = R^3 = R^6 = R^7 = OCH_3$

Typical procedure for the synthesis of cis-stilbene derivatives 10a-i (and 11a-i) by reductive decyanization. A mixture of cycloadducts 12a-i (and trans-13a-i, 0.25 mmol) and NaBH$_4$ (5 mmol) in 2-propanol (5 mL) in a sealed tube was heated at 100° C. (or 120° C.) for 24 h. After cooling, the reaction mixture was quenched with H$_2$O (1 mL), and the solvent was evaporated in vacuo. The residue was diluted with H$_2$O (10 mL) and extracted with CHCl$_3$ (5×20 mL), and the combined extracts were washed with H$_2$O, dried over anhydrous MgSO$_4$, and filtered. The filtrate was concentrated and the residue was purified by column chromatography over silica gel by eluting with EtOAc, affording pure stilbene derivatives 10a-i (and 11a-i). The complete spectral data of these compounds are given below.

7-(2,3,4-Trimethoxyphenyl)-6-(3,4-dimethoxyphenyl)-1,2,3,5,8,8a-hexahydroindolizine (10a)

Yield 92%; pale yellow syrup.
$^1$H NMR (500 MHz, CDCl$_3$): δ 1.48-1.58 (1H, m), 1.77-1.87 (1H, m), 1.89-2.00 (1H, m), 2.03-2.12 (1H, m), 2.26 (1H, q, J=8.5 Hz), 2.30-2.49 (2H, m), 2.69 (1H, d, J=9.8 Hz), 3.14 (1H, d, J=15.8 Hz), 3.32 (1H, t, J=8.5 Hz), 3.61 (3H, s), 3.77 (3H, s), 3.78 (3H, s), 3.79 (3H, s), 3.86 (3H, s), 3.90 (1H, d, J=15.8 Hz), 6.39 (1H, d, J=8.6 Hz), 6.52 (1H, d, J=8.6 Hz), 6.55 (1H, d, J=1.5 Hz), 6.66 (1H, d, J=8.3 Hz), 6.70 (1H, dd, J=8.3, 1.5 Hz); $^{13}$C NMR (125 MHz, CDCl$_3$): δ 21.5, 30.7, 38.5, 54.4, 55.5, 55.7, 55.8, 57.5, 60.2, 60.6, 60.7, 106.8, 110.4, 112.7, 120.4, 125.3, 129.1, 131.2, 133.3, 133.6, 141.9, 147.3, 147.9, 151.5, 152.4. IR (KBr) 3013, 2930, 1601, 1514 cm$^{-1}$. EIMS m/z (rel int) 425 (40, M$^+$), 356 (100); HREIMS m/z calcd for C$_{25}$H$_{31}$NO$_5$: 425.2202; found: 425.2210 [M]$^+$.

Hispidine (10b)

Yield 100%; white powder, mp 87-90° C.
$^1$H NMR (500 MHz, CDCl$_3$): δ 1.50-1.60 (1H, m), 1.78-1.88 (1H, m), 1.89-2.00 (1H, m), 2.05-2.14 (1H, m), 2.25 (1H, q, J=8.9 Hz), 2.36-2.45 (2H, m), 2.71 (1H, dd, J=12.9, 2.1 Hz), 3.08 (1H, d, J=15.8 Hz), 3.31 (1H, td, J=8.9, 1.8 Hz), 3.57 (3H, s), 3.72 (3H, s), 3.81 (3H, s), 3.89 (1H, d, J=15.8 Hz), 6.48 (1H, s), 6.64-6.69 (4H, m), 6.95 (2H, d, J=8.7 Hz); $^{13}$C NMR (125 MHz, CDCl$_3$): δ 21.5, 30.8, 38.8, 54.3, 55.1, 55.5, 55.7, 57.7, 60.4, 110.5, 113.3 (3×C), 120.9, 129.9 (2×C), 132.5, 132.7, 133.6, 135.0, 147.3, 148.1, 157.8. IR (KBr) 3121, 2916, 1605, 1574, 1516 cm$^{-1}$. EIMS m/z (rel int) 365 (30, M$^+$), 265 (100); HREIMS m/z calcd for C$_{23}$H$_{27}$NO$_3$: 365.1991; found: 365.1996 [M]$^+$.

6-(3,4-Dimethoxyphenyl)-7-(3-methoxyphenyl)-1,2,3,5,8,8a-hexahydroindolizine (10c)

Yield 96%; white powder, mp 119-120° C.
$^1$H NMR (500 MHz, CDCl$_3$): δ 1.50-1.60 (1H, m), 1.78-1.88 (1H, m), 1.90-2.00 (1H, m), 2.06-2.14 (1H, m), 2.26 (1H, q, J=9.0 Hz), 2.37-2.47 (2H, m), 2.72 (1H, dd, J=13.0, 2.2 Hz), 3.09 (1H, d, J=16.0 Hz), 3.32 (1H, td, J=9.0, 2.0 Hz), 3.55 (3H, s), 3.60 (3H, s), 3.80 (3H, s), 3.89 (1H, d, J=16.0 Hz), 6.49 (1H, s), 6.57 (1H, t, J=2.0 Hz), 6.61-6.68 (4H, m), 7.05 (1H, t, J=7.9 Hz); $^{13}$C NMR (125 MHz, CDCl$_3$): δ 21.5, 30.8, 38.8, 54.3, 55.0, 55.6, 55.7, 57.6, 60.3, 110.5, 111.9, 113.2, 114.5, 120.8, 121.3, 128.8, 133.2, 133.3, 133.4, 144.2, 147.5, 148.1, 159.1. IR (KBr) 3063, 2928, 1597, 1578, 1516 cm$^{-1}$. EIMS m/z (rel int) 365 (17, M$^+$), 265 (100); HREIMS m/z calcd for C$_{23}$H$_2$NO$_3$: 365.1991; found: 265.2000 [M]$^+$.

7-(3,4,5-Trimethoxyphenyl)-6-(3,4-dimethoxyphenyl)-1,2,3,5,8,8a-hexahydroindolizine (10d)

Yield 96%; pale yellow syrup.
$^1$H NMR (500 MHz, CDCl$_3$): δ 1.52-1.62 (1H, m), 1.81-1.89 (1H, m), 1.91-2.01 (1H, m), 2.08-2.16 (1H, m), 2.27 (1H, q, J=8.8 Hz), 2.37-2.47 (2H, m), 2.74 (1H, d, J=13.0 Hz), 3.10 (1H, d, J=16.1 Hz), 3.32 (1H, t, J=8.8 Hz), 3.59 (3H, s), 3.62 (6H, s), 3.77 (3H, s), 3.81 (3H, s), 3.89 (1H, d, J=16.1 Hz), 6.27 (2H, s), 6.53 (1H, d, J=1.4 Hz), 6.67 (1H, dd, J=8.3, 1.4 Hz), 6.70 (1H, d, J=8.3 Hz); $^{13}$C NMR (125 MHz, CDCl$_3$): δ 21.5, 30.8, 38.6, 54.3, 55.7, 55.8, 55.9 (2×C), 57.6, 60.4, 60.8, 106.3 (2×C), 110.7, 113.0, 120.8, 133.1, 133.2, 133.6, 136.4, 138.1, 147.6, 148.3, 152.6 (2×C). IR (KBr) 3019, 2911, 1582, 1514 cm$^{-1}$. EIMS m/z (rel int) 425 (48, M$^+$), 325 (100); HREIMS m/z calcd for C$_{25}$H$_{31}$NO$_5$: 425.2202; found: 425.2209 [M]$^+$.

6-(3,4,5-Trimethoxyphenyl)-7-(3,4-dimethoxyphenyl)-1,2,3,5,8,8a-hexahydroindolizine (10e)

Yield 100%; pale yellow syrup.
$^1$H NMR (500 MHz, CDCl$_3$): δ 1.51-1.62 (11H, m), 1.79-1.90 (1H, m), 1.90-2.01 (1H, m), 2.07-2.16 (1H, m), 2.27 (1H, q, J=8.8 Hz), 2.38-2.48 (2H, m), 2.75 (1H, d, J=13.0 Hz), 3.11 (1H, d, J=16.0 Hz), 3.32 (1H, t, J=8.8 Hz), 3.57 (3H, s), 3.63 (6H, s), 3.78 (3H, s), 3.81 (3H, s), 3.88 (1H, d, J=16.0 Hz), 6.29 (2H, s), 6.52 (1H, s), 6.66-6.72 (2H, m); $^{13}$C NMR (125 MHz, CDCl$_3$): δ 21.5, 30.9, 38.5, 54.2, 55.6, 55.8, 56.0 (2×C), 57.6, 60.4, 60.8, 106.5 (2×C), 110.6, 112.8, 120.5, 133.0, 133.2, 135.0, 136.5, 136.7, 147.4, 148.1, 152.7 (2×C). IR (KBr) 3018, 2934, 1582, 1516 cm$^{-1}$. EIMS m/z (rel int) 425 (44, M$^+$) 325 (100); HREIMS m/z calcd for C$_{25}$H$_{31}$NO$_5$: 425.2202; found: 425.2209 [M]$^+$.

7-(3,4-Dimethoxyphenyl)-6-(3-methoxyphenyl)-1,2,3,5,8,8a-hexahydroindolizine (10l)

Yield 100%; white powder, mp 53-55° C.
$^1$H NMR (500 MHz, CDCl$_3$): δ 1.52-1.62 (1H, m), 1.78-1.88 (1H, m), 1.90-2.00 (1H, m), 2.06-2.15 (1H, m), 2.25 (1H, q, J=8.9 Hz), 2.37-2.48 (2H, m), 2.73 (1H, dd, J=13.0, 2.2 Hz), 3.10 (1H, d, J=16.0 Hz), 3.30 (1H, td, J=8.9, 1.9 Hz), 3.53 (3H, s), 3.61 (3H, s), 3.80 (3H, s), 3.87 (1H, d, J=16.0 Hz), 6.48 (1H, s), 6.59 (1H, t, J=1.8 Hz), 6.62-6.71 (4H, m), 7.06 (1H, t, J=7.9 Hz); $^{13}$C NMR (125 MHz, CDCl$_3$): δ 21.5, 30.8, 38.5, 54.3, 55.1, 55.5, 55.7, 57.8, 60.4, 110.5, 112.1, 113.0, 114.8, 120.5, 121.5, 128.9, 133.1, 133.2, 134.9, 142.8, 147.3, 147.9, 159.2. IR (KBr) 3067, 2916, 1582, 1516 cm$^{-1}$. EIMS m/z (rel int) 365 (100, M$^+$); HREIMS m/z calcd for C$_{23}$H$_{27}$NO$_3$: 365.1991; found: 365.1996 [M]$^+$.

Seco-antofine (10g)

Yield 100%; white powder, mp 108-109° C.
$^1$H NMR (500 MHz, CDCl$_3$): δ 1.51-1.61 (1H, m), 1.78-1.88 (1H, m), 1.89-2.00 (1H, m), 2.06-2.14 (1H, m), 2.25 (1H, q, J=8.8 Hz), 2.36-2.46 (2H, m), 2.73 (1H, dd, J=12.9, 2.1 Hz), 3.07 (1H, d, J=15.9 Hz), 3.30 (1H, td, J=8.8, 1.9 Hz), 3.54 (3H, s), 3.72 (3H, s), 3.80 (3H, s), 3.86 (1H, d, J=15.9 Hz), 6.47 (1H, d, J=1.2 Hz), 6.65-6.68 (2H, m), 6.68 (2H, d, J=8.8 Hz), 6.97 (2H, d, J=8.8 Hz); $^{13}$C NMR (125 MHz, CDCl$_3$): δ 21.5, 30.8, 38.5, 54.3, 55.1, 55.5, 55.7, 57.9, 60.4, 110.5, 113.1, 113.4 (2×C), 120.7, 130.2 (2×C), 132.6, 132.7, 133.6, 135.1, 147.2, 147.9, 158.0. IR (KBr) 3062, 2967, 1643, 1605, 1582, 1574, 1520 cm$^{-1}$. EIMS m/z (rel int) 365 (46, M$^+$), 265 (100); HREIMS m/z calcd for C$_{23}$H$_{27}$NO$_3$: 365.1991; found: 365.1992 [M]$^+$.

6-(2,3,4-Trimethoxyphenyl)-7-(3,4-dimethoxyphenyl)-1,2,3,5,8,8a-hexahydroindolizine (10h)

Yield 94%; pale yellow syrup.
$^1$H NMR (500 MHz, CDCl$_3$): δ 1.54-1.63 (1H, m), 1.78-1.86 (1H, m), 1.90-2.00 (1H, m), 2.05-2.13 (1H, m), 2.23 (1H, q, J=9.0 Hz), 2.40-2.53 (2H, m), 2.69 (1H, d, J=15.9 Hz), 3.11 (1H, br d, J=14.6 Hz), 3.27 (1H, td, J=9.0, 1.7 Hz), 3.58 (3H, s), 3.74 (1H, br d, J=14.6 Hz), 3.77 (3H, s), 3.78 (3H, s), 3.79 (3H, s), 3.82 (3H, s), 6.43 (1H, d, J=8.6 Hz), 6.53 (1H, d, J=1.7 Hz), 6.58 (1H, d, J=8.6 Hz), 6.66 (1H, d, J=8.3 Hz), 6.70 (1H, dd, J=8.3, 1.7 Hz); $^{13}$C NMR (125 MHz, CDCl$_3$): δ 21.4, 30.7, 38.2, 54.3, 55.5, 55.7, 55.8, 57.8, 60.5, 60.6, 60.7, 106.9, 110.3, 112.4, 120.1, 125.7, 127.7, 130.5, 133.3, 135.1, 141.9, 147.1, 147.7, 151.6, 152.5. IR (KBr) 3021, 2940, 1599, 1518 cm$^{-1}$. EIMS m/z (rel int) 425 (100, M$^+$); HREIMS m/z calcd for C$_{25}$H$_{31}$NO$_5$: 425.2202; found: 425.2191 [M]$^+$.

Septicine (10i)

Yield 100%; white powder, mp 142-144° C. (X. Xu, Y. Liu, C. M. Park, Angew Chem. Int. Ed. 2012, 51, 9372-9376; mp 134-135° C.).
$^1$H NMR (500 MHz, CDCl$_3$): δ 1.51-1.61 (1H, m), 1.78-1.88 (1H, m), 1.90-2.00 (1H, m), 2.06-2.15 (1H, m), 2.26 (1H, q, J=8.9 Hz), 2.36-2.46 (2H, m), 2.74 (1H, dd, J=12.9, 2.1 Hz), 3.09 (1H, d, J=15.8 Hz), 3.31 (1H, td, J=8.9, 1.8 Hz), 3.57 (3H, s), 3.60 (3H, s), 3.80 (3H, s), 3.81 (3H, s), 3.89 (1H, d, J=15.8 Hz), 6.52 (1H, d, J=1.7 Hz), 6.54 (1H, d, J=1.8 Hz), 6.63-6.69 (4H, m); $^{13}$C NMR (125 MHz, CDCl$_3$): δ 21.5, 30.9, 38.7, 54.3, 55.6, 55.7, 55.8 (2×C), 57.7, 60.4, 110.6, 110.7, 112.9, 113.1, 120.7, 121.0, 132.8, 132.9, 133.8, 135.2, 147.3, 147.5, 148.1, 148.2. IR (KBr) 3044, 2924, 1597, 1532, 1516, 1508 cm$^{-1}$. EIMS m/z (rel int) 395 (59, M$^+$), 295 (100); HREIMS m/z calcd for C$_{24}$H$_{29}$NO$_4$: 395.2097; found: 395.2090 [M]$^+$.

2-(2,3,4-Trimethoxyphenyl)-3-(3,4-dimethoxyphenyl)-4,6,7,8,9,9a-hexahydro-1H-quinolizine (11a)

Yield 95%; pale yellow syrup.
$^1$H NMR (500 MHz, CDCl$_3$): δ 1.27-1.42 (2H, m), 1.69-1.77 (2H, m), 1.77-1.85 (2H, m), 2.09-2.16 (1H, m), 2.27-2.37 (2H, m), 2.50 (1H, br d, J=12.9 Hz), 3.06-3.14 (2H, m), 3.57 (3H, s), 3.65 (1H, d, J=16.5 Hz), 3.76 (3H, s), 3.78 (3H, s), 3.79 (3H, s), 3.86 (3H, s), 6.39 (1H, d, J=8.5 Hz), 6.51 (1H, d, J=8.5 Hz), 6.55 (1H, d, J=1.8 Hz), 6.66 (1H, d, J=8.3 Hz), 6.70 (1H, dd, J=8.3, 1.8 Hz); $^{13}$C NMR (125 MHz, CDCl$_3$): δ 24.4, 25.9, 33.2, 39.6, 55.5, 55.6, 55.7, 55.8, 57.8, 59.8, 60.7 (2×C), 106.8, 110.3, 112.6, 120.3, 125.3, 128.6, 130.1, 132.1, 133.2, 141.9, 147.3, 147.9, 151.5, 152.4. IR (KBr) 3057, 2930, 1595, 1514 cm$^{-1}$. EIMS m/z (rel int) 439 (57, M$^+$), 356 (100); HREIMS m/z calcd for C$_{26}$H$_{33}$NO$_5$: 439.2359; found: 439.2354 [M]$^+$.

3-(3,4-Dimethoxyphenyl)-2-(4-methoxyphenyl)-4,6,7,8,9,9a-hexahydro-1H-quinolizine (11b)

Yield 100%; white powder, mp 106-108° C.
$^1$H NMR (500 MHz, CDCl$_3$): δ 1.27-1.43 (2H, m), 1.63-1.73 (2H, m), 1.77-1.89 (2H, m), 2.12 (1H, t, J=11.2 Hz), 2.25-2.34 (1H, m), 2.39 (1H, dd, J=17.2, 10.5 Hz), 2.51 (1H, d, J=17.2 Hz), 3.00-3.15 (2H, m), 3.57 (3H, s), 3.63 (1H, d, J=16.3 Hz), 3.72 (3H, s), 3.81 (3H, s), 6.49 (1H, s), 6.63-6.71 (4H, m), 6.95 (2H, d, J=8.4 Hz); $^{13}$C NMR (125 MHz, CDCl$_3$): δ 24.4, 25.9, 33.3, 39.8, 55.1, 55.5, 55.6, 55.7, 57.9, 60.1, 110.5, 113.2, 113.3 (2×C), 120.9, 129.8 (2×C), 131.3, 131.4, 133.3, 134.4, 147.4, 148.1, 157.8. IR (KBr) 3009, 2920, 1605, 1574, 1512 cm$^{-1}$. EIMS m/z (rel int) 379 (38, M$^+$), 265 (100); HREIMS m/z calcd for C$_{24}$H$_{29}$NO$_3$: 379.2147; found: 379.2155 [M]$^+$.

3-(3,4-Dimethoxyphenyl)-2-(3-methoxyphenyl)-4,6,7,8,9,9a-hexahydro-1H-quinolizine (11c)

Yield 97%; white powder, mp 138-139° C.
$^1$H NMR (500 MHz, CDCl$_3$): δ 1.28-1.43 (2H, m), 1.59-1.78 (2H, m), 1.78-1.90 (2H, m), 2.12 (1H, td, J=11.3, 5.0 Hz), 2.26-2.36 (1H, m), 2.41 (1H, dd, J=17.4, 11.9 Hz), 2.52 (1H, d, J=17.4 Hz), 3.03-3.14 (2H, m), 3.55 (3H, s), 3.60 (3H, s), 3.63 (1H, d, J=16.5 Hz), 3.80 (3H, s), 6.50 (1H, s), 6.57 (1H, t, J=1.5 Hz), 6.60-6.71 (4H, m), 7.05 (1H, t, J=7.4 Hz); $^{13}$C NMR (125 MHz, CDCl$_3$): δ 24.4, 25.9, 33.3, 39.8, 55.0, 55.5, 55.6, 55.7, 57.9, 60.0, 110.6, 111.9, 113.1, 114.4, 120.7, 121.2, 128.8, 131.9, 132.0, 133.1, 143.6, 147.5, 148.1. 159.1. IR (KBr) 3060, 2920, 1605, 1574, 1512 cm$^{-1}$. EIMS m/z (rel int) 379 (28, M$^+$), 296 (100); HREIMS m/z calcd for C$_{24}$H$_{29}$NO$_3$: 379.2147; found: 379.2144 [M]$^+$.

2-(3,4,5-Trimethoxyphenyl)-3-(3,4-dimethoxyphenyl)-4,6,7,8,9,9a-hexahydro-1H-quinolizine (11d)

Yield 98%; pale yellow syrup.
$^1$H NMR (500 MHz, CDCl$_3$): δ 1.32-1.41 (2H, m), 1.67-1.74 (1H, m), 1.78-1.95 (3H, m), 2.12 (1H, td, J=11.2, 4.4 Hz), 2.27-2.35 (1H, m), 2.41 (1H, dd, J=17.3, 9.1 Hz), 2.53 (1H, d, J=17.3 Hz), 3.03-3.13 (2H, m), 3.59 (3H, s), 3.61 (6H, s), 3.63 (1H, d, J=16.5 Hz), 3.77 (3H, s), 3.81 (3H, s), 6.27 (2H, s), 6.54 (1H, s), 6.66-6.72 (2H, m); $^{13}$C NMR (125 MHz, CDCl$_3$): δ 24.3, 25.9, 33.3, 39.5, 55.6, 55.7, 55.8, 55.9 (2×C), 57.9, 60.1, 60.8, 106.2 (2×C), 110.7, 112.9, 120.8, 131.8, 132.0, 133.2, 136.4, 137.5, 147.6, 148.3, 152.6 (2×C). IR (KBr) 3019, 2982, 1582, 1514 cm$^{-1}$. EIMS m/z (rel int) 439 (63, M$^+$), 325 (100); HREIMS m/z calcd for C$_{26}$H$_{33}$NO$_5$: 439.2359; found: 439.2351 [M]$^+$.

3-(3,4,5-Trimethoxyphenyl)-2-(3,4-dimethoxyphenyl)-4,6,7,8,9,9a-hexahydro-1H-quinolizine (11e)

Yield 100%; pale yellow syrup.
$^1$H NMR (500 MHz, CDCl$_3$): δ 1.29-1.43 (2H, m), 1.66-1.77 (2H, m), 1.79-1.89 (2H, m), 2.12 (1H, td, J=11.2, 5.0 Hz), 2.27-2.35 (1H, m), 2.41 (1H, dd, J=17.4, 10.1 Hz), 2.54 (1H, d, J=17.4 Hz), 3.04-3.13 (2H, m), 3.56 (3H, s), 3.61 (1H, d, J=15.0 Hz), 3.63 (6H, s), 3.77 (3H, s), 3.81 (3H, s), 6.29 (2H, s), 6.51 (1H, d, J=1.4 Hz), 6.67 (1H, dd, J=8.3, 1.4 Hz), 6.69 (1H, d, J=8.3 Hz); $^{13}$C NMR (125 MHz, CDCl$_3$): δ 24.4, 25.9, 33.4, 39.5, 55.6 (2×C), 55.8, 56.0 (2×C), 57.9, 60.1, 60.8, 106.5 (2×C), 110.6, 112.7, 120.4, 131.8, 131.9, 134.4, 136.4, 136.6, 147.4, 148.1, 152.7 (2×C). IR (KBr) 3007, 2905, 1582, 1514 cm$^{-1}$. EIMS m/z (rel int) 439 (44, M$^+$), 325 (100); HREIMS m/z calcd for C$_{26}$H$_{33}$NO$_5$: 439.2359; found: 439.2351 [M]$^+$.

2-(3,4-Dimethoxyphenyl)-3-(3-methoxyphenyl)-4,6,7,8,9,9a-hexahydro-1H-quinolizine (11f)

Yield 100%; white powder, mp 106-107° C.
$^1$H NMR (500 MHz, CDCl$_3$): δ 1.30-1.43 (2H, m), 1.69-1.77 (2H, m), 1.79-1.89 (2H, m), 2.12 (1H, td, J=11.2, 4.2 Hz), 2.28-2.36 (1H, m), 2.42 (1H, dd, J=17.2, 10.5 Hz), 2.53 (1H, d, J=17.2 Hz), 3.04-3.13 (2H, m), 3.52 (3H, s), 3.61 (3H, s), 3.62 (1H, d, J=16.6 Hz), 3.80 (3H, s), 6.48 (1H, s), 6.60 (1H, t, J=1.4 Hz), 6.63-6.70 (4H, m), 7.07 (1H, t, J=7.4 Hz); $^{13}$C NMR (125 MHz, CDCl$_3$): δ 24.3, 25.9, 33.3, 39.4, 55.1, 55.5, 55.6, 55.7, 55.9, 60.2, 110.5, 112.1, 112.9, 114.7, 120.4, 121.5, 128.9, 131.9 (2×C), 134.2, 142.4, 147.4, 147.9, 159.2. IR (KBr) 3060, 2924, 1601, 1578, 1512 cm$^{-1}$. EIMS m/z (rel int) 379 (100, M$^+$); HREIMS m/z calcd for C$_{24}$H$_{29}$NO$_3$: 379.2147; found: 379.2142 [M]$^+$.

Julandine (11g)

Yield 100%; white powder, mp 143-145° C. (M. A. Ciufolini, F. Roschangar, J. Am. Chem. Soc. 1996, 118, 12082-12089) mp 135-137° C.).
$^1$H NMR (500 MHz, CDCl$_3$): δ 1.29-1.40 (2H, m), 1.66-1.76 (2H, m), 1.78-1.88 (2H, m), 2.10 (1H, td, J=11.3, 4.2 Hz), 2.26-2.33 (1H, m), 2.39 (1H, dd, J=17.3, 11.7 Hz), 2.53 (1H, d, J=17.3 Hz), 3.01-3.11 (2H, m), 3.53 (3H, s), 3.60 (1H, d, J=16.6 Hz), 3.72 (3H, s), 3.80 (3H, s), 6.46 (1H, s), 6.65-6.68 (2H, m), 6.69 (2H, d, J=8.7 Hz), 6.97 (2H, d, J=8.7 Hz); $^{13}$C NMR (125 MHz, CDCl$_3$): δ 24.3, 25.9, 33.3, 39.5, 55.1, 55.4, 55.6, 55.7, 57.9, 60.4, 110.4, 113.0, 113.4 (2×C), 120.5, 130.1 (2×C), 131.2, 131.4, 133.2, 134.5, 147.2, 147.9, 158.0. IR (KBr) 3086, 2932, 1605, 1574, 1512 cm$^{-1}$. EIMS m/z (rel int) 379 (55, M$^+$), 265 (100); HREIMS m/z calcd for C$_{24}$H$_{29}$NO$_3$: 379.2147; found: 379.2154 [M]+.

3-(2,3,4-Trimethoxyphenyl)-2-(3,4-dimethoxyphenyl)-4,6,7,8,9,9a-hexahydro-1H-quinolizine (11h)

Yield 97%; pale yellow syrup.
$^1$H NMR (500 MHz, CDCl$_3$): δ 1.36-1.44 (2H, m), 1.71-1.77 (2H, m), 1.81-1.89 (2H, m), 2.08-2.15 (1H, m), 2.32-2.40 (1H, m), 2.47-2.55 (2H, m), 3.06 (1H, d, J=11.6 Hz), 3.11 (1H, d, J=16.7 Hz), 3.50 (1H, d, J=16.7 Hz), 3.59 (3H, s), 3.79 (3H, s), 3.80 (3H, s), 3.81 (3H, s), 3.82 (3H, s), 6.46 (1H, d, J=8.6 Hz), 6.54 (1H, d, J=1.8 Hz), 6.63 (1H, d, J=8.6 Hz), 6.68 (1H, d, J=8.3 Hz), 6.71 (1H, dd, J=8.3, 1.8 Hz); $^{13}$C NMR (125 MHz, CDCl$_3$): δ 24.4, 25.8, 33.2, 39.1, 55.4, 55.5, 55.7, 55.9, 57.9, 60.3, 60.6, 60.7, 107.0, 110.4, 112.3, 120.0, 125.7, 127.5, 129.3, 132.1, 134.5, 142.0, 147.2, 147.7, 151.6, 152.6. IR (KBr) 3021, 2936, 1599, 1516 cm$^{-1}$. EIMS m/z (rel int) 439 (100, M$^+$); HREIMS m/z calcd for C$_{26}$H$_{33}$NO$_5$: 439.2359; found: 439.2353 [M]$^+$.

2,3-Bis(3,4-dimethoxyphenyl)-4,6,7,8,9,9a-hexahydro-1H-quinolizine (11i)

Yield 95%; white powder, mp 153-154° C.
$^1$H NMR (500 MHz, CDCl$_3$): δ 1.28-1.43 (2H, m), 1.70-1.78 (2H, m), 1.78-1.90 (2H, m), 2.12 (1H, td, J=11.3, 4.8 Hz), 2.27-2.35 (1H, m), 2.39 (1H, dd, J=17.3, 12.0 Hz), 2.54 (1H, d, J=17.3 Hz), 3.02-3.14 (2H, m), 3.57 (3H, s), 3.60 (3H, s), 3.63 (1H, d, J=16.9 Hz), 3.80 (3H, s), 3.81 (3H, s), 6.51 (1H, d, J=1.6 Hz), 6.55 (1H, d, J=1.65 Hz), 6.62-6.70 (4H, m); $^{13}$C NMR (125 MHz, CDCl$_3$): δ 24.4, 25.9, 33.4, 39.6, 55.5, 55.6, 55.7, 55.8 (2×C), 57.9, 60.2, 110.6, 110.7, 112.8, 113.0, 120.6, 121.0, 131.6 (2×C), 133.5, 134.6, 147.3, 147.5, 148.1, 148.3. IR (KBr) 3048, 2943, 1601, 1582, 1520, 1501 cm$^{-1}$. EIMS m/z (rel int) 409 (73, M$^+$), 165 (100); HREIMS m/z calcd for C$_{25}$H$_{31}$NO$_4$: 409.2253; found: 409.2250 [M]$^+$.

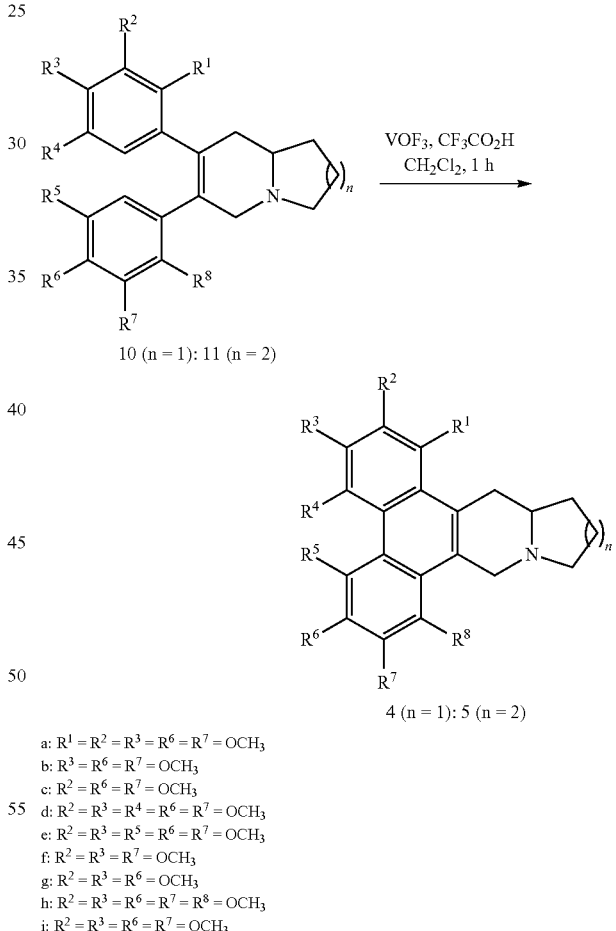

6. Synthesis of compounds 4a-i and 5a-i by oxidative coupling 10 (n = 1): 11 (n = 2)

4 (n = 1): 5 (n = 2)

a: R$^1$ = R$^2$ = R$^3$ = R$^6$ = R$^7$ = OCH$_3$
b: R$^3$ = R$^6$ = R$^7$ = OCH$_3$
c: R$^2$ = R$^6$ = R$^7$ = OCH$_3$
d: R$^2$ = R$^3$ = R$^4$ = R$^6$ = R$^7$ = OCH$_3$
e: R$^2$ = R$^3$ = R$^5$ = R$^6$ = R$^7$ = OCH$_3$
f: R$^2$ = R$^3$ = R$^7$ = OCH$_3$
g: R$^2$ = R$^3$ = R$^6$ = OCH$_3$
h: R$^2$ = R$^3$ = R$^6$ = R$^7$ = R$^8$ = OCH$_3$
i: R$^2$ = R$^3$ = R$^6$ = R$^7$ = OCH$_3$

Typical procedure for the synthesis of compounds 4a-i and 5a-i by the oxidative coupling reaction of cis-stilbene derivatives 10a-i and 11a-i. Method A: A 0.04 M solution of stilbene derivatives 10b, 10c, 10f, 10g, 10i, 11b, 11c, 11f, 11g, and 11i (0.2 mmol) in anhydrous CH$_2$Cl$_2$ (5 mL) was added to VOF$_3$ (1.0 mmol) at 0° C. and the mixture was stirred for 15 min. TFA (2.8 mmol) was added and the purple mixture was stirred at 0° C. for 1 h.

Method B: A 0.04 M solution of stilbene derivatives 10a, 10d, 10e, 10h, 11a, 11d, 11e, and 11h (0.2 mmol) in anhydrous $CH_2Cl_2$ (5 mL) was added to $VOF_3$ (0.4 mmol) at −20° C. and the mixture was stirred for 15 min. TFA (1.1 mmol) was added and the purple mixture was stirred at −20° C. for 1 h. The reaction mixture was quenched with 10% aqueous NaOH. Then, the resulting mixture was warmed to RT and stirred for 5 min. The biphasic $H_2O/CH_2Cl_2$ mixture was separated and the $H_2O$ layer was extracted with $CH_2Cl_2$ (3×5 mL). The combined $CH_2Cl_2$ extracts were dried over anhydrous $MgSO_4$ and filtered. The filtrate was concentrated and the residue was purified by column chromatography over silica gel by eluting with a mixture of $CHCl_3$/MeOH (100:1 v/v), affording pure phenanthroindolizidines 4a-i (and phenanthroquinolizidines 5a-i). The complete spectral data of these compounds are given below.

1,2,3,6,7-Pentamethoxy-11,12,12a,13-tetrahydro-10H-9a-azacyclopenta[b]triphenylene (4a)

Yield 70%; white powder, mp 225-226° C.
$^1$H NMR (500 MHz, $CDCl_3$): δ 1.71-1.81 (1H, m), 1.86-1.96 (1H, m), 1.99-2.09 (1H, m), 2.15-2.23 (1H, m), 2.26-2.35 (1H, m), 2.41 (1H, q, J=8.5 Hz), 3.24 (1H, dd, J=16.9, 11.0 Hz), 3.49 (1H, t, J=8.5 Hz), 3.68 (1H, d, J=14.5 Hz), 3.77 (1H, d, J=16.9 Hz), 3.90 (3H, s), 4.00 (3H, s), 4.05 (3H, s), 4.08 (3H, s), 4.09 (3H, s), 4.66 (1H, d, J=14.5 Hz), 7.15 (1H, s), 7.68 (1H, s), 7.82 (1H, s); $^{13}$C NMR (125 MHz, $CDCl_3$): δ 21.8, 31.3, 37.0, 55.2, 55.6, 55.9, 56.0, 56.1, 60.7, 61.1, 61.5, 99.6, 103.0, 104.0, 121.4, 123.1, 125.1, 126.4, 126.9, 127.6, 142.5, 148.5, 149.3, 151.8, 151.9. IR (KBr) 3005, 2937, 1599, 1530, 1501 cm$^{-1}$. EIMS m/z (rel int) 423 (40, M$^+$), 354 (100); HREIMS m/z calcd for $C_{25}H_{29}NO_5$: 423.2046; found: 423.2041 [M]+.

Deoxypergularinine (4b)

Yield 82%; white powder, mp 218-219° C. (G Han, Y. Liu, Q. Wang, Org. Lett. 2013, 15, 5334-5337; mp 225-228° C.).
$^1$H NMR (500 MHz, $CDCl_3$): δ 1.70-1.81 (1H, m), 1.87-1.96 (1H, m), 1.98-2.08 (1H, m), 2.19-2.28 (1H, m), 2.42-2.53 (2H, m), 2.94 (1H, dd, J=15.8, 10.7 Hz), 3.42 (1H, dd, J=15.8, 2.8 Hz), 3.47 (1H, t, J=8.4 Hz), 3.65 (1H, d, J=14.5 Hz), 4.01 (3H, s), 4.05 (3H, s), 4.10 (3H, s), 4.60 (1H, d, J=14.5 Hz), 7.16 (1H, s), 7.21 (1H, dd, J=9.0, 2.5 Hz), 7.89 (1H, d, J=2.5 Hz), 7.92 (1H, s), 7.95 (1H, d, J=9.0 Hz); $^{13}$C NMR (125 MHz, $CDCl_3$): δ 21.6, 31.3, 33.6, 54.0, 55.2, 55.5, 55.9, 56.0, 60.2, 103.2, 104.0, 104.6, 114.8, 123.4, 125.2, 125.3, 125.6, 125.7, 127.0, 130.4, 148.3, 149.4, 157.6. IR (KBr) 2959, 1616, 1531, 1512 cm$^{-1}$. EIMS m/z (rel int) 363 (22, M$^+$), 294 (100); HREIMS m/z calcd for $C_{23}H_{25}NO_3$: 363.1834; found: 363.1841 [M]$^+$.

2,6,7-Trimethoxy-11,12,12a,13-tetrahydro-10H-9a-azacyclopenta[b]triphenylene (4c)

Yield 86%; white powder, mp 187-189° C.
$^1$H NMR (500 MHz, $CDCl_3$): δ 1.72-1.83 (1H, m), 1.88-1.97 (1H, m), 1.99-2.10 (1H, m), 2.20-2.29 (1H, m), 2.43-2.53 (2H, m), 2.91 (1H, dd, J=15.5, 10.5 Hz), 3.37 (1H, dd, J=15.5, 2.5 Hz), 3.48 (1H, td, J=8.5, 1.7 Hz), 3.68 (1H, d, J=14.8 Hz), 3.98 (3H, s), 4.05 (3H, s), 4.10 (3H, s), 4.63 (1H, d, J=14.8 Hz), 7.16 (1H, s), 7.23 (1H, dd, J=9.0, 2.6 Hz), 7.35 (1H, d, J=2.6 Hz), 7.94 (1H, s), 8.45 (1H, d, J=9.0 Hz); $^{13}$C NMR (125 MHz, $CDCl_3$): δ 21.7, 31.3, 33.7, 54.2, 55.2, 55.4, 55.9, 56.0, 60.2, 103.2, 103.4, 104.5, 115.5, 123.5, 123.8, 124.0, 124.2, 126.5, 128.3, 132.2, 148.6, 148.7, 157.8. IR (KBr) 3098, 2932, 1620, 1612, 1516, 1501 cm$^{-1}$. EIMS m/z (rel int) 363 (18, M$^+$), 294 (100); HREIMS m/z calcd for $C_{23}H_{25}NO_3$: 363.1834; found: 363.1839 [M]$^+$.

4-Methoxytylophorine (4d)

Yield 89%; white powder, mp 193-194° C. (K. V. Rao, R. A. Wilson, B. M. Cummings, J. Pharm. Sci. 1970, 59, 1501-1502; mp 198-200° C.).
$^1$H NMR (500 MHz, $CDCl_3$): δ 1.73-1.82 (1H, m), 1.88-1.96 (1H, m), 1.99-2.08 (1H, m), 2.19-2.28 (1H, m), 2.41-2.52 (2H, m), 2.89 (1H, dd, J=14.8, 11.1 Hz), 3.02 (1H, d, J=14.6 Hz), 3.47 (1H, t, J=8.2 Hz), 3.67 (1H, d, J=14.8 Hz), 3.99 (3H, s), 4.03 (3H, s), 4.04 (3H, s), 4.05 (3H, s), 4.09 (3H, s), 4.62 (1H, d, J=14.6 Hz), 7.17 (1H, s), 7.20 (1H, s), 9.20 (1H, s); $^{13}$C NMR (125 MHz, $CDCl_3$): δ 21.6, 31.3, 34.2, 54.2, 55.2, 55.8 (3×C), 60.3, 60.5, 61.4, 100.6, 102.6, 108.1, 118.0, 123.5, 125.0, 126.3, 127.7, 128.8, 142.1, 147.9, 148.0, 151.6, 151.7. IR (KBr) 3021, 2932, 1607, 1504 cm$^{-1}$. EIMS m/z (rel int) 423 (24, M$^+$), 354 (100); HREIMS m/z calcd for $C_{25}H_{29}NO_5$: 423.2046; found: 423.2048 [M]$^+$.

2,3,5,6,7-Pentamethoxy-11,12,12a,13-tetrahydro-10H-9a-azacyclopenta[b]triphenylene (4e)

Yield 85%; white powder, mp 169-170° C.
$^1$H NMR (500 MHz, $CDCl_3$): δ 1.75-1.83 (1H, m), 1.89-1.98 (1H, m), 2.00-2.09 (1H, m), 2.21-2.29 (1H, m), 2.43-2.53 (2H, m), 2.93 (1H, dd, J=15.8, 10.4 Hz), 3.36 (1H, dd, J=15.8, 1.8 Hz), 3.48 (1H, t, J=8.2 Hz), 3.66 (1H, d, J=14.4 Hz), 3.98 (3H, s), 4.03 (3H, s), 4.04 (3H, s), 4.06 (3H, s), 4.09 (3H, s), 4.60 (1H, d, J=14.4 Hz), 7.04 (1H, s), 7.33 (1H, s), 9.19 (1H, s); $^{13}$C NMR (125 MHz, $CDCl_3$): δ 21.6, 31.3, 34.0, 54.4, 55.2, 55.7, 55.8, 55.9, 60.1, 60.5, 61.4, 99.6, 103.5, 108.0, 117.8, 123.7, 125.9, 126.5, 127.3, 128.1, 142.0, 148.0, 148.1, 151.7, 151.8. IR (KBr) 3019, 2934, 1607, 1528, 1506 cm$^{-1}$. EIMS m/z (rel int) 423 (35, M$^+$), 354 (100); HREIMS m/z calcd for $C_{25}H_{29}NO_5$: 423.2046; found: 423.2052 [M]+.

Desmethoxytylophorine (4f)

Yield 85%; white powder, mp 196-197° C. (M. J. Niphakis, G I. Georg, M. J. Niphakis, Org. Lett. 2011, 13, 196-199; mp 203-205° C.).
$^1$H NMR (500 MHz, $CDCl_3$): δ 1.72-1.82 (1H, m), 1.87-1.97 (1H, m), 1.99-2.09 (1H, m), 2.19-2.28 (1H, m), 2.41-2.52 (2H, m), 2.91 (1H, dd, J=15.6, 10.5 Hz), 3.36 (1H, dd, J=15.6, 2.5 Hz), 3.47 (1H, td, J=8.6, 1.8 Hz), 3.65 (1H, d, J=14.7 Hz), 3.97 (3H, s), 4.05 (3H, s), 4.09 (3H, s), 4.63 (1H, d, J=14.7 Hz), 7.20 (1H, d, J=2.5 Hz), 7.22 (1H, dd, J=9.0, 2.5 Hz), 7.30 (1H, s), 7.92 (1H, s), 8.45 (1H, d, J=9.0 Hz); $^{13}$C NMR (125 MHz, $CDCl_3$): δ 21.6, 31.3, 34.0, 54.0, 55.1, 55.4, 55.9, 56.0, 60.1, 103.2, 103.8, 104.0, 115.3, 123.2, 124.1, 124.3, 125.3, 126.2, 128.7, 130.6, 148.6, 148.7, 157.7. IR (KBr) 3017, 2920, 1616, 1501 cm$^{-1}$. EIMS m/z (rel int) 363 (43, M$^+$), 294 (100); HREIMS m/z calcd for $C_{23}H_{25}NO_3$: 363.1834; found: 363.1835 [M]$^+$.

Antofine (4g)

Yield 86%; white powder, mp 217° C. (decomp.) (M. J. Niphakis, G I. Georg, M. J. Niphakis, Org. Lett. 2011, 13, 196-199; mp 221-222° C. (decomp.)).

¹H NMR (500 MHz, CDCl₃): δ 1.73-1.83 (1H, m), 1.87-1.97 (1H, m), 1.98-2.10 (1H, m), 2.20-2.29 (1H, m), 2.41-2.56 (2H, m), 2.89 (1H, dd, J=14.2, 11.0 Hz), 3.34 (1H, dd, J=14.2, 2.0 Hz), 3.46 (1H, t, J=8.0 Hz), 3.70 (1H, d, J=14.8 Hz), 4.01 (3H, s), 4.06 (3H, s), 4.11 (3H, s), 4.69 (1H, d, J=14.8 Hz), 7.20 (1H, dd, J=9.0, 2.4 Hz), 7.31 (1H, s), 7.81 (1H, d, J=9.0 Hz), 7.90 (1H, d, J=2.4 Hz), 7.91 (1H, s); ¹³C NMR (125 MHz, CDCl₃): δ 21.6, 31.3, 33.7, 53.9, 55.1, 55.5, 55.9, 56.0, 60.2, 103.8, 104.0, 104.7, 114.9, 123.5, 124.1, 124.3, 125.5, 126.7, 127.1, 130.2, 148.3, 149.4, 157.5. IR (KBr) 3106, 2947, 1616, 1531, 1512 cm⁻¹. EIMS m/z (rel int) 363 (26, M⁺), 294 (100); HREIMS m/z calcd for $C_{23}H_{25}NO_3$: 363.1834; found: 363.1827 [M]⁺.

2,3,6,7,8-Pentamethoxy-11,12,12a,13-tetrahydro-10H-9a-azacyclopenta[b]triphenylene (4h)

Yield 54%; white powder, mp 231° C. (decomp.).
¹H NMR (500 MHz, CDCl₃): δ 1.70-1.79 (1H, m), 1.86-1.95 (1H, m), 1.96-2.06 (1H, m), 2.22-2.30 (1H, m), 2.44 (1H, q, J=9.0 Hz), 2.45-2.53 (1H, m), 2.95 (1H, dd, J=15.8, 10.5 Hz), 3.34-3.45 (2H, m), 3.89 (1H, d, J=16.3 Hz), 3.95 (3H, s), 3.98 (3H, s), 4.05 (3H, s), 4.08 (3H, s), 4.09 (3H, s), 4.93 (1H, d, J=16.3 Hz), 7.29 (1H, s), 7.67 (1H, s), 7.80 (1H, s); ¹³C NMR (125 MHz, CDCl₃): δ 21.7, 31.7, 35.0, 55.2, 55.8, 55.9, 56.0, 56.7, 59.6, 61.0, 61.4, 99.7, 103.8, 103.9, 120.1, 123.2, 126.6 (2×C), 126.7, 127.5, 142.2, 148.5, 149.2, 151.4, 151.8. IR (KBr) 3009, 2932, 1609, 1572, 1526 cm⁻¹. EIMS m/z (rel int) 423 (53, M⁺) 354 (100); HREIMS m/z calcd for $C_{25}H_{29}NO_5$: 423.2046; found: 423.2040 [M]⁺.

Tylophorine (4i)

Yield 85%; white powder, mp 270° C. (decomp) (T. H. Chuang, S. J. Lee, C. W. Yang, P. L. Wu, Org. Biomol. Chem. 2006, 4, 860-867; mp 270° C. (decomp.)).
¹H NMR (500 MHz, CDCl₃): δ 1.71-1.83 (1H, m), 1.87-1.96 (1H, m), 1.98-2.09 (1H, m), 2.19-2.27 (1H, m), 2.41-2.51 (2H, m), 2.89 (1H, dd, J=15.6, 10.5 Hz), 3.34 (1H, dd, J=15.6, 2.7 Hz), 3.47 (1H, td, J=8.5, 1.9 Hz), 3.64 (1H, d, J=14.6 Hz), 4.04 (3H, s), 4.05 (3H, s), 4.11 (6H, s), 4.60 (1H, d, J=14.6 Hz), 7.14 (1H, s), 7.29 (1H, s), 7.80 (1H, s), 7.81 (1H, s); ¹³C NMR (125 MHz, CDCl₃): δ 21.6, 31.3, 33.8, 54.1, 55.2, 55.8, 55.9, 56.0 (2×C), 60.2, 103.2, 103.4, 103.5, 104.0, 123.4, 123.6, 124.4, 125.9, 126.1, 126.3, 148.4, 148.5, 148.7 (2×C). IR (KBr) 3094, 2928, 1620, 1512 cm⁻¹. EIMS m/z (rel int) 393 (26, M⁺), 324 (100); HREIMS m/z calcd for $C_{24}H_{27}NO_4$: 393.1940; found: 393.1943 [M]⁺.

1,2,3,6,7-Pentamethoxy-10,11,12,13,13a,14-hexahydro-9H-9a-azabenzo[b]triphenylene (5a)

Yield 77%; white powder, mp 191-192° C.
¹H NMR (500 MHz, CDCl₃): δ 1.36-1.47 (1H, m), 1.47-1.57 (1H, m), 1.72-1.92 (3H, m), 1.96-2.03 (1H, m), 2.16-2.30 (2H, m), 3.23 (1H, dd, J=17.4, 10.7 Hz), 3.30 (1H, d, J=10.7 Hz), 3.54-3.65 (2H, m), 3.90 (3H, s), 3.99 (3H, s), 4.05 (3H, s), 4.08 (3H, s), 4.09 (3H, s), 4.40 (1H, d, J=15.3 Hz), 7.12 (1H, s), 7.67 (1H, s), 7.82 (1H, s); ¹³C NMR (125 MHz, CDCl₃): δ 24.3, 25.9, 33.6, 37.8, 55.9 (2×C), 56.0, 56.4, 57.0, 57.7, 61.1, 61.4, 99.6, 102.8, 104.1, 120.7, 123.0, 124.6, 125.1, 126.6, 126.8, 142.4, 148.3, 149.2, 151.8 (2×C). IR (KBr) 3059, 2922, 1609, 1531, 1503 cm⁻¹. EIMS m/z (rel int) 437 (43, M⁺), 354 (100); HREIMS m/z calcd for $C_{26}H_{31}NO_5$: 437.2202; found: 437.2208 [M]⁺.

Boehmeriasin A (5b)

Yield 88%; white powder, mp 217-219° C. (Q. Wang, Z. Wang, Tetrahedron Lett. 2010, 51, 1377-1379; mp 222-223° C.).
¹H NMR (500 MHz, CDCl₃): δ 1.39-1.58 (2H, m), 1.75-1.85 (2H, m), 1.85-1.92 (1H, m), 1.99-2.06 (1H, m), 2.31 (1H, td, J=10.9, 3.6 Hz), 2.36-2.43 (1H, m), 2.93 (1H, dd, J=16.3, 10.2 Hz), 3.18 (1H, dd, J=16.3, 2.2 Hz), 3.29 (1H, d, J=10.9 Hz), 3.59 (1H, d, J=15.1 Hz), 4.01 (3H, s), 4.05 (3H, s), 4.10 (3H, s), 4.34 (1H, d, J=15.1 Hz), 7.13 (1H, s), 7.20 (1H, dd, J=9.0, 2.3 Hz), 7.87-7.95 (3H, m), 7.92 (1H, s); ¹³C NMR (125 MHz, CDCl₃): δ 24.3, 26.0, 33.7, 34.7, 55.5, 55.9, 56.0, 56.2, 56.4, 57.5, 103.1, 104.1, 104.6, 114.7, 123.3, 124.2, 125.0, 125.2, 125.9, 130.3, 148.2, 149.4, 157.5. IR (KBr) 3001, 2920, 1612, 1512 cm⁻¹. EIMS m/z (rel int) 377 (23, M⁺), 294 (100); HREIMS m/z calcd for $C_{24}H_{27}NO_3$: 377.1991; found: 377.2000 [M]⁺.

2,6,7-Trimethoxy-10,11,12,13,13a,14-hexahydro-9H-9a-azabenzo[b]triphenylene (5c)

Yield 84%; white powder, mp 182-184° C.
¹H NMR (500 MHz, CDCl₃): δ 1.39-1.59 (2H, m), 1.75-1.85 (2H, m), 1.85-1.92 (1H, m), 2.00-2.06 (1H, m), 2.31 (1H, td, J=11.2, 3.3 Hz), 2.34-2.41 (1H, m), 2.89 (1H, dd, J=16.5, 11.2 Hz), 3.11 (1H, dd, J=16.5, 3.4 Hz), 3.29 (1H, d, J=11.2 Hz), 3.60 (1H, d, J=15.5 Hz), 3.97 (3H, s), 4.04 (3H, s), 4.09 (3H, s), 4.36 (1H, d, J=15.5 Hz), 7.13 (1H, s), 7.22 (1H, dd, J=9.1, 2.6 Hz), 7.29 (1H, d, J=2.6 Hz), 7.93 (1H, s), 8.43 (1H, d, J=9.1 Hz); ¹³C NMR (125 MHz, CDCl₃): δ 24.4, 26.0, 33.8, 34.7, 55.4, 55.9, 56.0, 56.3 (2×C), 57.5, 103.1, 103.4, 104.5, 115.3, 123.3, 123.4, 124.0, 124.1, 125.4, 127.2, 131.6, 148.5, 148.6, 157.7. IR (KBr) 3098, 2924, 1616, 1508 cm⁻¹. EIMS m/z (rel int) 377 (21, M⁺), 294 (100); HREIMS m/z calcd for $C_{24}H_{27}NO_3$: 377.1991; found: 377.1986 [M]⁺.

4,7-Dimethoxycryptoplerine (5d)

Yield 90%; white powder, mp 101-102° C.
¹H NMR (500 MHz, CDCl₃): δ 1.39-1.50 (1H, m), 1.50-1.60 (1H, m), 1.76-1.85 (2H, m), 1.85-1.93 (1H, m), 2.00-2.08 (1H, m), 2.31 (1H, td, J=11.2, 4.0 Hz), 2.35-2.44 (1H, m), 2.90 (1H, dd, J=16.0, 11.0 Hz), 3.07 (1H, dd, J=16.0, 3.2 Hz), 3.29 (1H, d, J=11.2 Hz), 3.61 (1H, d, J=15.4 Hz), 3.98 (3H, s), 4.03 (3H, s), 4.04 (6H, s), 4.08 (3H, s), 4.37 (1H, d, J=15.4 Hz), 7.13 (1H, s), 7.14 (1H, s), 9.19 (1H, s); ¹³C NMR (125 MHz, CDCl₃): δ 24.2, 25.8, 33.6, 35.1, 55.7, 55.8, 55.9, 56.2, 56.4, 57.6, 60.5, 61.3, 100.5, 102.5, 108.2, 117.9, 123.5, 124.5, 125.1, 126.5, 128.2, 142.1, 147.9, 148.0, 151.7 (2×C). IR (KBr) 3017, 2934, 1609, 1506 cm⁻¹. EIMS m/z (rel int) 437 (24, M⁺), 354 (100); HREIMS m/z calcd for $C_{26}H_{31}NO_5$: 437.2202; found: 437.2206 [M]⁺.

2,3,5,6,7-Pentamethoxy-10,11,12,13,13a,14-hexahydro-9H-9a-azabenzo[b]triphenylene (5e)

Yield 88%; white powder, mp 166-167° C.
¹H NMR (500 MHz, CDCl₃): δ 1.39-1.59 (2H, m), 1.75-1.86 (2H, m), 1.86-1.93 (1H, m), 2.00-2.08 (1H, m), 2.31 (1H, td, J=11.3, 3.7 Hz), 2.35-2.42 (1H, m), 2.92 (1H, dd, J=16.5, 11.1 Hz), 3.12 (1H, dd, J=16.5, 3.5 Hz), 3.29 (1H, d, J=11.3 Hz), 3.59 (1H, d, J=15.2 Hz), 3.98 (3H, s), 4.03 (3H, s), 4.04 (3H, s), 4.06 (3H, s), 4.08 (3H, s), 4.34 (1H, d, J=15.2 Hz), 7.01 (1H, s), 7.28 (1H, s), 9.18 (1H, s); ¹³C NMR (125 MHz, CDCl₃): δ 24.3, 25.9, 33.7, 35.1, 55.7, 55.8, 55.9, 56.3, 56.6, 57.4, 60.5, 61.3, 99.5, 103.3, 108.1, 117.7, 123.5, 124.8, 125.9, 126.9, 127.0, 141.9, 147.9, 148.0, 151.7, 151.8. IR (KBr) 3055, 2930, 1609, 1524, 1501 cm$^{-1}$. EIMS m/z (rel int) 437 (32, M$^+$), 354 (100); HREIMS m/z calcd for C$_{26}$H$_{31}$NO$_5$: 437.2202; found: 437.2208 [M]$^+$.

2,3,7-Trimethoxy-10,11,12,13,13a,14-hexahydro-9H-9a-azabenzo[b]triphenylene (5f)

Yield 86%; white powder, mp 156-158° C.
$^1$H NMR (500 MHz, CDCl$_3$): δ 1.37-1.58 (2H, m), 1.72-1.93 (3H, m), 1.98-2.05 (1H, m), 2.24-2.39 (2H, m), 2.87 (1H, dd, J=16.6, 12.3 Hz), 3.07 (1H, d, J=16.6 Hz), 3.27 (1H, d, J=10.8 Hz), 3.56 (1H, d, J=15.2 Hz), 3.96 (3H, s), 4.04 (3H, s), 4.08 (3H, s), 4.35 (1H, d, J=15.2 Hz), 7.16 (1H, s), 7.18-7.25 (2H, m), 7.90 (1H, s), 8.43 (1H, d, J=8.8 Hz); $^{13}$C NMR (125 MHz, CDCl$_3$): δ 24.4, 26.0, 33.8, 35.0, 55.4, 55.9, 56.0, 56.1, 56.3, 57.4, 103.3, 103.8, 103.9, 115.0, 123.2, 124.1, 124.2, 124.7, 125.1, 127.6, 130.2, 148.5, 148.7, 157.7. IR (KBr) 3102, 2920, 1616, 1508 cm$^{-1}$. EIMS m/z (rel int) 377 (44, M$^+$), 294 (100); HREIMS m/z calcd for C$_{24}$H$_{27}$NO$_3$: 377.1991; found: 377.2000 [M]$^+$.

Cryptopleurine (5g)

Yield 88%; white powder, mp 197° C. (decomp.) (S. Kim, Y. M. Lee, J. Lee, T. Lee, Y. Fu, Y. Song, J. Cho, D. Kim, J. Org. Chem. 2007, 72, 4886-4891; mp 177-179° C.).
$^1$H NMR (500 MHz, CDCl$_3$): δ 1.38-1.60 (2H, m), 1.75-1.85 (2H, m), 1.85-1.93 (1H, m), 1.99-2.07 (1H, m), 2.30 (1H, td, J=11.0, 3.6 Hz), 2.35-2.45 (1H, m), 2.88 (1H, dd, J=16.0, 11.0 Hz), 3.07 (1H, dd, J=16.0, 4.0 Hz), 3.27 (1H, d, J=11.0 Hz), 3.63 (1H, d, J=15.3 Hz), 4.01 (3H, s), 4.05 (3H, s), 4.09 (3H, s), 4.43 (1H, d, J=15.3 Hz), 7.18 (1H, dd, J=9.0, 2.4 Hz), 7.24 (1H, s), 7.78 (1H, d, J=9.0 Hz), 7.88 (1H, d, J=2.4 Hz), 7.89 (1H, s); $^{13}$C NMR (125 MHz, CDCl$_3$): δ 24.3, 25.9, 33.7, 34.6, 55.5, 55.9, 56.0 (2×C), 56.2, 57.6, 103.8, 103.9, 104.8, 114.8, 123.4, 123.7, 124.1, 124.4, 125.5, 126.5, 130.1, 148.3, 149.4, 157.4. IR (KBr) 3005, 2936, 1612, 1531, 1512 cm$^{-1}$. EIMS m/z (rel int) 377 (25, M$^+$), 294 (100); HREIMS m/z calcd for C$_{24}$H$_{27}$NO$_3$: 377.1991; found: 377.1990 [M]$^+$.

2,3,6,7,8-Pentamethoxy-10,11,12,13,13a,14-hexahydro-9H-9a-azabenzo[b]triphenylene (5h)

Yield 71%; white powder, mp 211° C. (decomp.).
$^1$H NMR (500 MHz, CDCl$_3$): δ 1.41-1.54 (2H, m), 1.75-1.81 (2H, m), 1.84-1.90 (1H, m), 2.02-2.08 (1H, m), 2.28 (1H, td, J=11.3, 3.4 Hz), 2.36-2.44 (1H, m), 2.92 (1H, dd, J=16.2, 3.4 Hz), 3.14 (1H, dd, J=16.2, 2.6 Hz), 3.25 (1H, d, J=11.3 Hz), 3.84 (1H, d, J=16.5 Hz), 3.94 (3H, s), 3.98 (3H, s), 4.06 (3H, s), 4.08 (3H, s), 4.09 (3H, s), 4.74 (1H, d, J=16.5 Hz), 7.25 (1H, s), 7.67 (1H, s), 7.80 (1H, s); $^{13}$C NMR (125 MHz, CDCl$_3$): δ 24.3, 26.0, 34.0, 35.6, 55.9, 56.0 (2×C), 56.1, 57.0, 58.6, 61.0, 61.4, 99.7, 103.8, 103.9, 119.7, 123.2, 125.4, 126.1, 126.6, 126.7, 142.2, 148.5, 149.2, 151.2, 151.7. IR (KBr) 3021, 2932, 1601, 1530, 1501 cm$^{-1}$. EIMS m/z (rel int) 437 (58, M$^+$), 354 (100); HREIMS m/z calcd for C$_{26}$H$_{31}$NO$_5$: 437.2202; found: 437.2209 [M]$^+$.

7-Methoxycryptopleurine (5i)

Yield 92%; white powder, mp 246-248° C. (T. H. Chuang, S. J. Lee, C. W. Yang, P. L. Wu, Org. Biomol. Chem. 2006, 4, 860-867; mp 245-247° C. (decomp.)).

$^1$H NMR (500 MHz, CDCl$_3$): δ 1.40-1.60 (2H, m), 1.75-1.86 (2H, m), 1.86-1.94 (1H, m), 2.00-2.08 (1H, m), 2.32 (1H, td, J=11.1, 3.5 Hz), 2.36-2.45 (1H, m), 2.91 (1H, dd, J=16.5, 11.5 Hz), 3.13 (1H, dd, J=16.5, 3.9 Hz), 3.30 (1H, d, J=11.1 Hz), 3.62 (1H, d, J=15.1 Hz), 4.05 (3H, s), 4.06 (3H, s), 4.11 (6H, s), 4.37 (1H, d, J=15.1 Hz), 7.14 (1H, s), 7.26 (1H, s), 7.82 (1H, s), 7.83 (1H, s); $^{13}$C NMR (125 MHz, CDCl$_3$): δ 24.4, 26.0, 33.8, 34.9, 55.9, 56.0, 56.1 (2×C), 56.3, 56.4, 57.6, 103.1, 103.4, 103.6, 103.9, 123.4, 123.5, 123.9, 125.0, 125.3 (2×C), 148.4, 148.5, 148.7 (2×C). IR (KBr) 3094, 2920, 1620, 1531, 1512 cm$^{-1}$. EIMS m/z (rel int) 407 (23, M$^+$), 324 (100); HREIMS m/z calcd for C$_{25}$H$_{29}$NO$_4$: 407.2097; found: 407.2096 [M]$^+$.

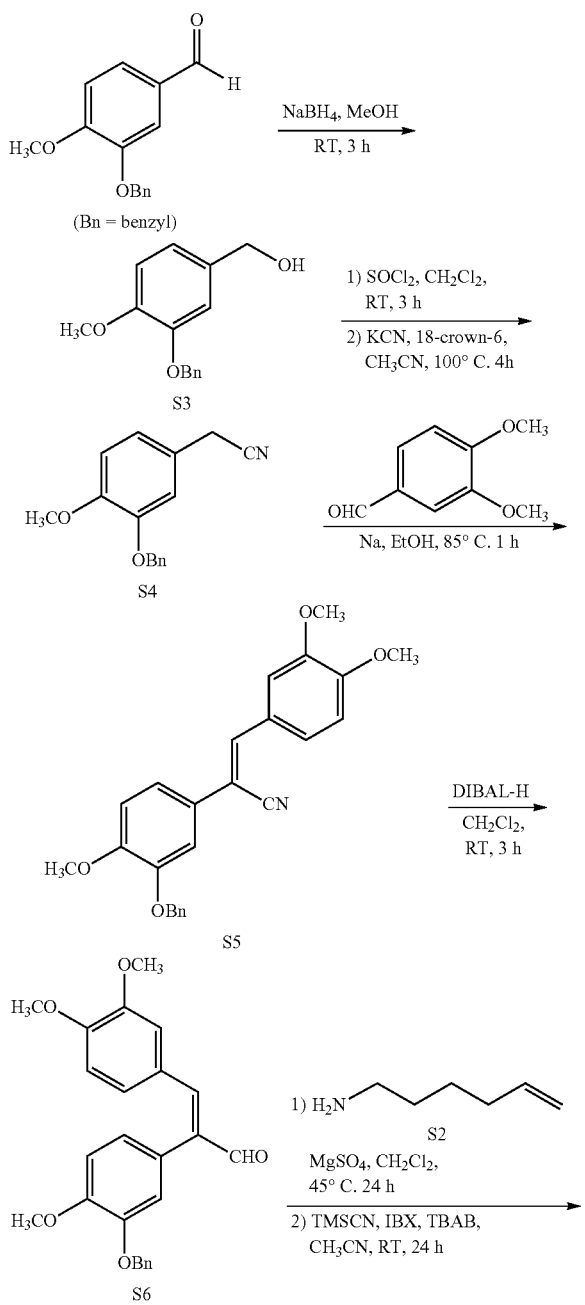

7. Synthesis of 7-hydroxycryptopleurine (20)

-continued

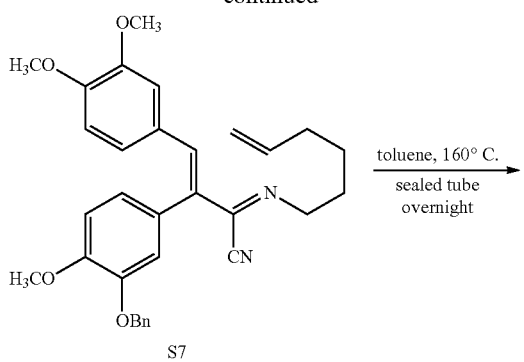

S7 toluene, 160° C.
sealed tube
overnight

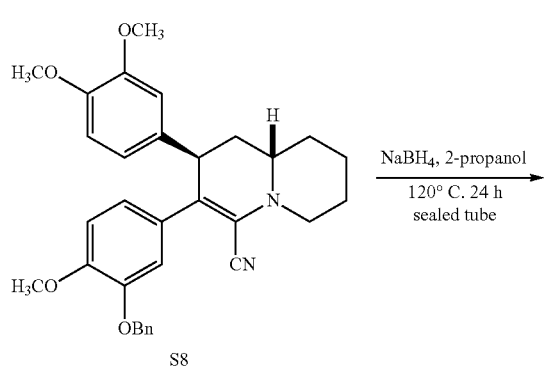

S8

NaBH₄, 2-propanol
120° C. 24 h
sealed tube

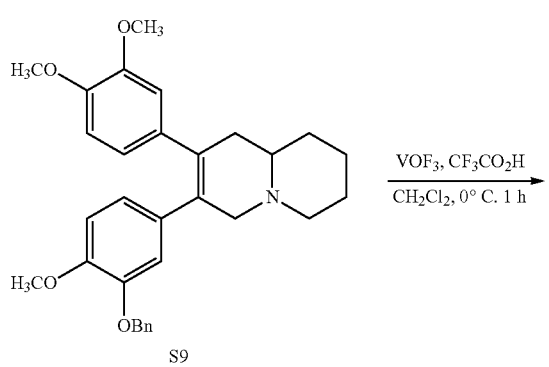

S9

VOF₃, CF₃CO₂H
CH₂Cl₂, 0° C. 1 h

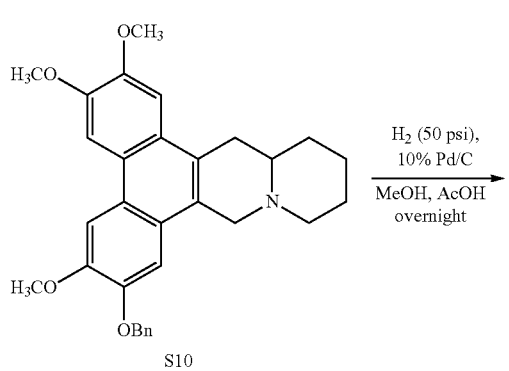

S10

H₂ (50 psi),
10% Pd/C
MeOH, AcOH
overnight

-continued

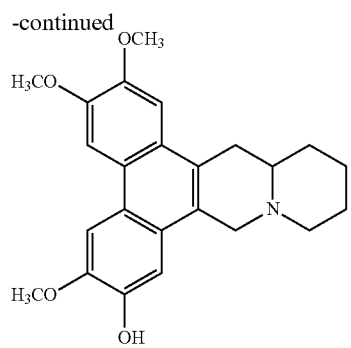

NaBH₄ (283.8 mg, 7.5 mmol) was carefully added to a stirred solution of 3-benzyloxy-4methoxybenzaldehyde (1.21 g, 5.0 mmol) in MeOH (25 mL) at 0° C. The mixture was stirred at RT under $N_2$ for 1 h. TFA (2.8 mmol) was added, and the purple mixture was stirred at 0° C. for 1 h. The solvent was evaporated under reduced pressure. Then, the residue was diluted with a saturated aqueous NH₄Cl solution (25 mL) and extracted with EtOAc (5×20 mL). The combined organic extract was washed with H₂O (3×20 mL), dried over anhydrous MgSO₄, and filtered. The filtrate was concentrated, and the residue was purified by column chromatography over silica gel by eluting with a mixture of hexane/EtOAc (1:1 v/v), affording pure compound S3.

(3-Benzyloxy-4-methoxyphenyl)methanol (S3)

Yield 86%; white needle, mp 73-74° C. (hexane-EtOAc) (A. R. Battersby, R. Binks, R. J. Francis, D. J. McCaldin, H. Ramuz, J. Chem. Soc. 1964, 3600-3610; mp 72-73° C.).
$^1$H NMR (500 MHz, CDCl₃): δ 2.59 (1H, br s), 3.78 (3H, s), 4.42 (2H, s), 5.04 (2H, s), 6.78 (1H, d, J=8.2 Hz), 6.81 (1H, dd, J=8.2, 1.7 Hz), 6.88 (1H, d, J=1.7 Hz), 7.25 (1H, t, J=7.4 Hz), 7.31 (2H, t, J=7.4 Hz), 7.39 (2H, d, J=7.4 Hz). $^{13}$C NMR (125 MHz, CDCl₃): δ 55.8, 64.5, 70.7, 111.6, 112.9, 119.7, 127.2 (2×C), 127.6, 128.3 (2×C), 133.5, 136.9, 148.0, 148.9. IR (KBr) 3356, 3021, 2963, 1609, 1508 cm$^{-1}$. EIMS m/z (rel int) 244 (14, M⁺), 91 (100). HREIMS m/z calcd for $C_{15}H_{16}O_3$: 244.1099; found: 244.1090 [M]⁺.

A 1.0 M solution of thionyl chloride in CH₂Cl₂ (6.0 mL, 6.0 mmol) was added to a solution of alcohol S3 (977.0 mg, 4.0 mmol) in CH₂Cl₂ (20 mL), and the mixture was stirred at RT under $N_2$ for 2 h. The solvent was evaporated under reduced pressure, affording the corresponding chloride quantitatively. Without further purification, the chloride was dissolved in anhydrous CH₃CN (20 mL), and KCN (390.7 mg, 6.0 mmol) and 18-crown-6 (42.3 mg, 0.16 mmol) were added. The suspension was refluxed under $N_2$ for overnight. The solvent was evaporated under reduced pressure. Then, the residue was diluted with H₂O (25 mL) and extracted with EtOAc (5×20 mL). The combined organic extract was washed with H₂O (3×20 mL), dried over anhydrous MgSO₄, and filtered. The filtrate was concentrated, and the residue was purified by column chromatography over silica gel by eluting with a mixture of hexane/EtOAc (5:1 v/v), affording pure compound S4.

2-(3-Benzyloxy-4-methoxyphenyl)acetonitrile (S4)

Yield 90%; white needle, mp 83-84° C. (hexane-EtOAc) (A. R. Battersby, R. Binks, R. J. Francis, D. J. McCaldin, H. Ramuz, J. Chem. Soc. 1964, 3600-3610; mp 79.5-80.5° C.).

$^1$H NMR (500 MHz, CDCl$_3$): δ 3.63 (2H, s), 3.88 (3H, s), 5.15 (2H, s), 6.83-6.88 (3H, m), 7.31 (1H, t, J=7.3 Hz), 7.37 (2H, t, J=7.3 Hz), 7.44 (2H, d, J=7.3 Hz). $^{13}$C NMR (125 MHz, CDCl$_3$): δ 23.1, 56.1, 71.2, 112.2, 113.9, 118.0, 120.8, 122.1, 127.4 (2×C), 128.0, 128.6 (2×C), 136.7, 148.6, 149.6. IR (KBr) 3017, 2940, 2839, 2253, 1597, 1512 cm$^{-1}$. EIMS m/z (rel int) 253 (100, M$^+$). HREIMS m/z calcd for C$_{16}$H$_{15}$NO$_2$: 253.1103; found: 253.1101 [M]$^+$.

The typical procedure for the synthesis of (Z)-2,3-diphenylacrylonitrile 17 was used and the resulting precipitate was filtered, affording pure compound S5.

Yield 98%; yellow needle, mp 71-72° C. (hexane-EtOAc).

$^1$H NMR (500 MHz, CDCl$_3$): δ 3.92 (3H, s), 3.93 (3H, s), 3.96 (3H, s), 5.20 (2H, s), 6.90 (1H, d, J=8.4 Hz), 6.92 (1H, d, J=8.4 Hz), 7.18 (1H, s), 7.21-7.25 (2H, m), 7.27-7.35 (2H, m), 7.39 (2H, t, J=7.5 Hz), 7.48 (2H, d, J=7.5 Hz), 7.65 (1H, s). $^{13}$C NMR (125 MHz, CDCl$_3$): δ 55.9, 56.0, 56.1, 71.4, 108.4, 110.7, 111.0, 111.8, 111.9, 118.7, 119.3, 124.0, 126.9, 127.5 (2×C), 127.6, 128.0, 128.6 (2×C), 136.7, 140.3, 148.4, 149.0, 150.5, 150.9. IR (KBr) 3017, 2932, 2207, 1597, 1520 cm$^{-1}$. EIMS m/z (rel int) 401 (47, M$^+$), 91 (100). HREIMS m/z calcd for C$_{25}$H$_{23}$NO$_4$: 401.1627; found: 401.1619 [M]$^+$.

The typical procedure for the synthesis of (E)-2,3-diphenylacrylaldehydes 16 was used, and the crude product was purified by column chromatography over silica gel by eluting with a mixture of hexane/EtOAc (3:1 v/v), affording pure (E)-2,3-diphenylacrylaldehyde 56 as the major product.

(E)-2-(3-Benzyloxy-4-methoxyphenyl)-3-(3,4-dimethoxyphenyl)acrylaldehyde (S6)

Yield 86%; yellow granule, mp 114-115° C. (hexane-EtOAc).

$^1$H NMR (500 MHz, CDCl$_3$): δ 3.45 (3H, s), 3.87 (3H, s), 3.89 (3H, s), 5.06 (2H, s), 6.63 (1H, s), 6.75 (1H, d, J=8.3 Hz), 6.79 (1H, s), 6.81 (1H, d, J=8.3 Hz), 6.92 (1H, d, J=8.1 Hz), 6.97 (1H, d, J=8.1 Hz), 7.23 (1H, t, J=7.4 Hz), 7.25 (1H, s), 7.28 (2H, t, J=7.4 Hz), 7.37 (2H, d, J=7.4 Hz), 9.68 (1H, s). $^{13}$C NMR (125 MHz, CDCl$_3$): δ 55.1, 55.8, 56.0, 70.9, 110.5, 112.3, 112.4, 115.2, 122.5, 125.6, 126.1, 126.9, 127.3 (2×C), 127.7, 128.3 (2×C), 136.7, 139.4, 148.3, 148.6, 149.6, 150.1, 150.9, 193.8. IR (KBr) 3017, 2932, 2839, 2708, 1678, 1597, 1512 cm$^{-1}$. EIMS m/z (rel int) 404 (47, M$^+$), 91 (100). HREIMS m/z calcd for C$_{25}$H$_{24}$O$_5$: 404.1624; found: 404.1633 [M]$^+$.

The typical procedure for the synthesis of a-iminonitriles 15a-i was used, and the crude product was purified by a short column chromatography over silica gel by eluting with a mixture of hexane/EtOAc (4:1 v/v), affording pure compound S7.

(3E)-3-(3-Benzyloxy-4-methoxyphenyl)-2-(5-hexenylimino)-4-(3,4-dimethoxyphenyl)-3-butenenitrile (S7)

Yield 80%; yellow syrup.

$^1$H NMR (500 MHz, CDCl$_3$): δ 1.44 (2H, quintet, J=7.2 Hz), 1.66 (2H, quintet, J=7.2 Hz), 2.08 (2H, q, J=7.2 Hz), 3.44 (3H, s), 3.85 (3H, s), 3.86 (2H, t, J=7.2 Hz), 3.89 (3H, s), 4.95 (1H, d, J=10.2 Hz), 5.00 (1H, d, J=17.1 Hz), 5.05 (2H, s), 5.79 (1H, ddt, J=17.1, 10.2, 7.2 Hz), 6.41 (1H, d, J=1.6 Hz), 6.69 (1H, d, J=8.4 Hz), 6.74 (1H, s), 6.74-6.78 (2H, m), 6.93 (1H, d, J=7.9 Hz), 7.23 (1H, t, J=7.3 Hz), 7.28 (2H, t, J=7.3 Hz), 7.35 (2H, d, J=7.3 Hz), 7.41 (1H, s). $^{13}$C NMR (125 MHz, CDCl$_3$): δ 26.5, 29.8, 33.3, 55.1, 55.7, 55.9, 58.7, 70.9, 109.6, 110.5, 112.1, 112.3, 114.7, 115.8, 123.0, 124.9, 127.2 (2×C), 127.5, 127.7, 127.8, 128.4 (2×C), 135.9, 136.7, 138.4, 139.7, 144.8, 148.1, 148.5, 149.5, 149.8. IR (KBr) 3017, 2936, 2218, 1574, 1508 cm$^{-1}$. EIMS m/z (rel int) 510 (43, M$^+$), 91 (100). HREIMS m/z calcd for C$_{32}$H$_{34}$N$_2$O$_4$: 510.2519; found: 510.2522 [M]$^+$.

The typical procedure for IADA was used, and the crude product was purified by column chromatography over silica gel by eluting with a mixture of hexane/EtOAc (3:1 v/v), affording cycloadducts S8.

trans-3-(3-Benzyloxy-4-methoxyphenyl)-2-(3,4-dimethoxyphenyl)-2,6,7,8,9,9a-hexahydro-1H quinolizine-4-carbonitrile (S8)

Yield 95%; yellow syrup.

$^1$H NMR (500 MHz, CDCl$_3$): δ 1.23-1.34 (2H, m), 1.48-1.63 (2H, m), 1.69-1.81 (3H, m), 2.02 (1H, td, J=13.0, 5.0 Hz), 2.55-2.63 (1H, m), 2.66 (1H, td, J=11.8, 2.4 Hz), 3.70 (1H, d, J=5.0 Hz), 3.80 (3H, s), 3.81 (3H, s), 3.85 (3H, s), 3.98 (1H, d, J=11.8 Hz), 5.00 (1H, d, J=12.4 Hz), 5.03 (1H, d, J=12.4 Hz), 6.63 (1H, d, J=1.9 Hz), 6.69 (1H, dd, J=8.4, 1.9 Hz), 6.75 (1H, d, J=8.4 Hz), 6.78 (1H, d, J=8.4 Hz), 6.82 (1H, d, J=2.1 Hz), 6.90 (1H, dd, J=8.4, 2.1 Hz), 7.25-7.33 (5H, m). $^{13}$C NMR (125 MHz, CDCl$_3$): δ 23.9, 25.8, 31.8, 37.3, 43.1, 50.7, 51.4, 55.6, 55.7 (2×C), 70.9, 110.9, 111.2, 111.4, 114.3, 115.9, 120.3, 120.7, 121.6, 127.1 (2×C), 127.5, 128.3 (2×C), 131.7, 137.0, 137.2, 147.4, 147.5, 148.7, 149.0. IR (KBr) 3017, 2940, 2214, 1597, 1512 cm$^{-1}$. EIMS m/z (rel int) 510 (100, M$^+$). HREIMS m/z calcd for C$_{32}$H$_{34}$N$_2$O$_4$: 510.2519; found: 510.2518 [M]$^+$.

The typical procedure for the synthesis of cis-stilbene derivatives 11a-i by reductive decyanization was used and the crude product was purified by column chromatography over silica gel by eluting with EtOAc, affording pure stilbene derivative S9.

3-(3-Benzyloxy-4-methoxyphenyl)-2-(3,4-dimethoxyphenyl)-4,6,7,8,9,9a-hexahydro-1H-quinolizine (S9)

Yield 95%; white syrup.

$^1$H NMR (500 MHz, CDCl$_3$): δ 1.28-1.40 (2H, m), 1.67-1.75 (2H, m), 1.78-1.86 (2H, m), 2.09 (1H, td, J=11.3, 5.0 Hz), 2.25-2.32 (1H, m), 2.37 (1H, dd, J=17.1, 10.0 Hz), 2.50 (1H, d, J=17.1 Hz), 3.00 (1H, d, J=16.6 Hz), 3.07 (1H, d, J=11.3 Hz), 3.53 (3H, s), 3.54 (1H, d, J=16.6 Hz), 3.80 (3H, s), 3.81 (3H, s), 4.83 (1H, d, J=12.4 Hz), 4.88 (1H, d, J=12.4 Hz), 6.45 (1H, d, J=1.8 Hz), 6.59-6.62 (2H, m), 6.62-6.67 (2H, m), 6.69 (1H, d, J=8.3 Hz), 7.26-7.34 (5H, m). $^{13}$C NMR (125 MHz, CDCl$_3$): δ 24.3, 25.9, 33.3, 39.5, 55.5 (2×C), 55.7, 55.9, 57.9, 60.1, 71.0, 110.6, 111.4, 112.7, 115.7, 120.6, 121.8, 127.1 (2×C), 127.7, 128.4 (2×C), 131.3, 131.4, 133.4, 134.6, 137.2, 147.3, 147.6, 148.1, 148.2. IR (KBr) 3017, 2932, 1589, 1512 cm$^{-1}$. EIMS m/z (rel int) 485 (61, M$^+$), 91 (100). HREIMS m/z calcd for C$_{31}$H$_{35}$NO$_4$: 485.2566; found: 485.2562 [M]$^+$.

The typical procedure for oxidative coupling reaction (method A) was used and the crude product was purified by column chromatography over silica gel by eluting with a mixture of CHCl$_3$/MeOH (100:1 v/v), affording pure Bn-protected phenanthroquinolizidine S10.

7-Benzyloxy-2,3,6-trimethoxy-10,11,12,13,13a,14-hexahydro-9H-9a-azabenzo[b]triphenylene (S10)

Yield 96%; white solid, mp 207° C. (demcomp.).
$^1$H NMR (500 MHz, CDCl$_3$): δ 1.36-1.56 (2H, m), 1.71-1.83 (2H, m), 1.83-1.90 (1H, m), 1.96-2.03 (1H, m), 2.21-2.36 (2H, m), 2.83 (1H, dd, J=16.0, 10.6 Hz), 3.02 (1H, d, J=16.0 Hz), 3.22 (1H, d, J=10.7 Hz), 3.44 (1H, d, J=15.1 Hz), 4.02 (3H, s), 4.08 (3H, s), 4.09 (3H, s), 4.17 (1H, d, J=15.1 Hz), 5.28 (2H, s), 7.15 (1H, s), 7.19 (1H, s), 7.31 (1H, t, J=7.4 Hz), 7.38 (2H, t, J=7.4 Hz), 7.52 (2H, d, J=7.4 Hz), 7.78 (1H, s), 7.81 (1H, s). $^{13}$C NMR (125 MHz, CDCl$_3$): δ 24.3, 25.9, 33.7, 34.7, 55.9, 56.0, 56.1, 56.2 (2×C), 57.5, 71.3, 103.5, 103.9, 104.1, 106.4, 123.5, 123.7, 123.8, 124.9, 125.1, 125.3, 127.6 (2×C), 128.0, 128.6 (2×C), 137.1, 147.7, 148.4, 148.7, 149.0. IR (KBr) 3017, 2936, 1616, 1512 cm$^{-1}$. EIMS m/z (rel int) 483 (39, M$^+$), 309 (100). HREIMS m/z calcd for C$_{31}$H$_{33}$NO$_4$: 483.2410; found: 483.2418 [M]$^+$.

A mixture of Bn-protected phenanthroquinolizidine S10 (96.7 mg, 0.2 mmol), 10% Pd/C (10 mg), AcOH (0.2 mL), and MeOH (20 mL) was stirred at 50° C. for overnight under H$_2$ (50 psi) in a Parr high-pressure vessel. The mixture was filtered and concentrated under reduced pressure. The residue was diluted with CH$_2$Cl$_2$ (30 mL), washed with saturated NaHCO$_3$ (10 mL) and H$_2$O (3×10 mL), dried over anhydrous MgSO$_4$, and filtered. The filtrate was concentrated, and the residue was purified by column chromatography over silica gel by eluting with a mixture of CHCl$_3$/MeOH (30:1 v/v), affording pure phenanthroquinolizidine 20.

7-Hydroxy-2,3,6-trimethoxy-10,11,12,13,13a,14-hexahydro-9H-9a-azabenzo[b]triphenylene (20)

Yield 90%; white solid, mp 114-115° C.
$^1$H NMR (500 MHz, CDCl$_3$): δ 1.39-1.49 (1H, m), 1.51-1.61 (1H, m), 1.74-1.84 (2H, m), 1.85-1.92 (1H, m), 1.99-2.05 (1H, m), 2.24-2.33 (1H, m), 2.34-2.42 (1H, m), 2.89 (1H, dd, J=16.4, 10.5 Hz), 3.06 (1H, dd, J=16.4, 3.5 Hz), 3.27 (1H, d, J=10.9 Hz), 3.52 (1H, d, J=15.2 Hz), 4.03 (3H, s), 4.04 (3H, s), 4.08 (3H, s), 4.32 (1H, d, J=15.2 Hz), 7.21 (1H, s), 7.26 (1H, s), 7.65 (1H, s), 7.71 (1H, s). $^{13}$C NMR (125 MHz, CDCl$_3$): δ 24.3, 25.8, 33.6, 34.6, 55.9 (2×C), 56.0, 56.1 (2×C), 57.6, 102.5, 103.4, 104.0, 106.8, 123.1, 123.6, 124.3, 124.9, 125.0, 125.1, 145.1, 146.5, 148.4, 148.6. IR (KBr) 3395, 3013, 2932, 1616, 1504 cm$^{-1}$. EIMS m/z (rel int) 393 (26, M$^+$), 310 (100). HREIMS m/z calcd for C$_{24}$H$_{27}$NO$_4$: 393.1940; found: 393.1930 [M]$^+$.

8. Typical Procedure for Cell Viability Assay

The breast carcinoma (MCF-7), lung carcinoma (H1299), and prostate carcinoma (DU145) cells were first plated at a density of 5×10$^3$ cells per well in 96-well plates for overnight and then treated with different concentrations of these compounds. After 48 h of treatment, 100 L of MTT solution was added to each well and the cells were incubated for 1 h at 37° C. Then, the MTT solution was completely removed and 50 L of DMSO was added to solubilize the MTT formazan crystals. Finally, the absorbance was measured using a MQX200R microplate reader (BioTek, VT, USA) at a wavelength of 550 nm.

9. The Effect of Compound 20 on H1299 Cell Cycle Associated Protein

9.1 Western Blot Analysis

H1299 cells were first seeded at a density of 3×10$^5$ cells per well in six-well plates overnight and then treated with compound 20 at three different concentrations (7, 14, and 21 nM) for 12, 24, and 48 h. The cells were washed with PBS buffer and lysed in ice-cold RIPA buffer for 30 min. The supernatant was collected and centrifuged at 15,000 rpm at 4° C. for 30 min. The protein concentration was measured with a Bio-Rad assay using a MQX200R microplate reader (BioTek, VT, USA). The cell lysates were separated by 10% SDS-PAGE and electrophoretically transferred onto polyvinylidene difluoride (PVDF) membranes (Millipore, Bedford, Mass.). After several washes, the membranes were blocked with 5% skim milk in TBST (tris-buffered saline containing 0.1% Tween-20) at room temperature for 1 h and incubated with different primary antibodies against cyclin D1, CDK4, cyclin E, CDK2, cyclin B1, and CDK1 (1:2000 dilution) at 4° C. for overnight. Then, the membranes were washed with TBST three times and investigated using horseradish peroxidase (HRP)-conjugated secondary antibody (1:4000) at room temperature for 1 h. After washing three times in TBST, the bound antibody was visualized using ECL Western Blotting Reagent (PerkinElmer, Boston), and chemiluminescence was detected using a Fuji Medical X-ray film (Tokyo, Japan).

9.2 Statistical Analysis

All the data were expressed as means±SEM for three replicate experiments. The statistical comparison between the treatments was carried out using the GraphPad Prism 5.0 software. One-way ANOVA followed by Tukey's honestly significant difference (HSD) posthoc test were applied, with significances of P<0.05 or P<0.01.

10. Rotarod Test for Motor Coordination

The protocol of rotarod test was based on those described in the literature [Y. Z. Lee, C. W Yang, H. Y. Hsu, Y. Q. Qiu, T. K. Yeh, H. Y. Chang, et al., J. Med. Chem. 2012, 55, 10363-10377] with slight modifications. Eight week-old female athymic nude mice were used. All the animal experiments followed ethical standards, and the protocols have been reviewed and approved by the Animal Care and Use Committee of China Medical University (IACUC approval no: 102-235-N). The mice were randomly divided into two groups (n=3) and treated with compound 20 (10 mg/kg) or 7-methoxycryptopleurine 5i (0.08 mg/kg) intraperitoneally. The compounds were dissolved in a mixture of 2.5% DMSO, 2.5% EtOH, 5% Cremophor EL, and 90% normal saline. Each group was administered once daily, five days per week for 15 times in total. After 15 administrations of the compounds, the mice were placed on the rotarod apparatus for training (day 1) and test (days 2-4) with the rod set in motion at a constant speed of 5 rpm. The latency time to fall from the rotating rod was recorded for a maximum of 180 s.

11. Results

The cytotoxic activities of 18 compounds 4a-i and 5a-i were evaluated against three human cancer cell lines, breast carcinoma (MCF-7), lung carcinoma (H1299), and prostate carcinoma (DU145), using tylophorine (4i) and 7-methoxycryptopleurine (5i) for comparison. The cytotoxic activities of phenanthroindolizidines 4a-i and phenanthroquinolizidines 5a-i are shown in Table 4. First, all the phenanthroquinolizidines 5a-i were more active than the corresponding phenanthroindolizidines 4a-i.[14] Moreover, a 28 to 36-fold increase in the cytotoxicity was observed for compound 5f relative to compound 4f (entry 6). This indicates that the phenanthroquinolizidines tolerated more substituent changes at the C-6 position than phenanthroindolizidines. In the phenanthroindolizidine series, the IC$_{50}$ ratio of compounds 4a-h to tylophorine (4i) followed the order: 4a~4h~4e>4f>>4b~4e>4d>4g; however, in the phenanthroquinolizidine series, the IC$_{50}$ ratio of compounds 5a-h to 7-methoxycryptopleurine (5i) followed the order: 5c~5a~5h~5b>>5f~5d>5e>5g. The data indicate that when the C-1 and C-8 substituents were converted from methoxy to hydrogen and the C-3 substituent was converted from hydrogen to methoxy, the cytotoxicity decreased dramatically. Interestingly, C-6 methoxylation is more important than C-2 methoxylation for cytotoxicity in the phenanthroindolizidine series, whereas a reverse trend was observed in the phenanthroquinolizidine series. Moreover, the C-4 and C-5 methoxylation showed only slightly deleterious effects on the cytotoxicity (entries 4 and 5 vs. entry 9). Notably, the absence of a methoxy group at the C-7 position did not significantly affect the cytotoxicity in the two series of alkaloids (entry 7 vs. entry 9). Based on the SAR results, a more polar phenanthroquinolizidine, 7-hydroxycryptopleurine (20), was designed and synthesized to decrease the CNS toxicity and increase the water solubility. 7-Hydroxycryptopleurine (20) was obtained from 3-benzyloxy-4-methoxybenzaldehyde in 40.7% overall yield by the above newly developed method.

TABLE 4

$IC_{50}$ values of compounds 4a-i and 5a-i against three human cancer cell lines.

| Entry | Compound 4 {5} | $IC_{50}$ (nM) [a] | | |
|---|---|---|---|---|
| | | MCF-7 | H1299 | DU145 |
| 1 | 4a {5a} | >2500 {276.4} | >2500 {251.9} | >2500 {271.9} |
| 2 | 4b {5b} | 304.9 {272.4} | 235.2 {210.6} | 175.6 {184.5} |
| 3 | 4c {5c} | 2481.0 {392.5} | >2500 {314.4} | 2152.0 {278.9} |
| 4 | 4d {5d} | 61.2 {61.9} | 54.1 {54.4} | 58.8 {35.7} |
| c | 4e {5e} | 223.9 {19.3} | 165.3 {27.6} | 150.1 {23.8} |
| 6 | 4f {5f} | 1909.0 {68.7} | 2017.0 {57.3} | 1510.0 {41.8} |
| 7 | 4g {5g} | 42.4 {11.3} | 32.5 {9.0} | 30.3 {4.6} |
| 8 | 4h {5h} | >2500 {277.4} | >2500 {232.4} | >2500 {214.9} |
| 9 | 4i {5i} | 41.1 {10.7} | 30.9 {7.1} | 28.3 {4.5} |

[a] The values in the brackets show the $IC_{50}$ of compounds 5.

Compound 20 exhibited potent cytotoxicity activity against MCF-7, H1299, and DU145 cancer cell lines, with $IC_{50}$ values of 6.4, 5.2, and 4.4 nM, respectively. The normal human lung fibroblast cell line, MRC-5, was more resistant than other cancer cell lines ($IC_{50}$ 26.0 nM). The results indicate that compound 20 possesses enhanced and selective cytotoxicity for cancer cells. The antiproliferative activity of compound 20 in H1299 cancer cells was partly mediated by a decrease in cyclin D1-cdk4, cyclin E-cdk2, and cyclin B1-cdk1 expression. Moreover, compound 20 was soluble in the solvent system—2.5% DMSO, 2.5% EtOH, 5% Cremophor EL, and 90% normal saline—in the range of ~1.3 mg/mL, whereas the solubility of 7-methoxycryptopleurine (5i) was less than 0.08 mg/mL. The neurotoxicity of the compounds was investigated by a rotarod test for motor coordination for three consecutive days. The compound 20-treated group exhibited better motor coordination than the compound 5i-treated group, as shown in the FIGURE.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to a univalent radical alkyl-O—, e.g. $CH_3O$—.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

Alkyl, aryl, cyclyl, heteroaryl, and heterocyclyl mentioned herein include both substituted and unsubstituted moieties. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted with alkyl, aryl, heteroaryl, halogen, hydroxyl, amino, mercapto, cyano, or nitro.

The compounds mentioned above may contain one or more asymmetric centers. Thus, they occur as racemates and racemic mixtures, single enantiomers, individual diastereomers, diastereomeric mixtures, or cis- or trans-isomeric forms. All such isomeric forms are contemplated.

The invention claimed is:
1. An improved method for preparing a phenanthroindolizidine and phenanthroquinolizidine alkaloid having a structure represented by the following formula (I):

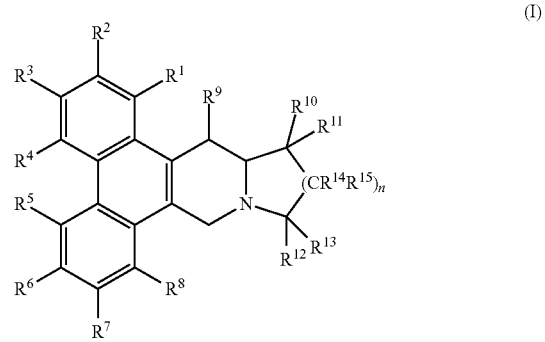

(I)

wherein n is 1, 2, or 3; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$, independently, is H, halogen, alkyl, aryl, cyclyl, heteroaryl, heterocyclyl, OH, alkoxy, or amino; and wherein the improvement comprises the method comprising step (5): conducting a reductive decyanization reaction of an aminoacrylonitrile derivative having a structure represented by the following formula (III) to obtain a diphenyltetrahydropyridine derivative having a structure represented by the following formula (II):

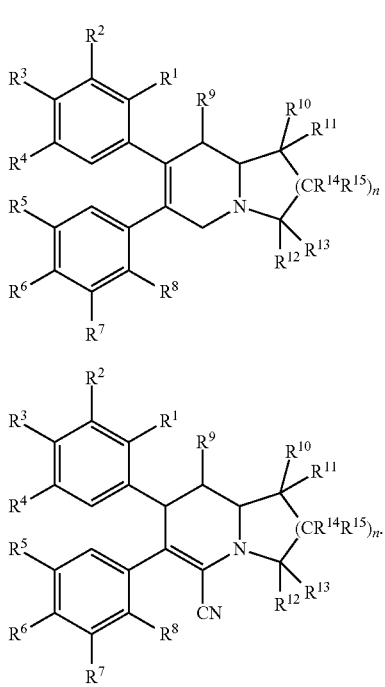

2. The method of claim 1 further comprising a step (6): conducting an aryl-aryl oxidative coupling reaction of the diphenyltetrahydropyridine derivative (II) to obtain the phenanthroindolizidine and phenanthroquinolizidine alkaloid (I).

3. The method of claim 1 further comprising a step (4): conducting an intramolecular aza-Diels-Alder reaction of an iminonitrile derivative having a structure represented by the following formula (IV) and to obtain the aminoacrylonitrile derivative (III):

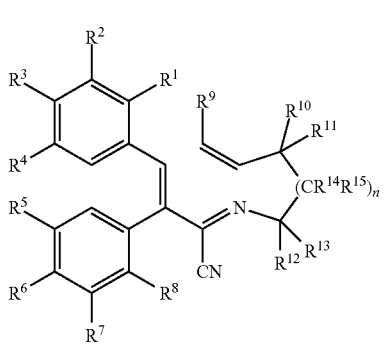

wherein n is 1, 2, or 3; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$, independently, is H, halogen, alkyl, aryl, cyclyl, heteroaryl, heterocyclyl, OH, alkoxy, or amino.

4. The method of claim 3 further comprising step (3): reacting a vinyl amine derivative having a structure represented by the following formula (V) with an (E)-2,3-diphenylacrylaldehyde derivative having a structure represented by the following formula (VI) to obtain the iminonitrile derivative (IV):

$$HR^9C=C-CR^{10}R^{11}-(CR^{14}R^{15})-CR^{12}R^{13}NH_2 \quad (V)$$

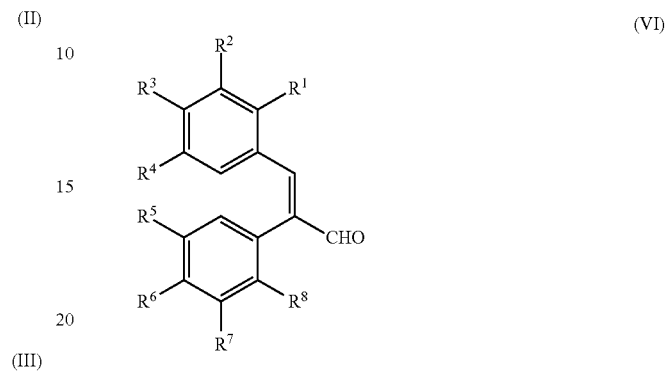

wherein n is 1, 2, or 3; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$, independently, is H, halogen, alkyl, aryl, cyclyl, heteroaryl, heterocyclyl, OH, alkoxy, or amino.

5. The method of claim 4 further comprising a step (2): conducting a diisobutylaluminum hydride reduction of a diphenylacrylonitrile derivative having a structure represented by the following formula (VII) to obtain the (E)-2,3-diphenylacrylaldehyde derivative (VI):

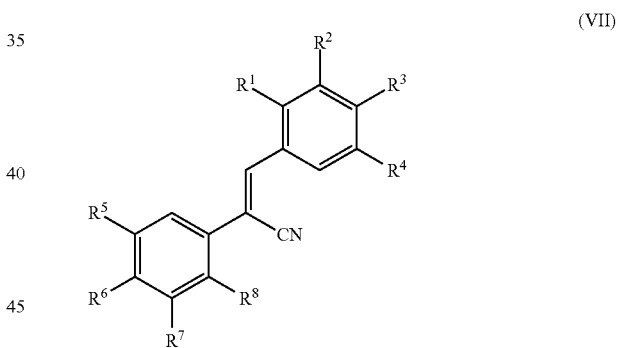

wherein each of $R^1$, $R^2$, $R^3$, $R^4$, $R^5$, $R^6$, $R^7$, and $R^8$, independently, is H, halogen, alkyl, aryl, cyclyl, heteroaryl, heterocyclyl, OH, alkoxy, or amino.

6. The method of claim 5 further comprising a step (1): conducting a Knoevenagel condensation of a benzaldehyde derivative having a structure represented by the following formula (VIII) and a phenylacetonitrile derivative having a structure represented by the following formula (IX) to obtain the diphenylacrylonitrile derivative (VII):

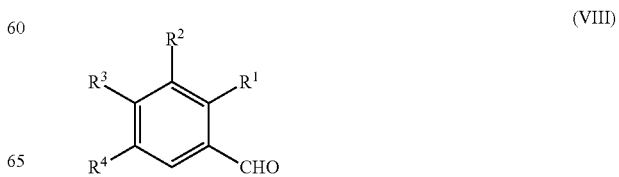

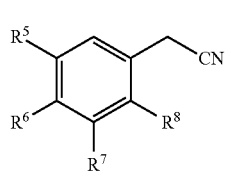 (IX)

wherein each of $R^1$, $R^2$, $R^3$, $R^4$, $R^5$, $R^6$, $R^7$, and $R^8$, independently, is H, halogen, alkyl, aryl, cyclyl, heteroaryl, heterocyclyl, OH, alkoxy, or amino.

7. The method of claim 1, wherein n=2; and $R^1$, $R^8$, $R^9$, $R^{10}$, $R^{11}$, $R^{12}$, $R^{13}$, $R^{14}$, and $R^{15}$ are H.

8. The method of claim 7, wherein each of $R^2$, $R^3$, $R^4$, $R^5$, $R^6$, and $R^7$, independently, is H, OH, or alkoxy.

9. The method of claim 8, wherein at least one of $R^2$, $R^3$, $R^4$, $R^5$, $R^6$, and $R^7$ is OH.

10. The method of claim 9, wherein $R^2$, $R^3$, and $R^6$ are methoxy; and $R^7$ is OH.

* * * * *